US008524717B2

(12) United States Patent
Guibourt et al.

(10) Patent No.: US 8,524,717 B2
(45) Date of Patent: Sep. 3, 2013

(54) OXIDASE INHIBITORS AND THEIR USE

(75) Inventors: Nathalie Guibourt, Barcelona (ES);
Alberto Ortega Munoz, Barcelona (ES); Julio Castro-Palomino Laria, Barcelona (ES)

(73) Assignee: Oryzon Genomics, S.A., Barcelona (ES)

( * ) Notice: Subject to any disclaimer, the term of this patent is extended or adjusted under 35 U.S.C. 154(b) by 0 days.

(21) Appl. No.: 13/066,616

(22) Filed: Apr. 18, 2011

(65) Prior Publication Data
US 2011/0263604 A1 Oct. 27, 2011

Related U.S. Application Data

(63) Continuation of application No. PCT/EP2009/063685, filed on Oct. 19, 2009.

(30) Foreign Application Priority Data

Oct. 17, 2008 (EP) .................................. 08166973
Jul. 17, 2009 (EP) .................................. 09165840

(51) Int. Cl.
A61K 31/4965 (2006.01)
C07D 241/04 (2006.01)

(52) U.S. Cl.
USPC ..................... 514/255.01; 544/391

(58) Field of Classification Search
USPC ..................... 544/391; 514/255.01
See application file for complete search history.

(56) References Cited

U.S. PATENT DOCUMENTS

| 3,106,578 A | 10/1963 | Kaiser et al. |
| 3,365,458 A | 1/1968 | Biel et al. |
| 3,471,522 A | 10/1969 | Biel et al. |
| 3,532,712 A | 10/1970 | Biel et al. |
| 3,532,749 A | 10/1970 | Biel et al. |
| 4,409,243 A | 10/1983 | Lieb et al. |
| 4,522,811 A | 6/1985 | Eppstein et al. |
| 6,211,244 B1 | 4/2001 | Van Wagenen et al. |
| 6,809,120 B1 | 10/2004 | Warrington et al. |
| 2003/0008844 A1 | 1/2003 | Spero et al. |
| 2003/0236225 A1 | 12/2003 | Protopopova et al. |
| 2004/0048802 A1 | 3/2004 | Ripka et al. |
| 2004/0062601 A1 | 4/2004 | Thompson |
| 2004/0132820 A1 | 7/2004 | Gosselin et al. |
| 2004/0176469 A1 | 9/2004 | Thomas |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0087206 A1 | 4/2006 | Yamada |
| 2006/0116370 A1 | 6/2006 | Dollinger et al. |
| 2006/0148904 A1 | 7/2006 | Protopopova et al. |
| 2006/0270673 A1 | 11/2006 | Duggan et al. |
| 2006/0275366 A1 | 12/2006 | Malcolm et al. |
| 2006/0287287 A1 | 12/2006 | Gerritz et al. |
| 2007/0025709 A1 | 2/2007 | Gladnick et al. |
| 2008/0139665 A1 | 6/2008 | Schuele et al. |
| 2008/0242698 A1 | 10/2008 | Flor et al. |
| 2008/0269228 A1 | 10/2008 | Moore et al. |
| 2010/0016262 A1 | 1/2010 | Mehal et al. |
| 2010/0043721 A1 | 2/2010 | Cigan |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2011/0263604 A1 | 10/2011 | Guibourt |
| 2012/0004262 A1 | 1/2012 | Guibourt |
| 2012/0264823 A1 | 10/2012 | Ortega Muñoz |
| 2012/0283266 A1 | 11/2012 | Ortega Muñoz |

FOREIGN PATENT DOCUMENTS

| EP | 1193268 | 4/2002 |
| EP | 1704859 | 9/2006 |
| EP | 1741708 | 1/2007 |
| GB | 1307341 | 2/1973 |
| JP | 2001354563 | 12/2001 |
| SU | 230169 | 8/1967 |
| WO | WO94/27947 | 12/1994 |
| WO | WO99/05142 | 2/1999 |
| WO | WO99/05143 | 2/1999 |
| WO | WO00/34283 | 6/2000 |
| WO | WO03/087064 | 6/2003 |
| WO | WO03/093297 | 11/2003 |
| WO | WO03/096989 | 11/2003 |
| WO | WO2004/020415 | 3/2004 |
| WO | WO2004/062601 | 7/2004 |
| WO | WO2004/065367 | 8/2004 |
| WO | WO2004/096135 | 11/2004 |
| WO | WO2005/009941 | 2/2005 |
| WO | WO 2005/023761 | 3/2005 |
| WO | WO2005/037843 | 4/2005 |
| WO | WO2005/058883 | 6/2005 |
| WO | WO2006/071608 | 7/2006 |
| WO | WO2006087206 | 8/2006 |
| WO | WO2007/000248 | 1/2007 |
| WO | WO2007005896 | 1/2007 |
| WO | WO2007/015824 | 2/2007 |

(Continued)

OTHER PUBLICATIONS

PCT International Search Report, PCT/EP2009/063685 dated Dec. 23, 2009.
"Histone Demethylation Mediated by the Nuclear Amine Oxidase Homolog LSD1" Y. Shi (2004) *Cell* 119, 941-953.
"Androgen receptor coactivators lysine-specific histone demethylase 1 and four and a half LIM domain protein 2 predict risk of prostate cancer recurrence." P. Kahl (2006) *Cancer Res.* 66(23), 11341-7.
"Role of the Lysine-Specific Demethylase 1 in the Proinflammatory Phenotype of Vascular Smooth Muscle Cells of Diabetic Mice" M. A. Reddy (2008) *Circ. Res.* 103, 615.
"Histone H3 lysine 4 demethylation is a target of nonselective antidepressive medications". M. G. Lee (2006) *Chem. Biol.* 13(6), 563-7.
"Trans-2-Phenylcyclopropylamine Is a Mechanism-Based Inactivator of the Histone Demethylase LSD1" D.M.Z. Schmidt (2007)*Biochemistry* 46 (14), 4408-4416.
"Facile synthesis of substituted trans-2-arylcyclopropylamine inhibitors of the human histone demethylase LSD1 and monoamine oxidases A and B". D.M. Gooden (2008) *Bioorg Med Chem Lett.* 18, 3047-51.

(Continued)

*Primary Examiner* — Rebecca Anderson
(74) *Attorney, Agent, or Firm* — TraskBritt

(57) ABSTRACT

The invention relates to phenylcyclopropylamine acetamide derivatives and their use in treating diseases.

31 Claims, No Drawings

(56) References Cited

FOREIGN PATENT DOCUMENTS

| | | |
|---|---|---|
| WO | WO2007/025144 | 3/2007 |
| WO | WO 2007/025709 * | 3/2007 |
| WO | WO2007025709 | 3/2007 |
| WO | WO2007/106016 | 9/2007 |
| WO | WO2008/033466 | 3/2008 |
| WO | WO2008/116156 | 9/2008 |
| WO | WO2009/001132 | 12/2008 |
| WO | WO2009/023179 | 2/2009 |
| WO | WO2009/039134 | 3/2009 |
| WO | WO2009/02078 | 4/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/014921 | 2/2010 |
| WO | WO2010/030592 | 3/2010 |
| WO | WO2010043721 | 4/2010 |
| WO | WO2010/084160 | 7/2010 |
| WO | WO2010/099527 | 9/2010 |
| WO | WO/2010/139784 | 12/2010 |
| WO | WO2010/143582 | 12/2010 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2012/034116 | 3/2012 |
| WO | WO2012/107498 | 8/2012 |
| WO | WO2012/013727 | 12/2012 |
| WO | WO2012/013728 | 12/2012 |

OTHER PUBLICATIONS

"Inhibition of lysine-specific demethylase 1 by polyamine analogues results in reexpression of aberrantly silenced genes" Y. Huang (2007) *PNAS* 104 (19), 8023-8028.

"Inhibition of cell growth by EGR-1 in human primary cultures from malignant glioma" A. Calogero (2004) *Cancer Cell Int.* 4.

"Sustained Expression of Early Growth Response Protein-1 Blocks Angiogenesis and Tumor Growth" M. Lucerna (2006) *Cancer Res.* 66, 6708-6713.

"EGR1 Predicts PTEN and Survival in Patients With Non—Small-Cell Lung Cancer" B. Ferraro (2005) *J. Clin. Oncol* 23(9), 1921-1926.

"The lysine-specific demethylase 1 is required for cell proliferation in both p53-dependent and -independent manners". A. Scoumanne (2007) *J. Biol. Chem.* 282, 15471-15475.

"Mutation of Drosophila Lsd1 disrupts H3-K4 methylation, resulting in tissue-specific defects during development". L. Di Stefano (2007) *Curr Biol.* 17(9), 808-12.

"LSD1 demethylates repressive histone marks to promote androgen-receptor-dependent transcription". E. Metzger (2005) *Nature* 437, 436-9.

"2-Substituted Cyclopropylamines. I. Derivatives and Analogs of 2-Phenylcyclopropylamine" Kaiser (1962) *J. Med. Chem.* 5 (6), 1243-1265.

"2-Substituted cyclopropylamines. II. Effects of structure upon monoamine oxidase-inhibitory activity as measured in vivo by potentiation of tryptamine convulsions." Zirkle (1962) *J. Med. Chem.* 5(6), 1265-1284.

"Fluorinated phenylcyclopropylamines. Part 3: Inhibition of monoamine oxidase A and B." S. Yoshida (2004) *Bioorg. Med. Chem.* 12(10), 2645-2652.

"Fluorinated phenylcyclopropylamines. Part 5: Effects of electron-withdrawing or -donating aryl substituents on the inhibition of monoamine oxidases A and B by 2-aryl-2-fluorocyclopropylamines" S. Hruschkaa (2008) *Bioorg. Med. Chem.* 16(15), 7148-7166.

"Monoamine oxidase inhibitors: reappraisal of dietary considerations". D. G. Folks (1983) *J. Clin.Psychopharmacol.* 3(4), 249-52.

"Protein methylation: a new mechanism of p53 tumor suppressor regulation" A. Scoumanne (2008) *Histol Histopathol* 23, 1143-1149.

"Structural Basis for the Inhibition of the LSD1 Histone Demethylase by the Antidepressant trans-2-Phenylcyclopropylamine" M. Yang (2007) *Biochemistry* 46 (27), 8058-8065.

"Crystal structure of histone demethylase LSD1 and tranylcypromine at 2.25 Å" S. Mimasu (2008) *Biochemical and Biophysical Research Communications* 366, 15-22.

"Structural basis of histone demethylation by LSD1 revealed by suicide inactivation" M. Yang (2007) *Nature Structural & Molecular Biology* 14(6), 535-539.

"The lysine demethylase LSD1 (KDM1) is required for maintenance of global DNA methylation" J. Wang (2009) *Nature Genetics* 41(1), 125-129.

"LSD1: oxidative chemistry for multifaceted functions in chromatin Regulation." F. Forneris (2008) *Trends in Biochemical Sciences* 33(4), 181-189.

"Synthesis, Stereochemical Identification, and Selective Inhibitory Activity against Human Monoamine Oxidase-B of 2-Methylcyclohexylidene-(4-arylthiazol-2-yl)hydrazones". Franco Chimenti (2008) *J. Med. Chem.* 51 (16), 4874-4880.

"Lysine-Specific Demethylase I is strongly expressed in poorly differentiated neuroblastoma: implications for therapy". J.H Schulte (2009) *Cancer Res.* 69 (5), 2065-2071.

"Synthesis and structure—activity relationship of 4-(2-arylcyclopropylamino)- quinoline-3-carbonitriles as EGFR tyrosine kinase inhibitors". M. Pannala (2007) *Bioorganic & Medicinal Chemistry Letters* 17 (21), 5978-5082.

"Mechanisms involved in the regulation of histone lysine demethylases". F. Lan, 2008 *Current Opinion in Cell Biology*, 20 316-325.

"Histone demethylase LSD1 is required to induce skeletal muscle differentiation by regulating myogenic factors" J. Choi (2010) *Biochemical and Biophysical Research Communications* 401(3), 327-332.

"Cancer Therapy: Preclinical Novel Oligoamine Analogues Inhibit Lysine-Specific Demethylase 1 and Induce Reexpression of Epigenetically Silenced Genes" Y. Huang (2009) *Clin. Cancer Res.* 15(23), 7217-28.

"Structurally designed trans-2-phenylcyclopropylamine derivatives potently inhibit histone demethylase LSD1/KDM1". S. Mimasu (2010) *Biochemistry* 49 (30), 6494-503.

"Biochemical, Structural, and Biological Evaluation of Tranylcypromine Derivatives as Inhibitors of Histone Demethylases LSD1 and LSD2". C. Binda (2010) *JACS* 132,6827-6833.

"LSD1 Is a Subunit of the NuRD Complex and Targets the Metastasis Programs in Breast Cancer" Y. Wang (2009) *Cell* 138, 660-672.

"(Bis)urea and (Bis)thiourea Inhibitors of Lysine-Specific Demethylase 1 as Epigenetic Modulators" S. K. Sharma (2010) *J. Med. Chem.* 53 (14), 5197-5212.

"Identification of Cell-Active Lysine Specific Demethylase 1-Selective Inhibitors" R. Ueda (2009) *J. Am. Chem Soc* 131(48), 17536-17537.

"N-Substituted derivatives of 2-aminoethanethiol and 2-hydrazinoethanethiol" R.D. Westland 1968 *J Med Chem* 11(4) 824-829.

"Lysine-specific demethylase 1 (LSD1) is highly expressed in ER-negative breast cancers and a biomarker predicting aggressive biology" LIM 2010 *Carcinogenesis* 31(3) 512-520.

"Modulation of breast cancer resistance protein (BCRP/ABCG2) by non-basic chalcone analogues" HAN 2008 *Eur. J. Pharma*35(1-2) 30-41.

"Combinatorial lead optimization of [1,2]-diamines based on ethambutol as potential antituberculosis preclinical candidates" R. E. Lee (2003) *J. Comb. Chem.* 5(2), 172-187.

PCT International Search Report, PCT/EP2010/050697, dated Mar. 19, 2010.

PCT International Search Report and Written Opinion for Application No. PCT/EP2012/070900 dated Jan. 17, 2013.

U.S. Appl. No. 13/877,919, filed Oct. 7, 2011, Cyclopropylamine inhibitors of oxidases.

U.S. Appl. No. 13/876,485, filed Sep. 30, 2011, Selective LSD1 and duel LSD1/MAO-B inhibitors for modulating iseases associated with alterations in protein conformation.

"Synthesis of 5H-dibenzo[a,d]cycloheptene derivatives with diverse biological activities". Arya et al., (1978) Indian J Chem B., 16B, 220-225.

"Enantioselective synthesis of tranylcypromine analogues as lysine demethylase (LSD1) inhibitors". Benelkebir et al., (2011) Bioorg Med Chem, 19, 3709-3716.

"Cyclopropanes and Cyclobutanes. LXVIII. N-Mono and N,N-disubsituted 1-Amino-2- Phenylcyclopropanes". Bolesov et al., (1974) J Organic Chem USSR, 10(6), 1678-84.

"Cyclopropanes and Cyclobutanes. LXIX. Synthesis and Properties of (b-Hydroxyalkylamino)cyclopropanes". Bolesov et al., (1974) Zhournal Organicheskoi Khimii Eng Transl., 10(10), 2122-2128.

Original paper (in Russian) of: "Cyclopropanes and Cyclobutanes. LXVIII. N-Mono and N,N-disubsituted 1-Amino-2-Phenylcyclopropanes". Bolesov et al., (1974) J Organic Chem USSR, 10(6), 1678-84.

"Transdermal delivery of drugs". Brown et al., (1988), Annu Rev Med, 39:221-229.

"N- and O-Alkylation of 3-indolylcyclopropylacetic acid derivatives". Burakova et al., (2002) Russian Chemical Bulletin, 51(10) 1829-1840.

"Polymers for delivering peptides and proteins". Burnham, (1994) Am J Hosp Pharm, 51(2):210-218.

"Recent Advances in the Development of Polyamine Analogues as Antitumor Agents". Casero et al., (2009) J Med Chem, 52(15),4551-4573.

"The Kulinkovich Reaction in the Synthesis of Constrained N,N-Dialkyl Neurotransmitter Analogues". Faler et al., (2007) Organic Letters, 9(10),1987-1990.

"Estimates of the cancer incidence and mortality in Europe in 2006". Ferlay et al., (2007) Ann Oncol, 18(3), 581-92.

"Sustained-release characteristics of a new implantable formulation of disulfiram". Phillips et al., (1984) J Pharm Sci, 73(12):1718-1720.

"Disulfiram implantation: a dose response trial". Wilson et al., (1984) J Clin Psychiatry, 45(6):242-247.

XP-002568777, CHEMCATS Accession No. 2088922753, 2009.

"Comparative analysis of small molecules and histone substrate analogues as LSD1 lysine demethylase inhibitors", JC Culhane et al, JACS 2010,132(9),3164-3176.

"Ticagrelor: a new reversible oral antiplatelet agent" A Khaleel et al, IRJP 2010, 1(1),62-69.

European Search Report for Application No. EP09000790.7 dated Dec. 11, 2009.

European Search Report for Application No. EP09171425.3 dated Mar. 8, 2010.

European Search Report for Application No. EP09172705.7 dated Mar. 11, 2010.

PCT International Preliminary Report on Patentability for Application No. PCT/EP2010/050697 dated Jul. 26, 2011.

PCT International Preliminary Report on Patentability for Application No. PCT/EP2009/63685 dated Apr. 19, 2011.

European Search Report for Application No. EP09165840.1 dated Jan. 18, 2010.

European Search Report for Application No. EP08166973.1 dated Mar. 19, 2009.

European Communication for Application No. EP09736961.5 dated Sep. 21, 2012.

PCT International Preliminary Report on Patentability for Application No. PCT/EP2010/055103 dated Apr. 11, 2012.

PCT International Search Report and Written Opinion for Application No. PCT/EP2010/055103 dated Mar. 3, 2011.

PCT International Search Report and Written Opinion for Application No. PCT/EP2010/055131 dated Oct. 26, 2010.

PCT International Preliminary Report on Patentability for Application No. PCT/EP2010/055131 dated Mar. 27, 2012.

PCT International Preliminary Report on Patentability for Application No. PCT/EP2011/062947 dated Jan. 29, 2013.

PCT International Search Report and Written Opinion for Application No. PCT/EP2011/062947 dated Oct. 6, 2011.

PCT International Search Report and Written Opinion for Application No. PCT/EP2011/056279 dated Aug. 11, 2011.

PCT International Preliminary Report on Patentability for Application No. PCT/EP2011/062949 dated Jan. 29, 2013.

PCT International Search Report and Written Opinion for Application No. PCT/EP2011/062949 dated Nov. 8, 2011.

PCT International Search Report and Written Opinion for Application No. PCT/EP2011/067608 dated Mar. 15, 2012.

PCT International Preliminary Report on Patentability for Application No. PCT/EP2011/056279 dated Oct. 23, 2012.

U.S. Appl. No. 13/812,386, filed Jan. 25, 2013, Matthew Colin Thor Fyfe, Cyclopropylamine Derivatives Useful as LSD1 Inhibitors.

U.S. Appl. No. 13/641,916, filed Dec. 21, 2012, Alberto Ortega Munoz, Lysine Specific Demethylase-1 Inhibitors and Their Use.

U.S. Appl. No. 13/580,553, filed Aug. 22, 2012, lio Cesar Castro Palomino Laria, Inhibitors for Antiviral Use.

U.S. Appl. No. 13/812,366, filed Jan. 25, 2013, Alberto Ortega Munoz, Arylcyclopropylamine Based Demethylase Inhibitors of LSD1 and Their Medical Use.

U.S. Appl. No. 13/580,710, filed Jan. 4, 2013, Jonathan Alleman Baker, Lysine Demethylase Inhibitors for Diseases and Disorders Associated with Hepadnaviridae.

* cited by examiner

OXIDASE INHIBITORS AND THEIR USE

CROSS-REFERENCE TO RELATED APPLICATIONS

This application is a continuation of PCT Patent Application Serial No. PCT/EP2009/063685, filed Oct. 19, 2009, and published in English as International Patent Publication WO2010/043721 on Apr. 22, 2010, which application claims priority to European Patent Application Serial No. EP 08166973.1 filed Oct. 17, 2008, and European Patent Application Serial No. EP 09165840.1, filed Jul. 17, 2009, the entire disclosure of each of which is hereby incorporated herein by this reference in its entirety.

TECHNICAL FIELD

The invention relates to compounds and their use in therapy.

BACKGROUND

Cancer is prevalent: there were about 3.2 million cancer cases diagnosed (53% men, 47% women) and 1.7 million deaths from cancer (56% men, 44% women) in Europe (Ferlay et al. (2007) *Ann. Oncol.* 18(3):581-92). In the United States, the probability of developing invasive cancer is 38% for females and 46% for males that live to be 70 years old and older. In the US about 1.4 million new cases of cancer are expected for 2006. Although the five year survival rate for cancer is now 65%, up from about 50% in the mid-nineteen seventies, cancer is deadly. It is estimated that 565,000 people in the United States will die from cancer in 2006 (American Cancer Society, Surveillance Research, 2006). Despite tremendous advances in cancer treatment and diagnosis, cancer remains a major public health concern. Accordingly, there is a need for new therapeutics with activity in cancer.

Another health crisis is facing industrialized nations. As the population in these countries age, neurodegenerative diseases are affecting more and more people, posing a tremendous economic burden to national health systems. Alzheimer's disease is the largest neurodegenerative disease; disease modifying drugs have long been sought, but to date, none have been identified. Other neurodegenerative conditions include Parkinson's disease, Huntington's disease, Lewy Body dementia, and which are all characterized by disease progression which robs the patients of their ability to perform normal daily activities, eventually leading to death.

One similar characteristic amongst many cancers and neurodegenerative diseases is aberrant gene expression. A number of compounds have been shown to alter gene expression, including histone deacetylase inhibitors which alter the histone acetylation profile of chromatin. Histone deacetylase inhibitors like SAHA, TSA, and many others have been shown to alter gene expression in various in vitro and in vivo animal models. Another modification that is involved in regulating gene expression is histone methylation. Histones can be subject to numerous modifications including lysine and arginine methylation. The methylation status of histone lysines has recently been shown to be important in dynamically regulating gene expression.

A group of enzymes known as histone lysine methyl transfeases and histone lysine demethylases are involved histone lysine modifications. One particular human histone lysine demethylase enzyme called Lysine Specific Demethylase-1 (LSD1) was recently discovered (Shi et al. (2004) *Cell* 119: 941) to be involved in this crucial histone modification. Inactivation of LSD1 in Drosophila (dLSD1) strongly affects the global level of mono and dimethyl-H3-K4 methylation but not methyl-H3K9 while the levels of some other histone methylation and acetylation marks remained the same. dLSD1 inactivation resulted in elevated expression of a subset of genes, including neuronal genes in non-neuronal cells analogous to the functions of LSD1 in human cells. In Drosophila, dLsd1 is not an essential gene, but animal viability is strongly reduced in mutant animals in a gender specific manner (Destefano et al. (2007) *Curr Biol.* 17(9):808-12). Mouse homozygous LSD1 knock-outs were embryonic lethal.

LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. Recent experiments with LSD1 have shown that it is involved in diverse process such as carcinogenesis (Kahl et al. (2006) *Cancer Res.* 66:1341-11347) and vascular inflammation (Reddy et al. (2008) *Circ. Res.* 103:615). It was found that a commercially available antidepressant, Parnate®, which targets monoamine oxidase (MAO), also inhibits LSD1 at clinically relevant concentrations (Lee et al. (2006) *Chem. Biol.* 13:563-567). Schmidt et al. found "$IC_{50}$ values for 2-PCPA of 20.7±2.1 µM for LSD1, 2.3±0.2 µM for MAO A, and 0.95±0.07 µM for MAO B." See Schmidt et al. (2007) *Biochemistry* 46(14)4408-4416. Thus, Parnate® (2-PCPA) is a better inhibitor of MAO-A and MAO-B as compared to LSD1. Schmidt et al. note that the 1050 values for irreversible inhibitors of LSD1 like Parnate® can greatly depend on assay conditions. Additionally, derivatives of Parnate® also can inhibit LSD1 (Gooden et al. (2008) *Bioorg. Med. Chem. Let.* 18:3047-3051). Another class of compounds was recently disclosed to inhibit LSD1 activity: polyamines (Huang et al. (2007) *PNAS* 104:8023-8028). These polyamines inhibit LSD1 modestly and were shown to cause the re-expression of genes aberrantly silenced in cancer cells.

LSD1 is also involved in regulating the methylation of lysines of some proteins which are not histones, like P53 and DNMT1 which both have critical roles in cancer.

Lee et al. ((2006) *Chem. Biol.* 13:563-567) reported that tranylcypromine inhibits histone H3K4 demethylation and can derepress Egr1 gene expression in some cancer lines. A body of evidence is accumulating that Egr-1 is a tumor suppressor gene in many contexts. Calogero et al. ((2004) *Cancer Cell International* 4:1) reported that Egr-1 is down-regulated in brain cancers and exogenous expression of Egr-1 resulted in growth arrest and eventual cell death in primary cancer cell lines. Lucerna et al. ((2006) *Cancer Research* 66, 6708-6713) showed that sustained expression of Egr-1 causes antiangiogeneic effects and inhibits tumor growth in some models. Ferraro et al. ((2005) *J Clin Oncol.* March 20; 23(9):1921-6) reported that Egr-1 is down-regulated in lung cancer patients with a higher risk of recurrence and may be more resistant to therapy. Scoumanne et al. ((2007) *J Biol Chem.* May 25; 282(21):15471-5) observed that LSD1 is required for cell proliferation. They found that deficiency in LSD1 leads to a partial cell cycle arrest in G2/M and sensitizes cells to growth suppression induced by DNA damage. Kahl et al. ((2006) *Cancer Res.* 66(23):11341-7) found that LSD1 expression is correlated with prostate cancer aggressiveness. Metzger et al. ((2005) *Nature* 15; 437(7057):436-9) reported that LSD1 modulation by siRNA and pargyline regulates androgen receptor (AR) and may have therapeutic potential in cancers where AR plays a role, like prostate, testis, and brain cancers.

Thus, a body of evidence has implicated LSD1 in a number of cancers, which suggests that LSD1 is a therapeutic target for cancer.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365,458; 3,471,522; 3,532,749) have disclosed the synthesis and activity of a number of phenylcyclopropylamine related compounds. Zirkle et al. ((1962) *J. Med. Chem.* 1265-1284) reported that mono- and disubstitution of the amino group of trans-2-phenylcyclopropylamine with methyl decreases the activity only slightly whereas monosubstitution with larger groups like alkyl and araalkyl groups results in considerable loss of activity in the tryptamine potentiation assay for MAO activity. Studies have also been conducted with phenylcyclopropylamine related compounds to determine selectivity for MAO-A versus MAO-B since MAO-A inhibitors can cause dangerous side-effects (see e.g., Yoshida et al. (2004) *Bioorg. Med Chem.* 12(10):2645-2652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63). Other phenylcyclopropylamine type compounds are disclosed in Bolesov et al. ((1974) *Zhurnal Organicheskoi Khimii* 10:8 1661-1669) and Russian Patent No. 230169 (19681030). Gooden et al. ((2008) *Bioorg. Med. Chem. Let.* 18:3047-3051) describe the synthesis of phenylcyclopropylamines derivatives and analogs as well as their activity against MAO-A, MAO-B, and LSD1. None of the compound made in Gooden et al. showed a lower Ki for LSD1 as compared to either MAO A or MAO B. Additionally, most of the Gooden et al. phenylcyclopropylamine derivatives were better inhibitors of MAO-A as compared to MAO-B.

Lee et al. ((2003) *J. Comb. Chem.* 5:172-187, and related patent references including US patent publication no. 2006148904 and WO2007005896) disclose the lead optimization of [1,2]diamines as potential antituberculosis preclinical candidates. Some studies have used the phenylcyclopropylamine moiety as a reagent to functionalize specific chemical cores (or scaffolds). For example, WO publication no.: WO 2004/062601 (PCT/US2004/000433 filed Jan. 8, 2004) discloses methods for inhibiting gram-negative bacterial infections with UDP-3-O—(R-3-hydroxydecanoyl)-N-acetylglucosamine deacteylase inhibitors, WO 2007/025709 (PCT/EP2006/008426 filed Aug. 29, 2006) discloses diamines, US patent application publication no. US2006/0287287 (published Dec. 21, 2006) discloses aminoacetamide acyl guanidines for inhibiting beta-secreatse, US patent application publication no. US2006/0275366 (published Dec. 7, 2006) discloses controlled release formulations for treating diseases and disorders associated with hepatitis C by inhibiting HCV proteases, and disease associated with cathespin, US patent application publication no. US2005/0009832 (Jan. 13, 2005) discloses 8-amino-aryl-substituted imidazopyrazines as kinase inhibitors.

In view of the lack of adequate treatments for conditions such as cancer, there is a desperate need for disease modifying drugs and drugs that work by inhibiting novel targets. There is a need for the development of LSD1 selective inhibitors particularly those which selectively inhibit LSD1.

DISCLOSURE

The present invention relates to the identification of compounds and their use in treating and/or preventing diseases. The present invention provides compounds of Formula I, pharmaceutical compositions comprising a compound of Formula I and a pharmaceutically acceptable carrier, and their use for treating diseases. One use of the compounds of Formula I is for treating cancer. Another use for the compounds of Formula I are to inhibit LSD1. Compounds of Formula I can have monoamine oxidase inhibition activity and therefore can be used to treat diseases like depression and Parkinson's disease as well as other neurodegenerative conditions.

In one embodiment, the invention provides a compound of Formula I or a pharmaceutically acceptable salt thereof:

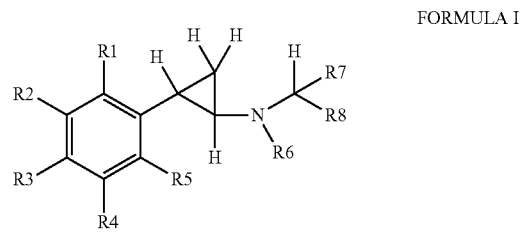

FORMULA I wherein
each R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is chosen from —C(=O)NR$_x$R$_y$, and —C(=O)R$_z$;
R$_x$ when present is chosen from —H, alkyl, alkynyl, alkenyl, -L-carbocyclyl, -L-aryl, and -L-heterocyclyl, all of which are optionally substituted (except —H);
R$_y$ when present is chosen from —H, alkyl, alkynyl, alkenyl, -L-carbocyclyl, -L-aryl, and -L-heterocyclyl, all of which are optionally substituted (except —H);
R$_z$ when present is chosen from —H, alkoxy, -L-carbocyclyl, -L-heterocyclyl, -L-aryl, wherein the aryl, heterocyclyl, or carbocyclyl are optionally substituted;
each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—; —(CH$_2$)$_n$C(=O)NH(CH$_2$)$_n$—; —(CH$_2$)$_n$NHC(=O)O(CH$_2$)$_n$—, —(CH$_2$)$_n$NHC(=O)NH(CH$_2$)$_n$—, —(CH$_2$)$_n$ NHC(=S)S(CH$_2$)$_n$—; —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)NH(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a more specific aspect of this embodiment, the optional substituents are 1 or 2 optional substituents chosen from halo, alkyl, aryl, and arylalkyl.

Unless otherwise specified each L and each n in a molecule is independently chosen and can be in either orientation, e.g., —(CH$_2$)$_n$NHC(=S)S(CH$_2$)$_n$—, refers to phenylcyclopropylamine-(CH$_2$)$_n$NHC(=S)S(CH$_2$)$_n$-heterocyclyl and phenylcyclopropylamine—(CH$_2$)$_n$SC(=S)NH(CH$_2$)$_n$-heterocyclyl orientations.

In one aspect of this embodiment, each L is independently chosen from —(CH$_2$)$_n$—NH(CH$_2$)$_n$—, —(CH$_2$)$_n$O (CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, if present, R$_x$, R$_y$, and/or R$_z$ have from 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a more specific aspect of this embodiment, if present, R$_x$, R$_y$, and/or R$_z$ have from 1-4 optional substituents independently chosen from alkyl, alkenyl, alkynyl, amino, aryl, arylalkyl, arylalkenyl, arylalkynyl, arylalkoxy, aryloxy, halo, and cyano. In a more specific aspect of this embodiment, the optional substituent is 1 optional substituent chosen from halo, alkyl, aryl, and arylalkyl.

In one aspect of this embodiment, if present, R$_x$ and/or R$_y$ are independently chosen from —H, alkyl, alkynyl, alkenyl, and -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano.

In another aspect of this embodiment, if present, R$_z$ is an optionally substituted heterocyclyl (i.e., -L-heterocyclyl where -L- is a bond). In a more specific aspect of this embodiment, the optionally substituted heterocyclyl has 1-4 optional substituents independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has one substituent which is chosen from alkyl and arylalkyl.

In a preferred aspect of this embodiment, when R$_x$ and R$_y$ are present, one of R$_x$ and R$_y$ is hydro and the other of R$_x$ and R$_y$ is chosen from alkyl, alkynyl, alkenyl, -L-carbocyclyl, all of which are optionally substituted (except —H). In an even more specific preferred aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano.

In yet another preferred aspect of this embodiment, one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, and cyano. In a more specific preferred aspect, R1, R5, R6 and R7 are each hydro.

In one aspect of this embodiment, the invention provides a compound of Formula I wherein R3 is an optionally substituted aryl group having from 1-4 optional substituents. In a more specific aspect, R3 is an optionally substituted phenyl group and the 1-4 optional substituents are independently chosen from halo, alkyl, alkoxy, haloalkyl, haloalkoxy, sulphonyl, and cyano. In a more specific aspect, R3 is an optionally substituted phenyl group which has 1 or 2 optional substituents independently chosen from halo, alkyl, alkoxy, haloalkyl, haloalkoxy, sulphonyl, and cyano.

In one aspect of this embodiment, the invention provides a compound Formula I, wherein R3 is an optionally substituted arylalkoxy group having from 1-4 optional substituents. In a more specific aspect, R3 is an optionally substituted benzyloxy group and the 1-4 optional substituents are independently chosen from halo, alkyl, alkoxy, haloalkyl, haloalkoxy, sulphonyl, and cyano. In a more specific aspect, R3 is an optionally substituted benzyloxy group which has 1 or 2 optional substituents independently chosen from halo, alkyl, alkoxy, haloalkyl, haloalkoxy, sulphonyl, and cyano.

In one embodiment, the invention provides a compound of Formula I or a pharmaceutically acceptable salt thereof wherein:
  each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
  R6 is chosen from —H and C1-C6 alkyl;
  R7 is chosen from —H, alkyl, and cycloalkyl;
  R8 is —C(=O)NR$_x$R$_y$;
  R$_x$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
  R$_y$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
  each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)N(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and —(CH$_2$)$_n$NHC(=S)N(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_x$ and R$_y$ have from 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, R$_x$ and/or R$_y$ are independently chosen from —H, alkyl, alkynyl, alkenyl, -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect, R$_x$ and R$_y$ do not have optional substituents.

In a preferred aspect of this embodiment, one of R$_x$ and R$_y$ is hydro and the other of R$_x$ and R$_y$ is chosen from alkyl, alkynyl, alkenyl, -L-carbocycle, all of which are optionally substituted (except —H). In an even more specific preferred aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect, R$_x$ and R$_y$ do not have optional substituents.

In yet another preferred aspect of this embodiment one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, and cyano. In a more specific preferred aspect, R1, R5, R6 and R7 are each hydro.

In one embodiment, the invention provides a compound of Formula I or a pharmaceutically acceptable salt thereof wherein:

each of R1-R5 is optionally substituted and independently chosen from hydro, hydroxyl, halo, alkyl, alkenyl, alkynyl, alkoxy, arylalkyl, arylalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;

R6 is chosen from —H and C1-C6 alkyl;

R7 is chosen from —H, alkyl, and cycloalkyl;

R8 is —C(=O)NR$_x$R$_y$;

R$_x$ is chosen from —H, C1-C6 alkyl, C2-C6 alkynyl, C2-C6 alkenyl, -L-carbocyclyl, -L-aryl, -L-heterocyclyl, all of which are optionally substituted (except —H);

R$_y$ is chosen from —H, C1-C6 alkyl, C2-C6 alkynyl, C2-C6 alkenyl, -L-carbocyclyl, -L-aryl, -L-heterocyclyl, all of which are optionally substituted (except —H);

each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)N(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CF$_{12}$)$_n$S(CH$_2$)$_n$—, and —(CH$_2$)$_n$NHC(=S)NH(CH$_2$)$_n$—, where each n is independently chosen from 0, 1, 2, 3, 4, 5, 6, 7, and 8; and pharmaceutically acceptable salts thereof.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_x$ and R$_y$ have 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, $R_x$ and/or $R_y$ are independently chosen from —H, alkyl, alkynyl, alkenyl, -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect of this embodiment, $R_x$ and $R_y$ do not have substituents.

In a preferred aspect of this embodiment, one of $R_x$ and $R_y$ is hydro and the other of $R_x$ and $R_y$ is chosen from alkyl, alkynyl, alkenyl, -L-carbocyclyl, all of which are optionally substituted (except —H). In an even more specific preferred aspect, the 1-4 optional substituents are independently chosen from alkyl, alkenyl, alkynyl, amino, aryl, arylalkyl, arylalkenyl, arylalkynyl, arylalkoxy, aryloxy, halo, and cyano. In one preferred aspect, $R_x$ and $R_y$ do not have substituents.

In one embodiment, the invention provides a compound of Formula I or a pharmaceutically acceptable salt thereof wherein:
  each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
  R6 is chosen from —H and C1-C6 alkyl;
  R7 is chosen from —H, alkyl, and cycloalkyl;
  R8 is —C(=O)$R_z$;
  $R_z$ is chosen from —H, C1-C6 alkoxy, -L-carbocyclyl, -L-heterocyclyl, and -L-aryl, all of which are optionally substituted (except —H);
  each L is a linker that links the main scaffold of Formula I to a carbocyclyl, heterocyclyl, or aryl group, wherein the hydrocarbon portion of the linker -L- can be saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O (CH$_2$)$_n$—, —(CH$_2$)$_n$NHC(=O)NH(CH$_2$)$_n$—, —(CH$_2$)$_n$ NHC(=S)S(CH$_2$)$_n$—, —(CH$_2$)$_n$OC(=O)S (CH$_2$)$_n$—, —(CH$_2$)$_n$NH(CH$_2$)$_n$—, —(CH$_2$)$_n$O (CH$_2$)$_n$—, —(CH$_2$)$_n$S(CH$_2$)$_n$—, and —(CH$_2$)$_n$NHC (=S)NH(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2 and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, $R_z$ is optionally substituted with 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In another aspect of this embodiment, $R_z$ is an optionally substituted heterocyclyl (i.e., -L-heterocyclyl where -L- is a bond). In a more specific aspect of this embodiment, the optionally substituted heterocyclyl has 1-4 optional substituents which are independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has 1 optional substituent which is chosen from alkyl and arylalkyl.

In yet another preferred aspect of this embodiment one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, and cyano. In a more specific preferred aspect, R1, R5, R6 and R7 are each hydro.

In one embodiment, the invention provides a compound of Formula I or a pharmaceutically acceptable salt thereof wherein:
  each of R1-R5 is optionally substituted and independently chosen from hydro, hydroxyl, halo, alkyl, alkenyl, alkynyl, alkoxy, arylalkyl, arylalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;
  R6 is chosen from —H and C1-C6 alkyl;
  R7 is chosen from —H, alkyl, and cycloalkyl;
  R8 is —C(=O)$R_z$;
  $R_z$ is chosen from —H, -L-carbocyclyl, -L-heterocyclyl, -L-aryl, wherein the aryl, heterocyclyl, or carbocycle is optionally substituted;
  each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and —(CH$_2$)$_n$NHC(=S)NH(CH$_2$)$_n$—, where each n is independently chosen from 0, 1, 2, 3, 4, 5, 6, 7, and 8; and pharmaceutically acceptable salts thereof.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_z$ is optionally substituted with 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In another aspect of this embodiment, R$_z$ is an optionally substituted heterocyclyl (i.e., -L-heterocyclyl where -L- is a bond). In a more specific aspect of this embodiment, the optionally substituted heterocyclyl has 1-4 optional substituents which are independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has 1 optional substituent which is chosen from alkyl and arylalkyl.

In yet another preferred aspect of this embodiment one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, and cyano. In a more specific preferred aspect, R1, R5, R6 and R7 are each hydro.

In one preferred embodiment, the invention provides a compound of Formula I(a), a pharmaceutical composition comprising a compound of Formula I(a) and a pharmaceutically acceptable carrier, and/or methods for treating diseases by administering to an individual a pharmaceutical composition comprising a compound of Formula I(a). The compounds of Formula I(a) are a sub-group of the compounds of Formula I wherein R6 is hydro and R8 is —(C=O)R$_z$ and the other variables are as defined below in the following embodiments and aspects of the embodiments.

Thus, in a preferred embodiment, the invention provides a compound of Formula I(a) or a pharmaceutically acceptable salt thereof

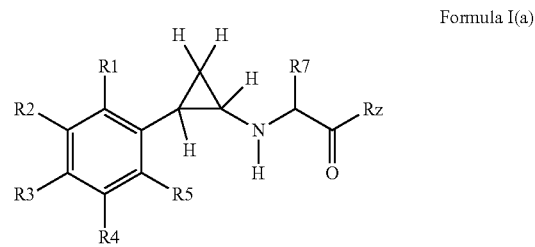

Formula I(a)

wherein

R1 is chosen from hydro, halo, C1-C6 alkyl, C1-C6 alkoxy, C1-C6 haloalkyl, C1-C6 haloalkoxy, and cyano;

one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and wherein the aryl or heterocyclyl moiety of the -L-aryl and -L-heterocyclyl group is optionally substituted with one group chosen from halo, C1-C6 alkyl, C1-C6 alkoxy, C1-C6 haloalkyl, C1-C6 haloalkoxy, and cyano;

and the others of R2, R3, and R4 are independently chosen from hydro, halo, C1-C6 alkyl, C1-C6 alkoxy, C1-C6 haloalkyl, C1-C6 haloalkoxy, cyano, and amino;

R5 is chosen from hydro, halo, C1-C6 alkyl, C1-C6 alkoxy, C1-C6 haloalkyl, C1-C6 haloalkoxy, and cyano;

R7 is chosen from hydro, C1-C6 alkyl, fluoro, alkoxy, and cyano;

R$_z$ is -L-heterocyclyl which is optionally substituted with from 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido, and wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3.

In a specific aspect of this embodiment, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In a more specific aspect of this embodiment, the invention provides a compound of Formula I(a) wherein the optional substituents on the heterocyclyl of Rz are independently chosen from alkyl, alkenyl, amino, aryl, arylalkyl, arylalkenyl, arylalkynyl, arylalkoxy, and aryloxy. In an even more specific aspect, the heterocyclyl of R$_z$ has one optional substituent which is chosen from alkyl and arylalkyl.

In an even more specific aspect, the invention provides a compound of Formula I(a) wherein the optional substituents on the ring system of R$_z$ are independently chosen from C1-C6 alkyl and arylalkyl wherein the alkyl moiety of the arylalkyl group is a C1-C6 alkyl.

In one aspect of this embodiment, the invention provides a compound of Formula I(a) wherein:
R1 and R5 are hydro;
one of R2, R3, and R4 is chosen an -L-aryl group wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; wherein the aryl moiety of the -L-aryl group is optionally substituted with one group chosen from halo, C1-C6 alkyl, C1-C6 alkoxy, C1-C6 haloalkyl, C1-C6 haloalkoxy, and cyano;
R7 is hydro;
R$_z$ is an -L-heterocyclyl group wherein the heterocyclyl is optionally substituted with 1-4 optional substituents and the heterocyclyl group is chosen from morpholino, piperidyl, piperazinyl, pyrrolidinyl, thiomorpholino, homopiperazinyl, imidazolyl, imidazolidinyl, pyrazolidinyl, dioxanyl and dioxolanyl, and the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and (CH$_2$)$_n$S(CH$_2$)$_n$—, wherein each n is independently chosen from 0, 1, 2, and 3; o a pharmaceutically acceptable salts thereof.

In a more specific aspect of this embodiment, the invention provides compounds of Formula I(a) wherein the R$_z$ is an -L-heterocyclyl group wherein the -L- is a bond and the heterocyclyl is optionally substituted with 1-4 optional substituents and the heterocyclyl group is chosen from morpholino, piperidinyl, piperizinyl, and pyrrolidinyl. In an even more specific aspect of this embodiment, the 1-4 optional are independently chosen from alkyl, alkenyl, amino, aryl, arylalkyl, arylalkenyl, arylalkynyl, arylalkoxy, and aryloxy. In yet an even more specific aspect of the heterocyclic group is chosen from morpholino, piperidinyl, piperizinyl, and pyrrolidinyl and the heterocyclyl has 1 optional substituent chosen from alkyl and arylalkyl.

In one aspect of this embodiment, -L- is —(CH$_2$)$_n$, —(CH$_2$)$_n$— or (CH$_2$)$_n$O(CH$_2$)$_n$, where each n is independently chosen from 0, 1, 2, and 3.

In one aspect of this embodiment, the invention provides a compound of Formula I(a) or a pharmaceutically acceptable salt thereof
wherein
R1 and R5 are hydro;
one of R2, R3, and R4 is chosen from -L-aryl and -L-heterocyclyl wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are hydro, and wherein the aryl or heterocyclyl moeity of the -L-aryl and -L-heterocyclyl group is optionally substituted with one group chosen from halo, C1-C6 alkyl, C1-C6 alkoxy, C1-C6 haloalkyl, C1-C6 haloalkoxy, and cyano;
R7 is hydro;
R$_z$ is a heterocyclyl group (the -L- of -L-heterocyclyl is a bond) wherein the heterocyclyl is optionally substituted with 1-4 optional substituents and the heterocyclyl group is chosen from morpholino, piperidyl, piperazinyl, pyrrolidinyl, homopiperazinyl; or a pharmaceutically acceptable salt thereof.

In one aspect of this embodiment, the invention provides a compound of Formula I(a) wherein:
R1 and R2 are hydro;
R3 is -L-aryl wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are hydro, and wherein the aryl moiety of the -L-aryl group is optionally substituted with one group chosen from halo, C1-C6 alkyl, C1-C6 alkoxy, C1-C6 haloalkyl, C1-C6 haloalkoxy, and cyano;
R4 and R5 are hydro;
R7 is hydro;
R$_z$ is a heterocyclyl group (i.e., the -L- of -L-heterocyclyl is a bond) wherein the heterocyclyl is optionally substituted with 1-4 optional substituents and the heterocyclyl group is chosen from morpholino, piperidyl, piperazinyl, pyrrolidinyl, homopiperazinyl; or a pharmaceutically acceptable salts thereof.

In an even more specific aspect, the optionally substituted heterocyclyl has one optional substituent chosen from alkyl and arylalkyl.

In one aspect of this embodiment, the invention provides a compound of Formula I(a) wherein R3 is an optionally substituted aryl group having from 1-4 optional substituents. In a more specific aspect, R3 is an optionally substituted phenyl group and the 1-4 optional substituents are chosen from halo, alkyl, alkoxy, haloalkyl, haloalkoxy, sulphonyl, and cyano. In a more specific aspect, R3 is an optionally substituted phenyl group which has 1 or 2 optional substituents chosen from halo, alkyl, alkoxy, haloalkyl, haloalkoxy, sulphonyl, and cyano.

In one aspect of this embodiment, the invention provides a compound Formula I(a) wherein R3 is an optionally substituted arylalkoxy group having from 1-4 optional substituents. In a more specific aspect, R3 is an optionally substituted benzyloxy group and the 1-4 optional substituents are chosen from halo, alkyl, alkoxy, haloalkyl, haloalkoxy, sulphonyl, and cyano. In a more specific aspect, R3 is an optionally substituted benzyloxy group which has 1 or 2 optional substituents independently chosen from halo, alkyl, alkoxy, haloalkyl, haloalkoxy, sulphonyl, and cyano.

In one embodiment, the invention provides a method of treating and/or preventing a disease or condition comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a disease or condition. In a related aspect, the invention provides for the use of a compound of Formula I for the manufacture of a medicament for treating and/or preventing a disease or condition. In a more specific aspect of this embodiment, the compound of Formula I is a compound of Formula I(a) as defined above.

In one embodiment, the invention provides a method of treating and/or preventing cancer comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing cancer. In a related aspect, the invention provides for the use of a compound of Formula I for the manufacture of a medicament for treating and/or preventing cancer. In specific a specific aspect of the embodiments of this paragraph, the cancer is chosen from breast cancer, colorectal cancer, lung cancer, prostate cancer, testicular cancer, and brain cancer. In a more specific aspect of this embodiment, the compound of Formula I is a compound of Formula I(a) as defined above.

In one embodiment, the invention provides a method of inhibiting LSD1 activity comprising administering, to a patient in need of treatment, an amount of a composition comprising a compound of Formula I and a pharmaceutically acceptable carrier sufficient to inhibit LSD1 activity. In one aspect of this embodiment, the invention provides a compound of Formula I for use in inhibiting LSD1. In a related aspect, the invention provides for the use of a compound of Formula I for the manufacture of a medicament for inhibiting LSD1. In a more specific aspect of this embodiment, the compound of Formula I is a compound of Formula I(a) as defined above.

In one embodiment, the invention provides a method of inhibiting monoamine oxidase activity comprising administering, to a patient in need of treatment, an amount of a composition comprising a compound of Formula I and a pharmaceutically acceptable carrier sufficient to inhibit monoamine oxidase activity. In a related embodiment, the invention provides a compound of Formula I for use in treating Parkinson's disease and/or depression. In another related embodiment, the invention provides for the use of a compound of Formula I for the manufacture of a medicament for inhibiting monoamine oxidase. In one specific aspect of this embodiment, the monoamine oxidase is MAO-B. In a more specific aspect of this embodiment, the compound of Formula I is a compound of Formula I(a) as defined above.

In one embodiment, the invention provides a method of treating and/or preventing a neurodegenerative disease or disorder comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition. In a more specific aspect of this embodiment, the compound of Formula I is a compound of Formula I(a) as defined above.

The invention provides in some embodiments a pharmaceutical composition comprising a pharmaceutically acceptable carrier and a compound of Formula I which is selective inhibitors of LSD1. LSD1 selective inhibitors inhibit LSD1 to a greater extant than MAO-A and/or MAO-B. Preferably, LSD1 selective inhibitors have IC50 values for LSD1 which are at least 2-fold lower than the IC50 value for MAO-A and/or MAO-B. In one aspect of this embodiment, the LSD1 IC50 value is at least 5-fold lower than the IC50 value for MAO-A and/or MAO-B. In one aspect of this embodiment, the LSD1 IC50 value is at least 10-fold lower than the IC50 value for MAO-A and MAO-B. In one aspect of this embodiment, the pharmaceutical composition comprising an LSD1 selective inhibitor and a pharmaceutically acceptable salt thereof is useful for treating and/or preventing a disease in an individual. In a more specific, the disease is cancer. In an even more specific aspect, the disease is a cancer is chosen from colorectal, breast, brain, prostate, lung, and testicular cancer. In one specific aspect, the cancer is colorectal cancer. In one specific aspect, the cancer is breast cancer. In one specific aspect, the cancer is brain cancer. In one specific aspect, the cancer is prostate cancer. In one specific aspect, the cancer is lung cancer. In one specific aspect, the cancer is testicular cancer. In a more specific aspect of this embodiment, the compound of Formula I is a compound of Formula I(a) as defined above.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to the identification of compounds and their use in treating and/or preventing diseases. The present invention provides compounds of Formula I, pharmaceutical compositions comprising a compound of Formula I and a pharmaceutically acceptable carrier, and their use for treating diseases. One use of the compounds of Formula I is for treating cancer. Compounds of the invention are amine oxidase inhibitors. Compounds of the invention are particularly potent inhibitors of an amine oxidase known as Lysine Specific Demethylase 1 or LSD1, which is a therapeutically relevant target. Compounds of the invention also inhibit monoamine oxidases, and can therefore be used for disease in which monoamine oxidase inhibition is useful. The compounds of Formula I can be used as LSD1 selective inhibitors that inhibit LSD1 to a greater extent than MAO-A and/or MAO-B. In particular it was found that phenylcyclopropylamine derivatives of Formula I are compounds with unexpectedly potent LSD1 inhibition. For example, most of the compounds of Formula I in Table 1 of the examples have Ki (IC50) values for LSD1 inhibition under 10 micromolar which makes them more potent than tranylcypromine for LSD1 inhibition. Furthermore, many of the compounds of Table 1 have Ki (IC50) values for LSD1 inhibition of under 1 micromolar which makes them at least 20 to 30 fold more potent than tranylcypromine. Surprisingly, some groups of compounds of this series have been found to have IC50 values for LSD1 inhibition around or below 100 nanomolar. These compounds are LSD1 selective in that the inhibit LSD1 to an extent greater than they inhibit MAO-A and/or MAO-B.

In one embodiment, the invention provides a compound of Formula I or a pharmaceutically acceptable salt thereof:

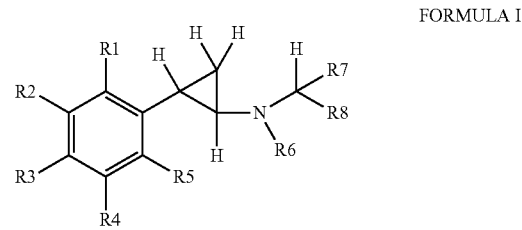

FORMULA I wherein
- each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
- R6 is chosen from —H and alkyl;
- R7 is chosen from —H, alkyl, and cycloalkyl;
- R8 is chosen from —C(=O)NR$_x$R$_y$ and —C(=O)R$_z$;
- R$_x$ is chosen from —H, alkyl, alkynyl, alkenyl, -L-carbocyclyl, -L-aryl, and -L-heterocyclyl, all of which are optionally substituted (except —H);
- R$_y$ is chosen from —H, alkyl, alkynyl, alkenyl, -L-carbocyclyl, -L-aryl, and -L-heterocyclyl, all of which are optionally substituted (except —H);
- R$_z$ is chosen from —H, alkoxy, -L-carbocyclyl, -L-heterocyclyl, -L-aryl, wherein the aryl, heteroaryl, heterocyclyl, or carbocyclyl are optionally substituted;
- each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and (CH$_2$)$_n$NHC(=S)NH(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a more specific aspect of this embodiment, the optional substituent is 1 or 2 optional substituents chosen from halo, alkyl, aryl, and arylalkyl. In a related aspect, the invention provides pharmaceutical compositions comprising a compound as defined in this paragraph and a pharmaceutically acceptable carrier. In yet another related aspect, the pharmaceutical composition, as described above, is used for treating and/or preventing cancer.

Unless otherwise specified each L and each n in a molecule is independently chosen and is in either orientation, e.g., —(CH$_2$)$_n$NHC(=S)S(CH$_2$)$_n$—, refers to phenylcyclopropylamine-(CH$_2$)$_n$NHC(=S)S(CH$_2$)$_n$-heterocyclyl and phenylcyclopropylamine—(CH$_2$)$_n$SC(=S)NH(CH$_2$)$_n$-heterocyclyl orientations.

A preferred configuration around the cyclopropyl ring of the phenylcyclopropylamine derivatives of this embodiment is trans.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, if present, R$_x$, R$_y$, and/or R$_z$ have from 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a more specific aspect of this embodiment, if present, R$_x$, R$_y$, and/or R$_z$ have from 1-4 optional substituents independently chosen from alkyl, alkenyl, alkynyl, amino, aryl, arylalkyl, arylalkenyl, arylalkynyl, arylalkoxy, aryloxy, halo, and cyano. In a more specific aspect of this embodiment, the optional substituent is 1 optional substituent chosen from halo, alkyl, aryl, and arylalkyl.

In one aspect of this embodiment, if present, R$_z$ and/or R$_y$ are independently chosen from —H, alkyl, alkynyl, alkenyl, and -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano.

In another aspect of this embodiment, if present, R$_z$ is an optionally substituted heterocyclyl (i.e., -L-heterocyclyl where -L- is a bond). In a more specific aspect of this embodiment, the optionally heterocyclyl has 1-4 optional substituents independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has 1 optional substituent which is chosen from alkyl and arylalkyl.

In a preferred aspect of this embodiment, when R$_x$ and R$_y$ are present, one of R$_x$ and R$_y$ is hydro and the other of R$_x$ and R$_y$ is chosen from alkyl, alkynyl, alkenyl, -L-carbocyclyl, all of which are optionally substituted (except —H). In an even more specific preferred aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano.

In yet another preferred aspect of this embodiment, one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, cyano, and amino. In a more specific preferred aspect, R1, R5, R6 and R7 are each hydro.

In one aspect of this embodiment, the invention provides a compound of Formula I wherein R3 is an optionally substituted aryl group having from 1-4 optional substituents. In a more specific aspect, R3 is an optionally substituted phenyl group and the 1-4 optional substituents are independently chosen from halo, alkyl, alkoxy, haloalkyl, haloalkoxy, sulphonyl, and cyano. In a more specific aspect, R3 is an optionally substituted phenyl group which has 1 or 2 optional substituents independently chosen from halo, alkyl, alkoxy, haloalkyl, haloalkoxy, sulphonyl, and cyano.

In one aspect of this embodiment, the invention provides a compound Formula I, wherein R3 is an optionally substituted arylalkoxy group having from 1-4 optional substituents. In a more specific aspect, R3 is an optionally substituted benzyloxy group and the 1-4 optional substituents are independently chosen from halo, alkyl, alkoxy, haloalkyl, haloalkoxy, sulphonyl, and cyano. In a more specific aspect, R3 is an optionally substituted benzyloxy group which has 1 or 2 optional substituents independently chosen from halo, alkyl, alkoxy, haloalkyl, haloalkoxy, sulphonyl, and cyano.

In one aspect of this embodiment, each of R1-R5 is independently chosen from —H, halo, C1-C4 alkyl, C—C4 alkoxyl, C1-C4 haloalkyl, —OCH$_2$(phenyl), and C1-C4 haloalkoxy. In a more specific aspect, each of R1-R5 is independently chosen from —H, halo, —OCH$_2$(phenyl) and —CF$_3$. In a more specific aspect each of R1-R5 is —H.

In another aspect of this embodiment, R6 is —H or a C1-C4 alkyl. In a more specific aspect, R6 is —H.

In yet another aspect of this embodiment, R7 is —H or a C1-C4 alkyl. In a more specific aspect, R7 is —H.

In another aspect of this embodiment, each L is chosen from a bond, —CH$_2$—, —CH$_2$CH$_2$—, and —CH$_2$CH$_2$CH$_2$—. In a more specific aspect, L is chosen from a bond and —CH$_2$—.

In another aspect of this embodiment, R$_x$ if present, is chosen from —C1-C6 alkyl, C2-C6 alkenyl, C2-C6 alkynyl, -L-cycloalkyl, -L-aryl, -L-heterocyclyl, wherein the cycloalkyl, aryl, and heterocyclyl is optionally substituted. In a more specific aspect, R$_x$ is chosen from —H, —CH(CH$_3$)$_2$, —C(CH$_3$)$_3$, —CH$_2$CH=CH$_2$, cyclopropyl, cyclobutyl, cyclopentyl, cyclohexyl, and —CH$_2$(phenyl) wherein the cycloalkyl and phenyl group are optionally substituted.

In another aspect of this embodiment, R$_y$ if present, is chosen from C1-C6 alkyl, C2-C6 alkenyl, C2-C6 alkynyl, -L-cycloalkyl, -L-aryl, -L-heterocyclyl, wherein the cycloalkyl, aryl, and heterocyclyl are optionally substituted. In a more specific aspect, R$_y$ is chosen from —H, —CH(CH$_3$)$_2$, —C(CH$_3$)$_3$, —CH$_2$C≡CH, —CH$_2$CH=CH$_2$, cyclopropyl, cyclobutyl, cyclopentyl, cyclohexyl, and —CH$_2$(phenyl), wherein the cycloalkyl and phenyl group are optionally substituted.

In another aspect of this embodiment, z, if present, is an optionally substituted -L-heterocyclyl. In a more specific aspect, R$_z$ is optionally substituted and chosen from N-methylpiperazinyl, morpholinyl, and piperidinyl. In a more specific aspect, R$_z$ is chosen from N-methylpiperazinyl, morpholinyl, and piperidinyl.

In one embodiment, the invention provides a compound of Formula I or a pharmaceutically acceptable salt thereof wherein:
each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
R6 is chosen from —H and C1-C6 alkyl;
R7 is chosen from —H, alkyl, and cycloalkyl;
R8 is —C(=O)NR$_x$R$_y$;
R$_x$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
R$_y$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)N(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)N(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a related aspect, the invention provides pharmaceutical compositions comprising a compound as defined in this paragraph and a pharmaceutically acceptable carrier. In yet another related aspect, the pharmaceutical composition, as described above, can be used for treating and/or preventing cancer.

A preferred configuration around the cyclopropyl ring of the phenylcyclopropylamine derivatives of this embodiment is trans.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_x$ and R$_y$ have from 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, $R_x$ and/or $R_y$ are independently chosen from —H, alkyl, alkynyl, alkenyl, -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect, $R_x$ and $R_y$ do not have substituents.

In a preferred aspect of this embodiment, when $R_x$ and $R_y$ are present one of $R_x$ and $R_y$ is hydro and the other of $R_x$ and $R_y$ is chosen from alkyl, alkynyl, alkenyl, -L-carbocycle, all of which are optionally substituted (except —H). In an even more specific preferred aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect, $R_x$ and $R_y$ do not have substituents.

In yet another preferred aspect of this embodiment one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, cyano, and amino. In a more specific preferred aspect, R1, R5, R6 and R7 are each hydro.

In one aspect of this embodiment, each of R1-R5 is independently chosen from —H, halo, C1-C4 alkyl, C—C4 alkoxyl, C1-C4 haloalkyl, —OCH$_2$(phenyl), and C1-C4 haloalkoxy. In a more specific aspect, each of R1-R5 is independently chosen from —H, halo, —OCH$_2$(phenyl), and —CF$_3$. In a more specific aspect each of R1-R5 is —H.

In another aspect of this embodiment, R6 is —H or a C1-C4 alkyl. In a more specific aspect, R6 is —H.

In yet another aspect of this embodiment, R7 is —H or a C1-C4 alkyl. In a more specific aspect, R7 is —H.

In another aspect of this embodiment, each L is chosen from a bond, —CH$_2$—, —CH$_2$CH$_2$—, and —CH$_2$CH$_2$CH$_2$—. In a more specific aspect, L is chosen from a bond and —CH$_2$—.

In another aspect of this embodiment, $R_x$ if present, is chosen from —H, —C1-C6 alkyl, C2-C6 alkenyl, C2-C6 alkynyl, -L-cycloalkyl, -L-aryl, -L-heterocyclyl, wherein the cycloalkyl, aryl, and heterocyclyl are optionally substituted. In a more specific aspect, $R_x$ is chosen from —H, —CH(CH$_3$)$_2$, —C(CH$_3$)$_3$, —CH$_2$C≡CH, —CH$_2$CH=CH$_2$, cyclopropyl, cyclobutyl, cyclopentyl, cyclohexyl, and —CH$_2$(phenyl), wherein the cycloalkyl and phenyl group are optionally substituted.

In another aspect of this embodiment, $R_y$ if present, is chosen from —H, —C1-C6 alkyl, C2-C6 alkenyl, C2-C6 alkynyl, -L-cycloalkyl, -L-aryl, -L-heterocyclyl, wherein the cycloalkyl, aryl, and heterocyclyl are optionally substituted. In a more specific aspect, $R_y$ is chosen from —H, —CH(CH$_3$)$_2$, —C(CH$_3$)$_3$, —CH$_2$C≡CH, —CH$_2$CH=CH$_2$, cyclopropyl, cyclobutyl, cyclopentyl, cyclohexyl, and —CH$_2$(phenyl), wherein the cycloalkyl and phenyl groups are optionally substituted.

In one embodiment, the invention provides a compound of Formula I or a pharmaceutically acceptable salt thereof wherein:
  each of R1-R5 is optionally substituted and independently chosen from hydro, hydroxyl, halo, alkyl, alkenyl, alkynyl, alkoxy, arylalkyl, arylalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;
  R6 is chosen from —H and C1-C6 alkyl;
  R7 is chosen from —H, alkyl, and cycloalkyl;
  R8 is —C(=O)NR$_x$R$_y$;
  $R_x$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
  $R_y$ is chosen from —H, C1-C6 alkyl, C2-C6 alkynyl, C2-C6 alkenyl, -L-carbocyclyl, -L-aryl, -L-heterocyclyl, all of which are optionally substituted (except —H);
  each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O (CH$_2$)$_n$—, —(CH$_2$)$_n$NHC(=O)N(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)NH (CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

A preferred configuration around the cyclopropyl ring of the phenylcyclopropylamine derivatives of this embodiment is trans.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_x$ and R$_y$ have 1-4 optional substituents which are independently chosen from halo, alkyl, alkoxy, cycloalkoxy, haloalkyl, haloalkoxy, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In one aspect of this embodiment, R$_x$ and/or R$_y$ are independently chosen from —H, alkyl, alkynyl, alkenyl, -L-carbocyclyl, all of which are optionally substituted (except —H). In an even more preferred specific aspect, the optional substituents are 1-4 optional substituents independently chosen from alkyl, alkenyl, alkynyl, amino, aryl, arylalkyl, arylalkenyl, arylalkynyl, arylalkoxy, aryloxy, halo, and cyano. In one preferred aspect of this embodiment, R$_x$ and R$_y$ do not have substituents.

In a preferred aspect of this embodiment, one of R$_x$ and R$_y$ is hydro and the other of R$_x$ and R$_y$ is chosen from alkyl, alkynyl, alkenyl, -L-carbocyclyl, all of which are optionally substituted (except —H). In an even more specific preferred aspect, the 1-4 optional substituents are independently chosen from alkyl, alkenyl, alkynyl, amino, aryl, arylalkyl, arylalkenyl, arylalkynyl, arylalkoxy, aryloxy, halo, and cyano. In one preferred aspect, R$_x$ and R$_y$ do not have substituents.

In one aspect of this embodiment, each of R1-R5 is independently chosen from —H, halo, C1-C4 alkyl, C—C4 alkoxyl, C1-C4 haloalkyl, —OCH$_2$(phenyl), and C1-C4 haloalkoxy and —CF$_3$. In a more specific aspect, each of R1-R5 is independently chosen from —H, halo, —OCH$_2$(phenyl), and —CF$_3$. In a more specific aspect each of R1-R5 is —H.

In another aspect of this embodiment, R6 is —H or a C1-C4 alkyl. In a more specific aspect, R6 is —H.

In yet another aspect of this embodiment, R7 is —H or a C1-C4 alkyl. In a more specific aspect, R7 is —H.

In another aspect of this embodiment, each L is chosen from a bond, —CH$_2$—, —CH$_2$CH$_2$—, and —CH$_2$CH$_2$CH$_2$—. In a more specific aspect, L is chosen from a bond and —CH$_2$—.

In another aspect of this embodiment, R$_x$ if present, is chosen from —C1-C6 alkyl, C2-C6 alkenyl, C2-C6 alkynyl, -L-cycloalkyl, -L-aryl, -L-heterocyclyl, wherein the cycloalkyl, aryl, and heterocyclyl are optionally substituted. In a more specific aspect, R$_x$ is chosen from —H, —CH(CH$_3$)$_2$, —C(CH$_3$)$_3$, —CH$_2$C≡CH, —CH$_2$CH═CH$_2$, cyclopropyl, cyclobutyl, cyclopentyl, cyclohexyl, and —CH$_2$(phenyl), wherein the cycloalkyl and phenyl group are optionally substituted.

In another aspect of this embodiment, R$_y$ if present, is chosen from C1-C6 alkyl, C2-C6 alkenyl, C2-C6 alkynyl, -L-cycloalkyl, -L-aryl, -L-heterocyclyl, wherein the cycloalkyl, aryl, and heterocyclyl are optionally substituted. In a more specific aspect, R$_y$ is chosen from —H, —CH(CH$_3$)$_2$, —C(CH$_3$)$_3$, —CH$_2$C≡CH, —CH$_2$CH═CH$_2$, cyclopropyl, cyclobutyl, cyclopentyl, cyclohexyl, and —CH$_2$(phenyl), wherein the cycloalkyl and phenyl group are optionally substituted.

In one embodiment, the invention provides a compound of Formula I or a pharmaceutically acceptable salt thereof wherein:

each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and C1-C6 alkyl;

R7 is chosen from —H, alkyl, and cycloalkyl;

R8 is —C(═O)R$_z$;

R$_z$ is chosen from —H, C1-C6 alkoxy, -L-carbocyclyl, -L-heterocyclyl, and -L-aryl, all of which are optionally substituted (except —H);

each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of —(CH$_2$)$_n$—(CH$_2$)$_n$—, —(CH$_2$)$_n$C(═O)(CH$_2$)$_n$—, —(CH$_2$)$_n$C(═O)NH(CH$_2$)$_n$—, —(CH$_2$)$_n$NHC(═O)O(CH$_2$)$_n$—, —(CH$_2$)$_n$NHC(═O)NH(CH$_2$)$_n$—, —(CH$_2$)$_n$NHC(═S)S(CH$_2$)$_n$—, —(CH$_2$)$_n$OC(═O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and —(CH$_2$)$_n$NHC(═S)NH(CH$_2$)$_n$—, where each n is independently chosen from 0, 1, 2, 3, 4, 5, 6, 7, and 8.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

A preferred configuration around the cyclopropyl ring of the phenylcyclopropylamine derivatives of this embodiment is trans.

In one aspect of this embodiment, each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and the hydrocarbon portion is saturated. In a specific aspect, each L is independently chosen from —(CH$_2$)$_n$—(CH$_2$)$_n$— and —(CH$_2$)$_n$O(CH$_2$)$_n$ where each n is independently chosen from 0, 1, 2 and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_z$ is optionally substituted with 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In another aspect of this embodiment, $R_z$ is an optionally substituted heterocyclyl (i.e., -L-heterocyclyl where -L- is a bond). In a more specific aspect of this embodiment, the optionally substituted heterocyclyl has 1-4 optional substituents which are independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has 1 optional substituent which is chosen from alkyl and arylalkyl.

In yet another preferred aspect of this embodiment one of R2, R3, and R4 is chosen from -L-aryl and -L-heterocyclyl wherein -L- is independently chosen from $—(CH_2)_n—(CH_2)_n—$, $—(CH_2)_nNH(CH_2)_n—$, $—(CH_2)_nO(CH_2)_n—$, and $—(CH_2)_nS(CH_2)_n—$, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, cyano, and amino. In a more specific preferred aspect, R1, R5, R6 and R7 are each hydro.

In one aspect of this embodiment, each of R1-R5 is independently chosen from —H, halo, C1-C4 alkyl, C—C4 alkoxyl, C1-C4 haloalkyl, —OCH$_2$(phenyl), and C1-C4 haloalkoxy. In a more specific aspect, each of R1-R5 is independently chosen from —H, halo, —OCH$_2$(phenyl), and —CF$_3$. In a more specific aspect each of R1-R5 is —H.

In another aspect of this embodiment, R6 is —H or a C1-C4 alkyl. In a more specific aspect, R6 is —H.

In yet another aspect of this embodiment, R7 is —H or a C1-C4 alkyl. In a more specific aspect, R7 is —H.

In another aspect of this embodiment, each L is chosen from a bond, —CH$_2$—, —CH$_2$CH$_2$—, and —CH$_2$CH$_2$CH$_2$—. In a more specific aspect, L is chosen from a bond and —CH$_2$—.

In another aspect of this embodiment, $R_z$ if present is an optionally substituted -L-heterocyclyl. In a more specific aspect, $R_z$ is optionally substituted and chosen from N-methylpiperazinyl, morpholinyl, and piperidinyl. In a more specific aspect, $R_z$ is chosen from N-methylpiperazinyl, morpholinyl, and piperidinyl.

In one embodiment, the invention provides a compound of Formula I or a pharmaceutically acceptable salt thereof wherein:
  each of R1-R5 is optionally substituted and independently chosen from hydro, hydroxyl, halo, alkyl, alkenyl, alkynyl, alkoxy, arylalkyl, arylalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, and —NO$_2$;
  R6 is chosen from —H and C1-C6 alkyl;
  R7 is chosen from —H, alkyl, and cycloalkyl;
  R8 is —C(=O)R$_z$,
  R$_z$ is chosen from —H, -L-carbocyclyl, -L-heterocyclyl, -L-aryl, wherein the aryl, heterocyclyl, or carbocycle is optionally substituted;
  each L is a linker that links the main scaffold of Formula I to a carbocyclyl, heterocyclyl, or aryl group, wherein the hydrocarbon portion of the linker -L- is saturated, partially saturated, or unsaturated, and is independently chosen from a saturated parent group having a formula of $—(CH_2)_n—(CH_2)_n—$, $—(CH_2)_nC(=O)(CH_2)_n—$, $—(CH_2)_nC(=O)NH(CH_2)_n—$, $—(CH_2)_nNHC(=O)O(CH_2)_n—$, $—(CH_2)_nNHC(=O)NH(CH_2)_n—$, $—(CH_2)_n NHC(=S)S(CH_2)_n—$, $—(CH_2)_nOC(=O)S(CH_2)_n—$, $—(CH_2)_nNH(CH_2)_n—$, $—(CH_2)_nO(CH_2)_n—$, $—(CH_2)_nS(CH_2)_n—$, and $—(CH_2)_nNHC(=S)NH(CH_2)_n—$, where each n is independently chosen from 0, 1, 2, 3, 4, 5, 6, 7, and 8; and pharmaceutically acceptable salts thereof.

According to this embodiment, optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido. In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

A preferred configuration around the cyclopropyl ring of the phenylcyclopropylamine derivatives of this embodiment is trans.

In one aspect of this embodiment, each L is independently chosen from $—(CH_2)_n—(CH_2)_n—$, $—(CH_2)_nNH(CH_2)_n—$, $—(CH_2)_nO(CH_2)_n—$, and $—(CH_2)_nS(CH_2)_n—$, where each n is independently chosen from 0, 1, 2, and 3, and the hydrocarbon portion is saturated. In a specific aspect, each L is independently chosen from $—(CH_2)_n—(CH_2)_n—$ and $—(CH_2)_nO(CH_2)_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In one aspect of this embodiment, R$_z$ is optionally substituted with 1-4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In another aspect of this embodiment, R$_z$ is an optionally substituted heterocyclyl (i.e., -L-heterocyclyl where -L- is a bond). In a more specific aspect of this embodiment, the optionally substituted heterocyclyl has 1-4 optional substituents which are independently chosen from alkyl, alkenyl, alkynyl, amino, aryl, arylalkyl, arylalkenyl, arylalkynyl, arylalkoxy, aryloxy, halo, and cyano. In an even more specific aspect of the heterocyclyl has 1 optional substituent which is chosen from alkyl and arylalkyl.

In yet another preferred aspect of this embodiment one of R2, R3, and R4 is chosen from -L-aryl and -L-heterocyclyl wherein -L- is independently chosen from $—(CH_2)_n—(CH_2)_n—$, $—(CH_2)_nNH(CH_2)_n—$, $—(CH_2)_nO(CH_2)_n—$, and —(CH$_2$)$_n$S(CH$_2$)$_n$—, where each n is independently chosen from 0, 1, 2, and 3; and the others of R2, R3, and R4 are chosen from hydro, halo, C1-C6 alkyl, C1-C6 alkoxy, C1-C6 haloalkyl, C1-C6 haloalkoxy, and cyano. In a more specific preferred aspect, R1, R5, R6 and R7 are each hydro.

In one aspect of this embodiment, each of R1-R5 is independently chosen from —H, halo, C1-C4 alkyl, C—C4 alkoxyl, C1-C4 haloalkyl, —OCH$_2$(phenyl), and C1-C4 haloalkoxy. In a more specific aspect, each of R1-R5 is independently chosen from —H, halo, —OCH$_2$(phenyl), and —CF$_3$. In a more specific aspect each of each of R1-R5 is —H.

In another aspect of this embodiment, R6 is —H or a C1-C4 alkyl. In a more specific aspect, R6 is —H.

In yet another aspect of this embodiment, R7 is —H or a C1-C4 alkyl. In a more specific aspect, R7 is —H.

In another aspect of this embodiment, each L is chosen from a bond, —CH$_2$—, —CH$_2$CH$_2$—, and —CH$_2$CH$_2$CH$_2$—. In a more specific aspect, L is chosen from a bond and —CH$_2$—.

In another aspect of this embodiment, R$_z$ if present, is an optionally substituted -L-heterocyclyl. In a more specific aspect, R$_z$ is optionally substituted and chosen from N-methylpiperazinyl, morpholinyl, and piperidinyl. In a more specific aspect, R$_z$ is chosen from N-methylpiperazinyl, morpholinyl, and piperidinyl.

In one preferred embodiment, the invention provides a compound of Formula I(a), a pharmaceutical composition comprising a compound of Formula I(a) and a pharmaceutically acceptable carrier, and/or a method for treating diseases by administering to an individual a pharmaceutical composition comprising a compound of Formula I(a).

The invention therefore provides a compound of Formula I(a) or a pharmaceutically acceptable salt thereof:

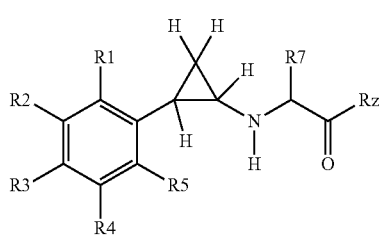

Formula I(a)

wherein
R1 is chosen from hydro, halo, C1-C6 alkyl, C1-C6 alkoxy, C1-C6 haloalkyl, C1-C6 haloalkoxy, and cyano;
one of R2, R3, and R4 is chosen from -L-aryl and -L-heterocyclyl wherein -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3, and wherein the aryl or heterocyclyl moeity of the -L-aryl and -L-heterocyclyl group is optionally substituted with one group chosen from halo, C1-C6 alkyl, C1-C6 alkoxy, C1-C6 haloalkyl, C1-C6 haloalkoxy, and cyano; and the others of R2, R3, and R4 are independently chosen from hydro, halo, C1-C6 alkyl, C1-C6 alkoxy, C1-C6 haloalkyl, C1-C6 haloalkoxy, and cyano;
R5 is chosen from hydro, halo, C1-C6 alkyl, C1-C6 alkoxy, C1-C6 haloalkyl, C1-C6 haloalkoxy, and cyano;
R7 is chosen from hydro, C1-C6 alkyl, and cycloalkyl;
R$_z$ is an optionally substituted -L-heterocyclyl having from 1-4 optional substituents which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido, and wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3.

In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

A preferred configuration around the cyclopropyl ring of the phenylcyclopropylamine derivatives of this embodiment is trans.

In a specific aspect of this embodiment, each L is independently chosen from —(CH$_2$)$_n$—(CH$_2$)$_n$— and —(CH$_2$)$_n$O(CH$_2$)$_n$ where each n is independently chosen from 0, 1, 2, and 3. In a more specific aspect of this embodiment, each L is chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—. In an even more specific aspect, each L is chosen from a bond, —CH$_2$—, —CH$_2$CH$_2$—, OCH$_2$—, and —CH$_2$CH$_2$CH$_2$—. In yet an even more specific aspect, L is chosen from a bond and —CH$_2$—.

In a more specific aspect of this embodiment, the invention provide a compound of Formula I(a) wherein the heterocyclyl of R$_z$ is optionally substituted with 1-4 optional substituents independently chosen from alkyl, alkenyl, amino, aryl, arylalkyl, arylalkenyl, arylalkynyl, arylalkoxy, and aryloxy. In an even more specific aspect, the heterocyclyl of R$_z$ has one optional substituent which is chosen from alkyl and arylalkyl.

In an even more specific aspect, the invention provides compounds of Formula I(a) wherein the optional substituents on the ring system of R$_z$ are chosen from C1-C6 alkyl and arylalkyl wherein the alkyl moiety of the arylalkyl group is a C1-C6 alkyl.

In one aspect of this embodiment, the invention provides a compound of Formula I(a) or a pharmaceutically acceptable salt thereof wherein:
R1 and R5 are each hydro;
one of R2, R3, and R4 is chosen an -L-aryl group wherein the -L- is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; wherein the aryl moeity of the -L-aryl group is optionally substituted with one group chosen from halo, C1-C6 alkyl, C1-C6 alkoxy, C1-C6 haloalkyl, C1-C6 haloalkoxy, cyano, and amino;
R7 is hydro;
R$_z$ is an -L-heterocyclyl group wherein the heterocyclyl is optionally substituted with 1-4 optional substituents and the heterocyclyl group is chosen from morpholino, piperidyl, piperazinyl, pyrrolidinyl, thiomorpholino, homopiperazinyl, imidazolyl, imidazolidinyl, pyrazolidinyl, dioxanyl and dioxolanyl, and the -L- is independently chosen from —(CH$_2$)$_n$NH(CH$_2$)$_n$—, —(CH$_2$)$_n$O(CH$_2$)$_n$—, and (CH$_2$)$_n$S(CH$_2$)$_n$—, wherein each n is independently chosen from 0, 1, 2, and 3.

In a related aspect, the invention provides a pharmaceutical composition comprising a compound as defined in this paragraph and a pharmaceutically acceptable carrier. In yet another related aspect, the pharmaceutical composition, as described above, can be used for treating and/or preventing cancer.

In a more specific aspect of this embodiment, the invention provides a compound of Formula I(a) wherein the $R_z$ is an -L-heterocyclyl group wherein the -L- is a bond and the heterocyclyl is optionally substituted with 1-4 optional substituents and the heterocyclyl group is chosen from morpholino, piperidinyl, piperizinyl, and pyrrolidinyl. In an even more specific aspect of this embodiment, the 1-4 optional substituents are independently chosen from alkyl, alkenyl, amino, aryl, arylalkyl, arylalkenyl, arylalkynyl, arylalkoxy, and aryloxy. In yet an even more specific aspect of the heterocyclic group is chosen from morpholino, piperidinyl, piperizinyl, and pyrrolidinyl and the heterocyclyl has 1 optional substituent chosen from alkyl and arylalkyl.

In one aspect of this embodiment, -L- is $—(CH_2)_n—(CH_2)_n—$ or $(CH_2)_nO(CH_2)_n$, where each n is independently chosen from 0, 1, 2, and 3.

In one aspect of this embodiment, the invention provides a compound of Formula I(a) or a pharmaceutically acceptable salt thereof wherein:
  R1 and R5 are hydro;
  one of R2, R3, and R4 is chosen from -L-aryl and -L-heterocyclyl wherein the -L- is independently chosen from $—(CH_2)_n—(CH_2)_n—$, $—(CH_2)_nNH(CH_2)_n—$, $—(CH_2)_nO(CH_2)_n—$, and $—(CH_2)_nS(CH_2)_n—$, where each n is independently chosen from 0, 1, 2, and 3; and the others of R2, R3, and R4 are hydro, and wherein the aryl or heterocyclyl moeity of the -L-aryl and -L-heterocyclyl group is optionally substituted with one group chosen from halo, C1-C6 alkyl, C1-C6 alkoxy, C1-C6 haloalkyl, C1-C6 haloalkoxy, and cyano;
  R7 is hydro;
  $R_z$ is a heterocyclyl group (the -L- of -L-heterocyclyl is a bond) wherein the heterocyclyl is optionally substituted with 1-4 optional substituents and the heterocyclyl group is chosen from morpholino, piperidyl, piperazinyl, pyrrolidinyl, homopiperazinyl.

In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

In one aspect of this embodiment, the invention provides a compound of Formula I(a) or a pharmaceutically acceptable salt thereof wherein:
  R1 and R2 are each hydro;
  R3 is -L-aryl wherein the -L- is independently chosen from $—(CH_2)_n—(CH_2)_n—$, $—(CH_2)_nNH(CH_2)_n—$, $—(CH_2)_nO(CH_2)_n—$, and $—(CH_2)_nS(CH_2)_n—$, where each n is independently chosen from 0, 1, 2, and 3; and the others of R2, R3, and R4 are hydro, and wherein the aryl moeity of the -L-aryl group is optionally substituted with one group chosen from halo, C1-C6 alkyl, C1-C6 alkoxy, C1-C6 haloalkyl, C1-C6 haloalkoxy, and cyano;
  R4 and R5 are each hydro;
  R7 is hydro;
  $R_z$ is a heterocyclyl group (i.e., the -L- of -L-heterocyclyl is a bond) wherein the heterocyclyl is optionally substituted with 1-4 optional substituents and the heterocyclyl group is chosen from morpholino, piperidyl, piperazinyl, pyrrolidinyl, homopiperazinyl.

In an even more specific aspect, the heterocyclyl has one substituent chosen from alkyl and arylalkyl. In a related aspect, the invention provides a pharmaceutical composition comprising a compound as defined in this paragraph and a pharmaceutically acceptable carrier. In yet another related aspect, the pharmaceutical composition, as described above, is used for treating and/or preventing cancer.

In one aspect of this embodiment, the invention provides a compound of Formula I(a) wherein R3 is an optionally substituted aryl group having from 1-4 optional substituents. In a more specific aspect, R3 is an optionally substituted phenyl group and the 1-4 optional substituents are independently chosen from halo, alkyl, alkoxy, haloalkyl, haloalkoxy, sulphonyl, and cyano. In a more specific aspect, R3 is a optionally substituted phenyl group which has 1 or 2 optional substituents independently chosen from halo, alkyl, alkoxy, haloalkyl, haloalkoxy, sulphonyl, and cyano.

In one aspect of this embodiment, the invention provides a compound Formula I(a) wherein R3 is an optionally substituted arylalkoxy group having from 1-4 optional substituents. In a more specific aspect, R3 is an optionally substituted benzyloxy group and the 1-4 optional substituents are independently chosen from halo, alkyl, alkoxy, haloalkyl, haloalkoxy, sulphonyl, and cyano. In a more specific aspect, R3 is an optionally substituted benzyloxy group which has 1 or 2 optional substituents independently chosen from halo, alkyl, alkoxy, haloalkyl, haloalkoxy, sulphonyl, and cyano.

As used herein, the term "optional substituents" refers to optional groups that are attached to the parent group referred to in each particular instance. Unless otherwise specified, "optionally substituted," "may be optional substituted" and similar constructions refers to optional substitutents which do not have further substitution (S). Optionally substituted refers to zero or from 1 to 4 optional substituents on the parent group which are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido, unless otherwise specified.

In some of the embodiments of the invention related to compounds, compositions and uses of compounds of Formula I, the compound does not have the structure of the compounds having CAS registration nos. 928314-26-5 (Acetamide, N,N-diphenyl-2-[[(1R,2S)-2-phenylcyclopropyl]amino]-), 917388-09-1 (4-Isoxazolecarboxamide, N-[[[[3,5-dichloro-4-[[2-[[(1R,2S)-2-phenylcyclopropyl]amino]acetyl]amino]phenyl]methyl]amino]iminomethyl]-3-(4-methoxyphenyl)-5-methyl-), 825630-21-5 (Acetamide, N-[4-[8-(methylamino)imidazo[1,2-a]pyrazin-3-yl]phenyl]-2-[(2-phenylcyclopropyl)amino]-), 728873-64-1 (Benzamide, N-[(1S,2R)-2-hydroxy-1-[(hydroxyamino)carbonyl]propyl]-4-[[4-[[[[(1S,2R)-2-phenylcyclopropyl]amino]acetyl]amino]phenyl]ethynyl]-(9CI)), and/or 728871-98-5 (Benzamide, N-[(1S)-1-(aminomethyl)-2-(hydroxyamino)-2-oxoethyl]-4-[[4-[[[[(1S,2R)-2-phenylcyclopropyl]amino]acetyl]amino]phenyl]ethynyl]-(9CI)). N-[(1S)-1-(aminomethyl)-2-(hydroxyamino)-2-oxoethyl]-4-({4-[({[(1S,2R)-2-phenylcyclopropyl]amino}acetyl)amino]phenyl}ethynyl)benzamide; N-{(1S,2R)-2-hydroxy-1-[(hydroxyamino)carbonyl]propyl}-4-({4-[({[(1S,2R)-2-phenylcyclopropyl]amino}acetyl)amino]phenyl}ethynyl)benzamide; N-[4-(8-

Methylamino-imidazo[1,2-a]pyrazin-3-yl)-phenyl]-2-(2-phenyl-cyclopropylamino)-acetamide.

In one embodiment, the invention is a method for screening for an agent that inhibits LSD1 and/or LSD1 and MAO-B selectively compared to MAO-A comprising:
(a) providing an arylcyclopropylamine acetamide or derivative thereof
(b) assaying the arylcyclopropylamine acetamide or derivative thereof for its ability to inhibit LSD1, MAO-B, and MAO-A
(c) wherein an arylcyclopropylamine acetamide or derivative thereof is a selective inhibitor of LSD1 and/or LSD1 and MAO-B if the arylcyclopropylamine acetamide or derivative thereof has an inhibitory constant for LSD1 or LSD1 and MAO-B that is at least two-fold lower than the its inhibitory constant for MAO-A.

In one embodiment, the invention provides a method of treating and/or preventing a disease or condition comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a disease or condition. In a related aspect, the invention provides for the use of a compound of Formula I for the manufacture of a medicament for treating and/or preventing a disease or condition. In a more specific aspect of this embodiment, the compound of Formula I is a compound of Formula I(a) as defined above.

In one embodiment, the invention provides a method of treating or preventing cancer comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing cancer. In a related aspect, the invention provides for the use of a compound of Formula I for the manufacture of a medicament for treating and/or preventing cancer. In one aspect of this embodiment, the cancer is breast cancer, colorectal cancer, lung cancer, prostate cancer, testicular cancer, or brain cancer. In a more specific aspect of this embodiment, the compound of Formula I is a compound of Formula I(a) as defined above.

In one embodiment, the invention provides a method of inhibiting LSD1 activity comprising administering, to a patient in need of treatment, an amount of a composition comprising a compound of Formula I and a pharmaceutically acceptable carrier sufficient to inhibit LSD1 activity. In one aspect of this embodiment, the invention provides a compound of Formula I for use in inhibiting LSD1. In a related aspect, the invention provides for the use of a compound of Formula I for the manufacture of a medicament for inhibiting LSD1. In a more specific aspect of this embodiment, the compound of Formula I is a compound of Formula I(a) as defined above.

In one embodiment, the invention provides a method of treating and/or preventing a neurodegenerative disease or disorder comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition. In a more specific aspect of this embodiment, the compound of Formula I is a compound of Formula I(a) as defined above.

The invention provides compounds of Formula I which are selective inhibitors of LSD1 that inhibit LSD1 to a greater extent than MAO-A and/or MAO-B. Preferably LSD1 selective inhibitors have IC50 values for LSD1 which are at least 2-fold lower than the 1050 value for MAO-A and/or MAO-B. In some embodiments, the LSD1 selective inhibitors have IC50 values which are at least 5-fold lower for LSD1 as compared to MAO-A and MAO-B. In some embodiments, the LSD1 selective inhibitors have IC50 values which are at least 10-fold lower for LSD1 as compared to MAO-A and MAO-B. In a more specific aspect of this embodiment, the compound of Formula I is a compound of Formula I(a) as defined above.

The invention provides a compound of Formula I or a pharmaceutically acceptable salt thereof where the compound is chosen from N-cyclopropyl-2-{[(trans)-2-phenylcyclopropyl]amino}acetamide; 2-{[(trans)-2-phenylcyclopropyl]amino}acetamide; N-cyclopropyl-2-{[(trans)-2-phenylcyclopropyl]amino}propanamide; 2-{[(trans)-2-phenylcyclopropyl]amino}-N-prop-2-ynylacetamide; N-isopropyl-2-{[(trans)-2-phenylcyclopropyl]amino}acetamide; N-(tert-butyl)-2-{[(trans)-2-phenylcyclopropyl]amino}acetamide; N-(2-morpholin-4-yl-2-oxoethyl)-N-[(trans)-2-phenylcyclopropyl]amine; 2-{[(trans)-2-phenylcyclopropyl]amino}propanamide; Methyl 2-{[(trans)-2-phenylcyclopropyl]amino}propanoate; 2-((trans)-2-phenylcyclopropylamino)-N-(piperidin-4-ylmethyl)acetamide; N-(1-(dimethylamino)propan-2-yl)-2-((trans)-2-phenylcyclopropylamino)acetamide; N-(2-(dimethylamino)ethyl)-2-((trans)-2-phenylcyclopropylamino)acetamide; 1-((S)-3-(dimethylamino)pyrrolidin-1-yl)-2-((trans)-2-phenylcyclopropylamino)ethanone; 1-((R)-3-(dimethylamino)pyrrolidin-1-yl)-2-((trans)-2-phenylcyclopropylamino)ethanone; 1-((R)-3-(dimethylamino)pyrrolidin-1-yl)-2-((trans)-2-phenylcyclopropylamino)ethanone; 2-((trans)-2-phenylcyclopropylamino)-N—((R)-pyrrolidin-3-yl)acetamide; 2-((trans)-2-phenylcyclopropylamino)-N—((R)-pyrrolidin-3-yl)acetamide; N-cyclopropyl-2-{methyl[(trans)-2-phenylcyclopropyl]amino}acetamide 2-{methyl[(trans)-2-phenylcyclopropyl]amino}acetamide; 1-(4-methylpiperazin-1-yl)-2-((trans)-2-phenylcyclopropylamino)ethanone; 1-(4-ethylpiperazin-1-yl)-2-((trans)-2-phenylcyclopropylamino)ethanone; 1-(4-benzylpiperazin-1-yl)-2-((trans)-2-phenylcyclopropylamino)ethanone; 2-((trans)-2-phenylcyclopropylamino)-1-(4-phenylpiperazin-1-yl)ethanone; 2-((trans)-2-(4-(benzyloxy)phenyl)cyclopropylamino)-1-(4-methylpiperazin-1-yl)ethanone; 2-((trans)-2-(1,1'-biphenyl-4-yl)cyclopropylamino)-1-(4-methylpiperazin-1-yl)ethanone; 2-((trans)-2-(4-(benzyloxy)phenyl)cyclopropylamino)-N-cyclopropylacetamide; 2-((trans)-2-(4-(3-fluorobenzyloxy)phenyl)cyclopropylamino)-1-(4-methylpiperazin-1-yl)ethanone; 2-((trans)-2-(4-(4-fluorobenzyloxy)phenyl)cyclopropylamino)-1-(4-methylpiperazin-1-yl)ethanone; 2-((trans)-2-(4-(3-chlorobenzyloxy)phenyl)cyclopropylamino)-1-(4-methylpiperazin-1-yl)ethanone; 2-((trans)-2-(4-(3-chlorobenzyloxy)phenyl)cyclopropylamino)-1-(4-methylpiperazin-1-yl)ethanone; 2-((trans)-2-(4-(3-bromobenzyloxy)phenyl)cyclopropylamino)-1-(4-methylpiperazin-1-yl)ethanone; 4-((4-((trans)-2-(2-(4-methylpiperazin-1-yl)-2-oxoethylamino)cyclopropyl)phenoxy)methyl)benzonitrile; 1-(4-methylpiperazin-1-yl)-2-((trans)-2-(4-phenethoxyphenyl)cyclopropylamino)ethanone; 1-(4-methylpiperazin-1-yl)-2-((trans)-2-(4- phenethoxyphenyl)cyclopropylamino)ethanone; 2-((trans)-2-(biphenyl-4-yl)cyclopropylamino)-1-(4-methylpiperazin-1-yl)ethanone 2-((trans)-2-(4-pyridin-3-ylphenyl)cyclopropylamino)-1-(4-methylpiperazin-1-yl)ethanone; 2-((trans)-2-(3'-methoxy-1,1'-biphenyl-4-yl)cyclopropylamino)-1-(4-methylpiperazin-1-yl)ethanone; 2-((trans)-2-(4'-methoxybiphenyl-4-yl)cyclopropylamino)-1-(4-methylpiperazin-1-yl)ethanone; 4'-((trans)-2-(2-(4-methylpiperazin-1-yl)-2-oxoethylamino)cyclopropyl)biphenyl-3-carbonitrile; 4'-((trans)-2-(2-(4-methylpiperazin-1-yl)-2-oxoethylamino)cyclopropyl)biphenyl-3-carbonitrile; 2-((trans)-2-(4'-fluorobiphenyl-4-yl)cyclopropylamino)-1-(4-methylpiperazin-1-yl)ethanone; 1-(4-methylpiperazin-1-yl)-2-((trans)-2-(3'-(trifluoromethyl)biphenyl-4-yl)cyclopropylamino)ethanone; 1-(4-methylpiperazin-1-yl)-2-((trans)-2-(4'-(methylsulfonyl)biphenyl-4-yl)cyclopropylamino)ethanone; 2-((trans)-2-(3',5'-dichlorobiphenyl-4-yl)cyclopropylamino)-1-(4-methylpiperazin-1-yl)ethanone; 2-((trans)-2-(2',4'-difluorobiphenyl-4-yl)cyclopropylamino)-1-(4-methylpiperazin-1-yl)ethanone; 2-((trans)-2-(4-(6-methoxypyridin-3-yl)phenyl)cyclopropylamino)-1-(4-methylpiperazin-1-yl)ethanone; 2-((trans)-2-(2'-fluorobiphenyl-4-yl)cyclopropylamino)-1-(4-methylpiperazin-1-yl)ethanone; 1-(4-methylpiperazin-1-yl)-2-((trans)-2-(4'-(trifluoromethyl)biphenyl-4-yl)cyclopropylamino)ethanone; 1-(4-methylpiperazin-1-yl)-2-((trans)-2-(4'-(trifluoromethyl)biphenyl-4-yl)cyclopropylamino)ethanone; 1-(4-methylpiperazin-1-yl)-2-((trans)-2-(4'-(trifluoromethoxy)biphenyl-4-yl)cyclopropylamino)ethanone; 1-(4-methylpiperazin-1-yl)-2-((trans)-2-(4'-(trifluoromethoxy)biphenyl-4-yl)cyclopropylamino) ethanone; 1-(4-methylpiperazin-1-yl)-2-((trans)-2-(4'-(trifluoromethoxy)biphenyl-4-yl)cyclopropylamino)ethanone; 1-(4-methylpiperazin-1-yl)-2-((trans)-2-(4'-(trifluoromethoxy)biphenyl-4-yl)cyclopropylamino)ethanone; 2-((trans)-2-(3'-chlorobiphenyl-4-yl)cyclopropylamino)-1-(4-methylpiperazin-1-yl)ethanone; 2-((trans)-2-(4'-chlorobiphenyl-4-yl)cyclopropylamino)-1-(4-methylpiperazin-1-yl)ethanone; 2-((trans)-2-(5'-fluoro-2'-(trifluoromethyl)biphenyl-4-yl)cyclopropylamino)-1-(4-methylpiperazin-1-yl)ethanone; 2-((trans)-2-(4-(2-methoxypyridin-3-yl)phenyl)cyclopropylamino)-1-(4-methylpiperazin-1-yl)ethanone; 1-(4-methylpiperazin-1-yl)-2-((trans)-2-(4-phenethylphenyl)cyclopropylamino) ethanone; and 2-((trans)-2-(4-cyclopropylphenyl)cyclopropylamino)-1-(4-methylpiperazin-1-yl)ethanone.

In one aspect, the invention provides a compound of Formula I or a pharmaceutically acceptable salt thereof wherein said compound is chosen from N-cyclopropyl-2-{[(trans)-2-phenylcyclopropyl]amino}acetamide; 2-{[(trans)-2-phenylcyclopropyl]amino}acetamide; N-cyclopropyl-2-{[(trans)-2-phenylcyclopropyl]amino}propanamide; 2-{[(trans)-2-phenylcyclopropyl]amino}-N-prop-2-ynylacetamide; N-isopropyl-2-{[(trans)-2-phenylcyclopropyl]amino}acetamide; N-(tert-butyl)-2-{[(trans)-2-phenylcyclopropyl]amino}acetamide; N-(2-morpholin-4-yl-2-oxoethyl)-N-[(trans)-2-phenylcyclopropyl]amine; 2-{[(trans)-2-phenylcyclopropyl]amino}propanamide; Methyl 2-{[(trans)-2-phenylcyclopropyl]amino}propanoate; N-cyclopropyl-2-{methyl[(trans)-2-phenylcyclopropyl]amino}acetamide; 2-{methyl[(trans)-2-phenylcyclopropyl]amino}acetamide; N-methyl-trans-2-(Phenylcyclopropylamino)propanamide; 1-(4-methylpiperazin-1-yl)-2-((trans)-2-phenylcyclopropylamino)ethanone; 1-(4-ethylpiperazin-1-yl)-2-((trans)-2-phenylcyclopropylamino)ethanone; 1-(4-benzylpiperazin-1-yl)-2-((trans)-2-phenylcyclopropylamino)ethanone; 2-((trans)-2-phenylcyclopropylamino)-1-(4-phenylpiperazin-1-yl)ethanone; 2-((trans)-2-(4-(benzyloxy)phenyl)cyclopropylamino)-1-(4-methylpiperazin-1-yl)ethanone; 2-((trans)-2-(4-(benzyloxy)phenyl)cyclopropylamino)-N-cyclopropylacetamide; 2-((trans)-2-(4-(3-fluorobenzyloxy)phenyl)cyclopropylamino)-1-(4-methylpiperazin-1-yl)ethanone; 2-((trans)-2-(4-(3-chlorobenzyloxy)phenyl)cyclopropylamino)-1-(4-methylpiperazin-1-yl)ethanone; 2-((trans)-2-(biphenyl-4-yl)cyclopropylamino)-1-(4-methylpiperazin-1-yl)ethanone; 1-(4-methylpiperazin-1-yl)-2-((trans)-2-(4-phenethoxyphenyl)cyclopropylamino)ethanone; 2-((trans)-2-(4-(4-fluorobenzyloxy)phenyl)cyclopropylamino)-1-(4-methylpiperazin-1-yl)ethanone; and 2-((trans)-2-(4-(biphenyl-4-ylmethoxy)phenyl)cyclopropylamino)-1-(4-methylpiperazin-1-yl)ethanone.

In one aspect, the invention provides a compound of Formula I or a pharmaceutically acceptable salt thereof wherein the compound is chosen from 2-({(trans)-2-[4-(benzyloxy)phenyl]cyclopropyl}amino)-N-cyclopropylacetamide, N-[(trans)-2-(4-benzyloxyphenyl)cyclopropyl]}-N-[2-(4-methylpiperazin-1-yl)-2-oxoethyl]amine, N-[2-oxo-2-(4-phenylpiperazin-1-yl)ethyl]-N-[(trans)-2-phenylcyclopropyl]amine, N-[2-(4-benzylpiperazin-1-yl)-2-oxoethyl]-N-[(trans)-2-phenylcyclopropyl]amine, N-[2-(4-ethylpiperazin-1-yl)-2-oxoethyl]-N-[(trans)-2-phenylcyclopropyl]amine, N-[2-(4-methylpiperazin-1-yl)-2-oxoethyl]-N-[(trans)-2-phenylcyclopropyl]amine, 2-((trans)-2-(4-pyridin-3-ylphenyl)cyclopropylamino)-1-(4-methylpiperazin-1-yl)ethanone, and 2-((trans)-2-(3'-methoxy-1,1'-biphenyl-4-yl)cyclopropylamino)-1-(4-methylpiperazin-1-yl)ethanone.

In one aspect, the invention provides a compound of Formula I or a pharmaceutically acceptable salt thereof wherein the compound is chosen from N-cyclopropyl-2-{[(1S,2R)-2-phenylcyclopropyl]amino}acetamide; 2-{[(1S,2R)-2-phenylcyclopropyl]amino}acetamide; N-cyclopropyl-2-{[(1S,2R)-2-phenylcyclopropyl]amino}propanamide; 2-{[(1S,2R)-2-phenylcyclopropyl]amino}-N-prop-2-ynylacetamide; N-isopropyl-2-{[(1S,2R)-2-phenylcyclopropyl]amino}acetamide; N-(tert-butyl)-2-{[(1S,2R)-2-phenylcyclopropyl]amino}acetamide; N-(2-morpholin-4-yl-2-oxoethyl)-N-[(1S,2R)-2-phenylcyclopropyl]amine; 2-{[(1S,2R)-2-phenylcyclopropyl]amino}propanamide; Methyl 2-{[(1S,2R)-2-phenylcyclopropyl]amino}propanoate; N-cyclopropyl-2-{methyl[(1S,2R)-2-phenylcyclopropyl]amino}acetamide; 2-{methyl[(1S,2R)-2-phenylcyclopropyl]amino}acetamide; N-methyl-trans-2-(Phenylcyclopropylamino)propanamide; 1-(4-methylpiperazin-1-yl)-2-((1S,2R)-2-phenylcyclopropylamino)ethanone; 1-(4-ethylpiperazin-1-yl)-2-((1S,2R)-2-phenylcyclopropylamino)ethanone; 1-(4-benzylpiperazin-1-yl)-2-((1S,2R)-2-phenylcyclopropylamino)ethanone; 2-((1S,2R)-2-phenylcyclopropylamino)-1-(4-phenylpiperazin-1-yl)ethanone; 2-((1S,2R)-2-(4-(benzyloxy)phenyl)cyclopropylamino)-1-(4-methylpiperazin-1-yl)ethanone; 2-((1S,2R)-2-(4-(benzyloxy)phenyl)cyclopropylamino)-N-cyclopropylacetamide; 2-((1S,2R)-2-(4-(3-fluorobenzyloxy)phenyl)cyclopropylamino)-1-(4-methylpiperazin-1-yl)ethanone; 2-((1S,2R)-2-(4-(3-chlorobenzyloxy)phenyl)cyclopropylamino)-1-(4-methyl piperazin-1-yl)ethanone; 2-((1S,2R)-2-(biphenyl-4-yl)cyclopropylamino)-1-(4-methylpiperazin-1-yl)ethanone; 1-(4-methylpiperazin-1-yl)-2-((1S,2R)-2-(4-phenethoxyphenyl)cyclopropylamino)ethanone; 2-((1S,2R)-2-(4-(4-fluorobenzyloxy)phenyl)cyclopropylamino)-1-(4-methylpiperazin-1-yl)ethanone;

and 2-((1S,2R)-2-(4-(biphenyl-4-ylmethoxy)phenyl)cyclopropylamino)-1-(4-methylpiperazin-1-yl)ethanone.

In one aspect, the invention provides a compound of Formula I or a pharmaceutically acceptable salt thereof wherein the compound is chosen from: 2-({(1S,2R)-2-[4-(benzyloxy) phenyl]cyclopropyl}amino)-N-cyclopropylacetamide, N-[(1S,2R)-2-(4-benzyloxyphenyl)cyclopropyl]}-N-[2-(4-methylpiperazin-1-yl)-2-oxoethyl]amine, N-[2-oxo-2-(4-phenylpiperazin-1-yl)ethyl]-N-[(1S,2R)-2-phenylcyclopropyl]amine, N-[2-(4-benzylpiperazin-1-yl)-2-oxoethyl]-N-[(1S,2R)-2-phenylcyclopropyl]amine, N-[2-(4-ethylpiperazin-1-yl)-2-oxoethyl]-N-[(1S,2R)-2-phenylcyclopropyl]amine, N-[2-(4-methylpiperazin-1-yl)-2-oxoethyl]-N-[(1S,2R)-2-phenylcyclopropyl]amine, 2-((1S,2R)-2-(4-pyridin-3-ylphenyl)cyclopropylamino)-1-(4-methylpiperazin-1-yl)ethanone, and 2-((1S,2R)-2-(3'-methoxy-1,1'-biphenyl-4-yl)cyclopropylamino)-1-(4-methylpiperazin-1-yl)ethanone.

In one aspect, the invention provides a compound of Formula I or a pharmaceutically acceptable salt thereof wherein the compound is chosen from N-cyclopropyl-2-{[(1R,2S)-2-phenylcyclopropyl]amino}acetamide; 2-{[(1R,2S)-2-phenylcyclopropyl]amino}acetamide; N-cyclopropyl-2-{[(1R,2S)-2-phenylcyclopropyl]amino}propanamide; 2-{[(1R,2S)-2-phenylcyclopropyl]amino}-N-prop-2-ynylacetamide; N-isopropyl-2-{[(1R,2S)-2-phenylcyclopropyl] amino}acetamide; N-(tert-butyl)-2-{[(1R,2S)-2-phenylcyclopropyl]amino}acetamide; N-(2-morpholin-4-yl-2-oxoethyl)-N-[(1R,2S)-2-phenylcyclopropyl]amine; 2-{[(1R,2S)-2-phenylcyclopropyl]amino}propanamide; Methyl 2-{[(1R,2S)-2-phenylcyclopropyl]amino}propanoate; N-cyclopropyl-2-{methyl[(1R,2S)-2-phenylcyclopropyl] amino}acetamide; 2-{methyl[(1R,2S)-2-phenylcyclopropyl] amino}acetamide; N-methyl-trans-2-(Phenylcyclopropylamino)propanamide; 1-(4-methylpiperazin-1-yl)-2-((1R,2S)-2-phenylcyclopropylamino)ethanone; 1-(4-ethylpiperazin-1-yl)-2-((1R,2S)-2-phenylcyclopropylamino)ethanone; 1-(4-benzylpiperazin-1-yl)-2-((1R,2S)-2-phenylcyclopropylamino)ethanone; 2-((1R,2S)-2-phenylcyclopropylamino)-1-(4-phenylpiperazin-1-yl)ethanone; 2-((1R,2S)-2-(4-(benzyloxy)phenyl)cyclopropylamino)-1-(4-methylpiperazin-1-yl)ethanone; 2-((1R,2S)-2-(4-(benzyloxy)phenyl)cyclopropylamino)-N-cyclopropylacetamide; 2-((1R,2S)-2-(4-(3-fluorobenzyloxy) phenyl)cyclopropylamino)-1-(4-methylpiperazin-1-yl)ethanone; 2-((1R,2S)-2-(4-(3-chlorobenzyloxy)phenyl) cyclopropylamino)-1-(4-methylpiperazin-1-yl)ethanone; 2-((1R,2S)-2-(biphenyl-4-yl)cyclopropylamino)-1-(4-methylpiperazin-1-yl)ethanone; 1-(4-methylpiperazin-1-yl)-2-((1R,2S)-2-(4-phenethoxyphenyl)cyclopropylamino)ethanone; 2-((1R,2S)-2-(4-(4-fluorobenzyloxy)phenyl) cyclopropylamino)-1-(4-methylpiperazin-1-yl)ethanone; and 2-((1R,2S)-2-(4-(biphenyl-4-ylmethoxy)phenyl)cyclopropylamino)-1-(4-methylpiperazin-1-yl)ethanone.

In one aspect, the invention provides a compound of Formula I or a pharmaceutically acceptable salt thereof wherein the compound is chosen from 2-({(1R,2S)-2-[4-(benzyloxy) phenyl]cyclopropyl}amino)-N-cyclopropylacetamide, N-[(1R,2S)-2-(4-benzyloxyphenyl)cyclopropyl]}-N-[2-(4-methylpiperazin-1-yl)-2-oxoethyl]amine, N-[2-oxo-2-(4-phenylpiperazin-1-yl)ethyl]-N-[(1R,2S)-2-phenylcyclopropyl]amine, N-[2-(4-benzylpiperazin-1-yl)-2-oxoethyl]-N-[(1R,2S)-2-phenylcyclopropyl]amine, N-[2-(4-ethylpiperazin-1-yl)-2-oxoethyl]-N-[(1R,2S)-2-phenylcyclopropyl]amine, N-[2-(4-methylpiperazin-1-yl)-2-oxoethyl]-N-[(1R,2S)-2-phenylcyclopropyl]amine, 2-((1R,2S)-2-(4-pyridin-3-ylphenyl)cyclopropylamino)-1-(4-methylpiperazin-1-yl)ethanone, and 2-((1R,S)-2-(3'-methoxy-1,1'-biphenyl-4-yl)cyclopropylamino)-1-(4-methylpiperazin-1-yl)ethanone.

DEFINITIONS

Any definition herein may be used in combination with any other definition to describe a composite structural group. By convention, the trailing element of any such definition is that which attaches to the parent moiety. For example, the composite group aryloxy would represent an aryl group attached to the parent molecule through an oxy (—O—) group, and the term arylalkyl would represent an aryl group attached to the parent molecule through an alkyl group. The definitions defined herein are intended as preferred definitions of the general art-accepted meaning.

As used herein, the term "alkyl" refers to a saturated aliphatic hydrocarbon including straight chain and branched chain groups. In a more specific definition, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). In another more specific definition, it is a medium size alkyl having 1 to 10 carbon atoms. In yet another more specific definition, it is a lower alkyl having 1 to 6 carbon atoms, and even more preferably 1 to 4 carbon atoms.

As used herein, the term "alkenyl" refers to an unsaturated (including partially unsaturated) straight and branched chain hydrocarbon having at one carbon carbon double bond. In a more specific definition, the alkenyl group is further defined as having from 2 to 20 carbons. In a more specific definition, the alkenyl group is further defined as having from 2 to 10 carbons. In a more specific definition, the alkenyl group is further defined as having from 2 to 6 carbons. In a more specific definition, the alkenyl group is further defined as having from 2 to 4 carbons.

As used herein, the term "alkynyl" refers to an unsaturated (including partially unsaturated) straight and branched chain hydrocarbon having at one carbon carbon triple bond. In a more specific definition, the alkynyl group is further defined as having from 2 to 20 carbons. In a more specific definition, the alkynyl group is further defined as having from 2 to 10 carbons. In a more specific definition, the alkynyl group is further defined as having from 2 to 6 carbons. In a more specific definition, the alkynyl group is further defined as having from 2 to 4 carbons.

As used herein, the term "acyl," refers to a carbonyl attached to an alkenyl, alkyl, aryl, cycloalkyl, heteroaryl, heterocyclyl, or any other moiety where the atom attached to the carbonyl is carbon.

As used herein, the term "acyloxy," refers to an acyl group attached to the parent moiety through an oxygen atom.

As used herein, the term "halo" refers to chloro, fluoro, bromo, and iodo.

As used herein, the term "hydro" refers to a hydrogen atom (—H group).

As used herein, the term "hydroxy" refers to an —OH group.

As used herein, the term "alkoxy" refers to both an —O-alkyl and an —O-cycloalkyl group, as defined herein. Lower alkoxy refers to —O-lower alkyl groups.

As used herein, the term "aryloxy" refers to both an —O-aryl and an —O-heteroaryl group, as defined herein.

As used herein, the term "mercapto" group refers to a —SH group.

As used herein, the term "alkylthio" group refers to an S-alkyl.

As used herein, the term "cycloalkylthio" refers to an —S-cycloalkyl group.

As used herein, the term "arylthio" group refers to an —S-aryl.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refer to a cycloalkyl group in which one of the carbon atoms which form the ring has a "=O" bonded to it; i.e. one of the ring carbon atoms is a —C(=O)-group.

As used herein, the term "thiocarbonyl" group refers to a —C(=S)R" group, with R" as defined herein.

As used herein, the term "O-carboxy" group refers to a R"C(=O)O-group, with R" as defined herein.

As used herein, the term "C-carboxy" group refers to a —C(=O)OR" groups with R" as defined herein.

As used herein, the term "ester" is a C-carboxy group, as defined herein, wherein R" is any of the listed groups other than hydro.

As used herein, the term "C-carboxy salt" refers to a —C(=O)O$^-$M$^+$ group wherein M$^+$ is selected from the group consisting of lithium, sodium, magnesium, calcium, potassium, barium, iron, zinc and quaternary ammonium.

As used herein, the term "acetyl" group refers to a —(C=O)CH$_3$ group.

As used herein, the term "carboxyalkyl" refers to —(CH$_2$)$_r$C(=O)OR" wherein r is 1-6 and R" is as defined above.

As used herein, the term "carboxyalkyl salt" refers to a —(CH$_2$)$_r$C(=O)O$^-$M$^+$ wherein M$^+$ is selected from the group consisting of lithium, sodium, potassium, calcium, magnesium, barium, iron, zinc and quaternary ammonium.

As used herein, the term "carboxylic acid" refers to a C-carboxy group in which R" is hydro.

As used herein, the term "cycloalkoxy" refers and O-cycloalkyl group.

As used herein, the term "haloalkyl" refers to an alkyl group substituted with 1 to 6 halo groups. In a specific embodiment, haloalkyl is a —CX$_3$ group wherein X is a halo group. The halo groups can be independently selected.

As used herein, the term "haloaryl" refers to an aryl group having the meaning as defined above wherein one or more hydrogens are replaced with a halogen.

As used herein, the term "heteroarylthio" refers to a —S—heteroaryl group.

As used herein, the term "trihalomethanesulfonyl" refers to a X$_3$CS(=O)$_2$— group with X as defined above.

As used herein, the term "cyano" refers to a —C≡N group.

As used herein, the term "cyanato" refers to a —CNO group.

As used herein, the term "isocyanato" refers to a —NCO group.

As used herein, the term "thiocyanato" refers to a —CNS group.

As used herein, the term "isothiocyanato" refers to a —NCS group.

As used herein, the term "sulfinyl" refers to a —S(=O)R" group, with R" as defined herein.

As used herein, the term "sulfonyl" refers to a —S(=O)$_2$R" group, with R" as defined herein.

As used herein, the term "sulfonamido" refers to a —S(=O)$_2$NR$_{17}$R$_{18}$, with R$_{17}$ and R$_{18}$ as defined herein (independently selected from the group consisting of hydro and lower alkyl).

As used herein, the term "trihalomethanesulfonamido" refers to a X$_3$CS(=O)$_2$NR$_{17}$— group with X and R$_{17}$ as defined herein.

As used herein, the term "O-carbamyl" refers to a —OC(=O)NR$_{17}$R$_{18}$ group with R$_{17}$ and R$_{18}$ as defined herein.

As used herein, the term "N-carbamyl" refers to a R$_{18}$OC(=O)NR$_{17}$— group, with R$_{17}$ and R$_{18}$ as defined herein.

As used herein, the term "O-thiocarbamyl" refers to a —OC(=S)NR$_{17}$R$_{18}$ group with R$_{17}$ and R$_{18}$ as defined herein.

As used herein, the term "N-thiocarbamyl" refers to a R$_{17}$O(C=S)NR$_{18}$— group, with R$_{17}$ and R$_{18}$ as defined herein.

As used herein, the term "amino" refers to an —NRR group, with R and R both being hydro.

As used herein, the term "C-amido" refers to a —C(=O)NR$_{17}$R$_{18}$ group with R$_{17}$ and R$_{18}$ as defined herein.

An "N-amido" refers to a R$_{17}$C(=O)NR$_{18}$— group with R$_{17}$ and R$_{18}$ as defined herein.

As used herein, the term "nitro" refers to a —NO$_2$ group.

As used herein, the term "quaternary ammonium" refers to a —NR$_{17}$R$_{18}$R$_{19}$ group wherein R$_{17}$, R$_{18}$, and R$_{19}$ are independently selected from the group consisting of hydro and lower alkyl.

As used herein, the term "methylenedioxy" refers to a —OCH$_2$O— group wherein the oxygen atoms are bonded to adjacent ring carbon atoms.

As used herein, the term "ethylenedioxy" refers to a —OCH$_2$CH$_2$O— group wherein the oxygen atoms are bonded to adjacent ring carbon atoms.

As used herein, the term "carbocycle," "carbocyclic" or "carbocyclyl" refers to an all-carbon monocyclic or fused ring (i.e., rings which share an adjacent pair of ring carbon atoms) group wherein one or more of the rings does not have a completely conjugated pi-electron system. Examples, without limitation, of carbocyclic groups are "cycloalkyls" such as cyclopropane, cyclobutane, cyclopentane, cyclohexane, adamantane, cycloheptane and cycloalkenes such as cycloheptatriene, cyclopentene, and cyclohexadiene.

As used herein, the term "heterocyclyl," "heterocyclyl" or "heterocyclic" refers to a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocyclyls" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocyclyl" can include heteroaryls when the pi-electron system of a heterocyclyl is completely conjugated.

As used herein, the term "aryl" refers to an all-carbon monocyclic or fused-ring polycyclic (i.e., rings which share an adjacent pair of ring carbon atoms) aromatic group having a completely conjugated pi-electron system. Examples, without limitation, of aryl groups are phenyl, naphthalenyl and anthracenyl.

As used herein, the term "heteroaryl" refers to a monocyclic or fused ring polycyclic group having 5 to 14 ring atoms; 6, 10 or 14 pi electrons shared in a cyclic array; and containing carbon atoms and 1, 2 or 3 heteroatoms independently selected from the group consisting of O, N, and S. In a more specific definition, it refers to a monocyclic or fused-ring polycyclic aromatic group having from 5 to 9 ring atoms and comprising 1, 2, or 3 heteroatoms independently selected from the group consisting of O, N, and S, Non-limiting examples of heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2 oxobenzimidazolyl. When the heteroaryl group contains a nitrogen ring atom, such nitrogen ring atom may be in the form of an N-oxide, e.g., a pyridyl N-oxide, pyrazinyl N-oxide and pyrimidinyl N-oxide.

As used herein, the term "arylalkyl" refers to any of the $C_{1-10}$ alkyl groups substituted by any of the above-mentioned $C_{6-14}$ aryl groups as defined herein. Non-limiting examples of arylalkyl group include benzyl, phenethyl, and naphthylmethyl.

As used herein, the term "arylalkenyl" is used herein to mean any of the above-mentioned $C_{2-10}$ alkenyl groups substituted by any of the above-mentioned $C_{6-14}$ aryl groups.

As used herein, the term "arylalkynyl" refers to any of $C_{2-10}$ alkynyl groups substituted by any of the above-mentioned $C_{6-14}$ aryl groups as defined herein.

As used herein, the term "arylalkoxy" refers to any of the $C_{1-10}$ alkoxy groups substituted by any of the aryl groups as defined herein. Examples of arylalkoxy groups include benzyloxy and phenethyloxy.

As used herein, the term "aryloxy" refers to oxygen substituted by any of the $C_{6-14}$ aryl groups defined herein. Examples of aryloxy groups include phenoxy and phenethoxy.

As used herein, the term "arylthio" group refers to a —S-aryl.

As used herein, the term "acyl" refers to a carbonyl attached to an alkenyl, alkyl, aryl, cycloalkyl, heteroaryl, heterocyclyl, or any other moiety where the atom attached to the carbonyl is carbon.

As used herein, the term "acylamino" refers to an acyl group attached to the parent moiety through an amino group.

As used herein, the term "acyloxy" refers to an acyl group attached to the parent moiety through an oxygen atom.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder" refers to a slowing of or a reversal of the progress of the disease. Treating a disease or disorder includes treating a symptom and/or reducing the symptoms of the disease.

As used herein, the term "preventing a disease or disorder" refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula I, which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

As used herein, the term "dose" or "dosage" refers the amount of active ingredient that an individual takes or is administered at one time. For example, a 40 mg dose of a compound of Formula I refers to, in the case of a twice-daily dosage regimen, a situation where the individual takes 40 mg of a compound of Formula I twice a day, e.g., 40 mg in the morning and 40 mg in the evening. The 40 mg of a compound of Formula I dose can be divided into two or more dosage units, e.g., two 20 mg dosage units of a compound of Formula I in tablet form or two 20 mg dosage units of a compound of Formula I in capsule form.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formula I (and the compounds of Formula I(a)) can contain asymmetric carbon atoms and can therefore exist in racemic and optically active forms. Thus, optical isomers or enantiomers, racemates, tautomers, and diastereomers are also encompassed in the compounds of Formula I (and the compounds of Formula I(a)). The methods of present invention include the use of all such isomers and mixtures thereof. Methods of separation of enantiomeric and diastereomeric mixtures are well known to one skilled in the art. The present invention encompasses any isolated racemic or optically active form of compounds described in Formula I (and the compounds of Formula I(a)), or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula I (and the compounds of Formula I(a)) have the trans configuration.

Typically, compounds according to Formula I (and the compounds of Formula I(a)) can be effective at an amount of from about 0.01 μg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 μg to about 2000 mg, preferably from about 5 μg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) *J. Pharmaceut. Sci.,* 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer: itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, anti-thrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

General Synthetic Route Description

The compounds of Formula (I) can be synthesized by the general route described in Schemes 1, 2, 3 and 4.

SCHEME 1: DCM (dichloromethane); DIPEA (diisopropylethylamine)

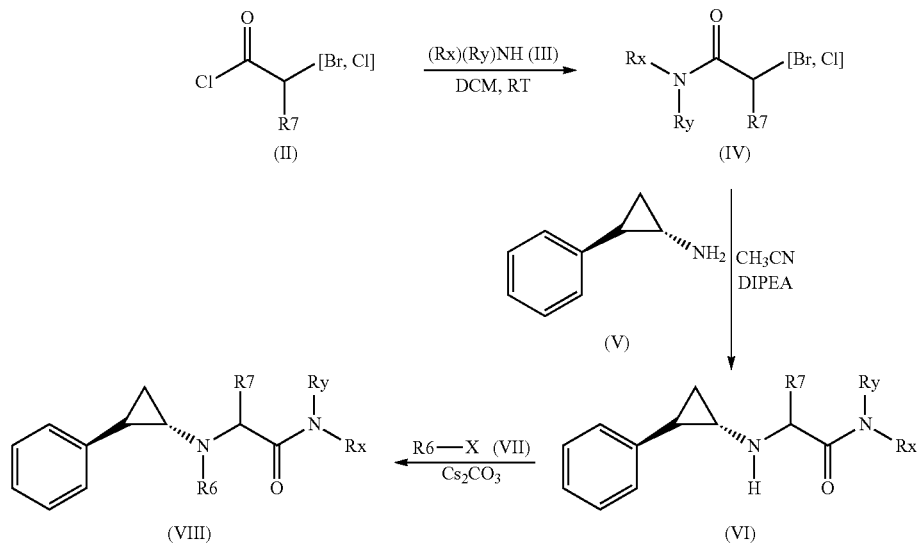

The reaction of commercially available bromoacylchlorides or chloroacylchlorides of formula (II) with commercially available amines of formula (III) at room temperature using dichloromethane as a solvent leads the bromoacyl or chloroacyl derivatives of formula (IV) in high yield. These bromoacyl or chloroacyl derivatives of formula (IV) reacts with commercially available phenylcyclopropylamine derivatives of formula (V) (both cis ((1S,2S) (1R,2R)) and trans ((1S,2R), (1R,2S)) versions as well the individual diastereoisomers corresponding to (1S,2S), (1S,2R), (1R,2S) and (1R,2R) can be used) using acetonitrile as a solvent and diisopropylethylamine as a base resulting in the formation of the derivatives of formula (VI), which are subject of the present invention. The Examples below were synthesized using trans phenylcyclopropylamines of formula (V). Alkylation of the compounds of formula (VI) using commercially available alkylating agent of formula (VII), where —X represents a good leaving group like an halogen atom, and cesium carbonate as a base results in the formation of the derivatives of formula (VIII) which are also subject of the present invention as defined above.

On the other hand, the compounds of formula (I), where R8 is defined as —C(O)R$_z$ can be synthesized in an analogous manner as described in scheme 2.

SCHEME 2

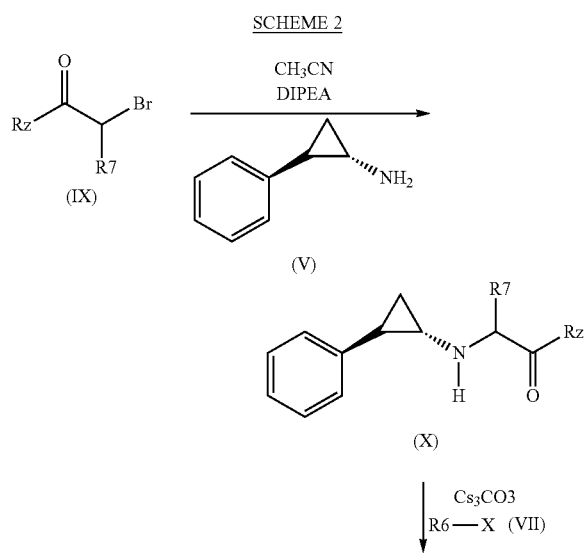

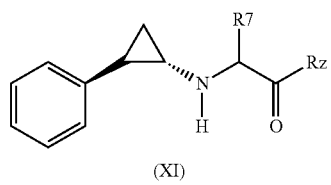

(XI)

The reaction of commercially available bromoesters and bromoketones of formula (IX) with commercially available phenylcyclopropylamine derivatives of formula (V) (including both cis ((1S,2S) (1R,2R)) and trans ((1S,2R), (1R,2S)) versions as well the individual diastereoisomers corresponding to (1S,2S), (1S,2R), (1R,2S) and (1R,2R) can be used) using acetonitrile as a solvent and diisopropylethylamine as a base resulting in the formation of the derivatives of formula (X), which are subject of the present invention. The Examples below were synthesized using trans phenylcyclopropylamines of formula (V). Alkylation of the compounds of formula (X) using commercially available alkylating agent of formula (VII), where —X is a good leaving group like halogen, and cesium carbonate as a base results in the formation of the derivatives of formula (XI) which are also subject of the present invention as defined above.

The derivatives containing a Phenylcyclopropyl group substituted at the phenyl moiety (R different from a hydrogen atom in scheme 3) can be synthesized following the general route described in scheme 3.

SCHEME 3

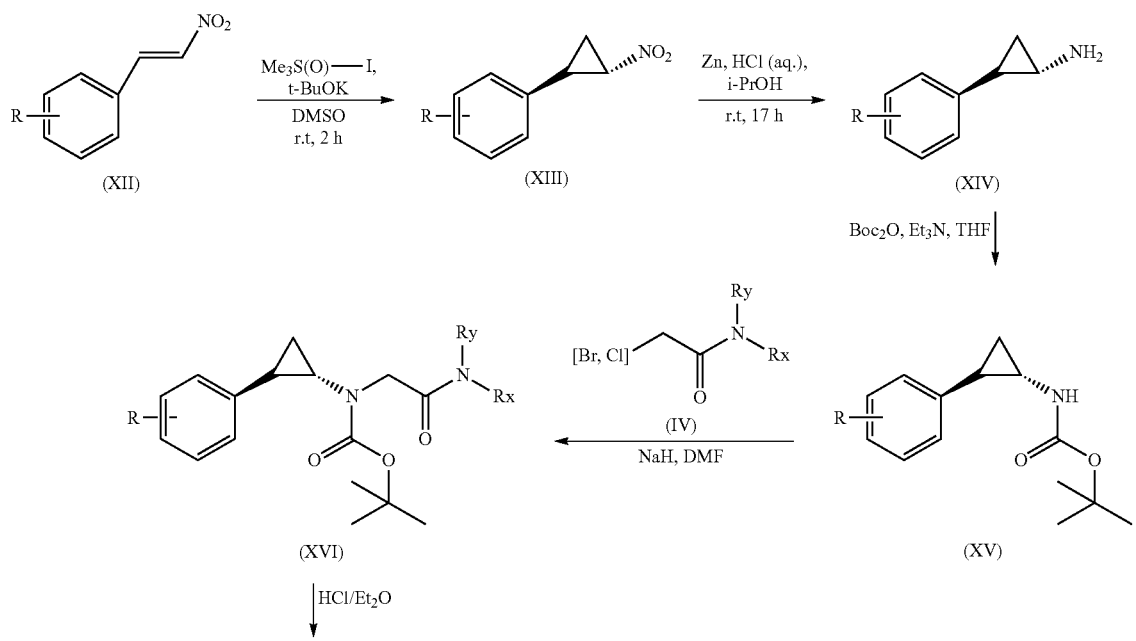

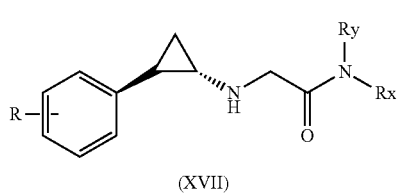

(XVII)

Commercially availables nitrostyrene of formula (XII) have been subjected to a cyclopropanation reaction using trimetilsulfoxonium iodide and potassium tertbutylate. The nitro group of the resulted nitrocyclopropyl derivatives of formula (XIII) has been then reduced using zinc in hydrochloric acid to afford the cyclopropylamino derivatives of formula (XIV). These compounds of formula (XIV) (both cis diate of formula (XV) in high yield. Alkylation of the derivatives of formula (XV) with the derivatives of formula (IV) described earlier, using NaH as a base and DMF as a solvent, lead to the intermediates of formula (XVI). Deprotection of the Boc-group using HCl in $Et_2O$ lead to the formation of derivatives of formula (XVII), which are also subjects of the present invention.

SCHEME 4

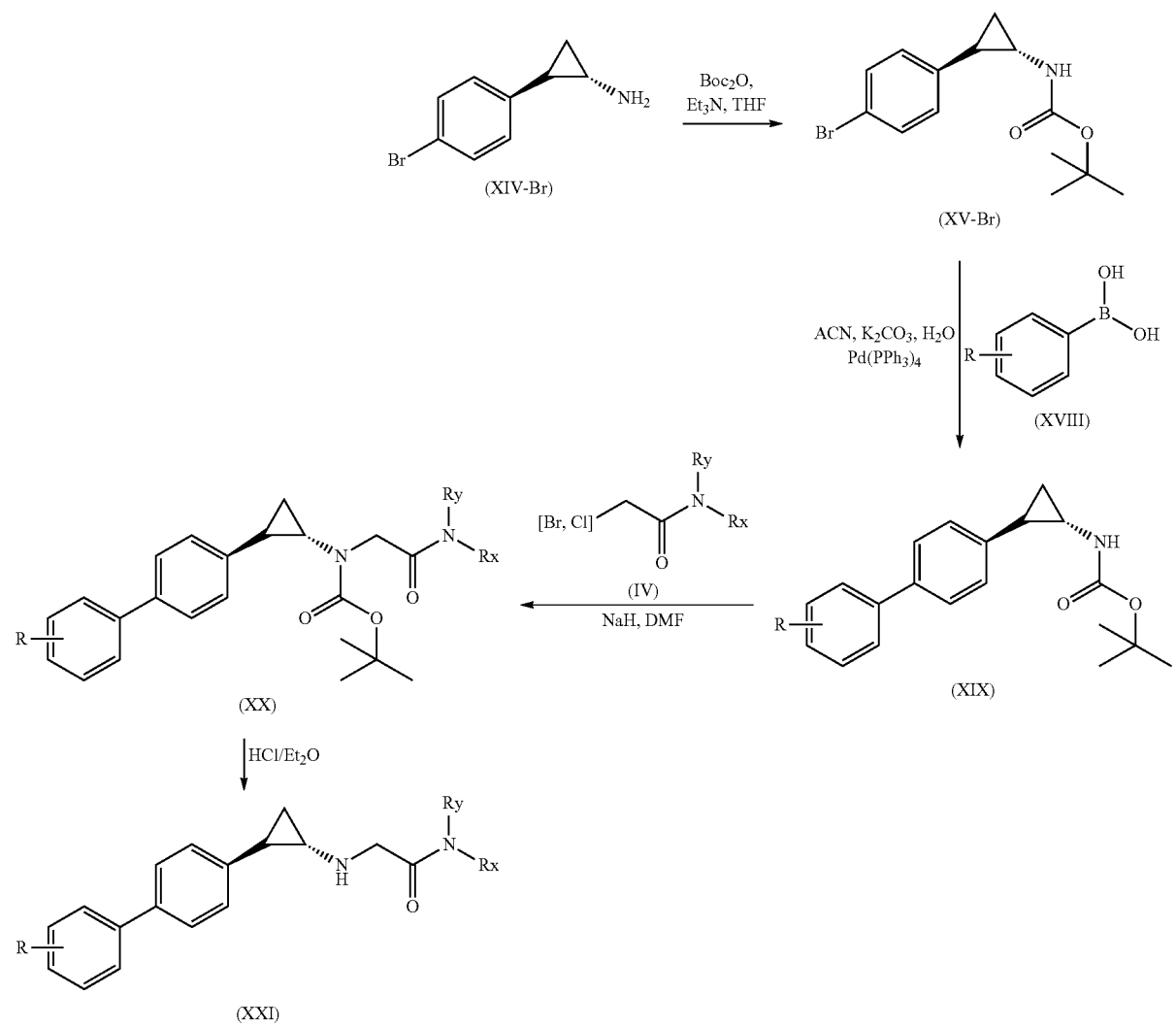

((1S,2S) (1R,2R)) and trans ((1S,2R), (1R,2S)) versions as well the individual diastereoisomers corresponding to (1S, 2S), (1S,2R), (1R,2S) and (1R,2R) can be used) react with t-butyl dicarbonate at room temperature using triethylamine as a base and dichloromethane as a solvent leading interme- The reaction of intermediate E (XIV-Br) (both cis ((1S,2S) (1R,2R)) and trans ((1S,2R), (1R,2S)) versions as well the individual diastereoisomers corresponding to (1S,2S), (1S, 2R), (1R,2S) and (1R,2R) can be used) with 1-butyl dicarbonate at room temperature using triethylamine as a base and tetrahydrofuran as a solvent leads to the formation of the compounds of formula (XV-Br) in high yield. These boc-protected derivatives (XV-Br) react with commercially available boronic acid derivatives of formula (XVIII) using acetonitrile as a solvent, potassium carbonate as a base and tetrakis (triphenylphospine) paladium (0) as a catalyst resulting in the formation of the derivatives of formula (XIX). Alkylation with bromoacyl or chloroacyl derivatives of formula (IV), using NaH as a base and DMF as a solvent lead to the formation of the compounds of formula (XX). Deprotection of the Boc-group using HCl in Et$_2$O results in the formation of the derivatives of formula (XXI) which are also subjects of the present invention.

EXAMPLES

The program used to generate the names corresponding to the structures in the Example compounds below was MDL ISIS Draw 2.5 (using the ACD/Name for ISIS Draw add-in). This program named the molecules as the (1S,2R) configuration due to the configuration of the input structure and the "trans" term has been substituted in the place of the (1S,2R) term specified by the program. The structures depicted below for the Example compounds below are shown as having one particular stereochemical configuration around the cyclopropyl carbon atoms of the phenylcyclopropylamine core (1S, 2R). All the compounds synthesized in the Examples are mixtures having both configurations (1R,2S) and (1S,2R), that is to say they are "trans" in respect to the cycloproyl ring of the cyclopropyl ring system. This is due to the fact the phenylcyclopropylamine starting material used is "trans." It is contemplated that the cis configuration starting material or the individual diastereomers/enantiomers could be used as starting material, all of which are either commercially or synthetically available. Thus, the invention relates to compounds of Formula I, I(a), and those of the examples that have specific stereochemical configurations around the cyclopropyl ring e.g., trans ((1R,2S) and (1S,2R)) and cis (1R,2R) and (1S,2S). A preferred stereochemical configuration around the cyclopropyl ring of phenylcyclopropylamine is trans.

The compounds of the examples can also be synthesized or provided in a salt form. The skilled artisan is aware and capable of making salt forms and/or converting salt forms of the compounds of the invention, e.g., compounds of Formula I, I(a), and those of the Examples. In some cases the compounds of Formula I, I(a), and the Examples can be more stable as salt forms as compared to free base.

In reference to the synthetic schemes described herein the following intermediates (and analogous intermediates or derivatives thereof) can be made using the following procedures.

In reference to the chemical structures and names used herein, if there is a conflict between the structure and the name, the structure controls (i.e., drawing).

Intermediate A: 1-(benzyloxy)-4-[(trans)-2-nitrocyclopropyl]benzene

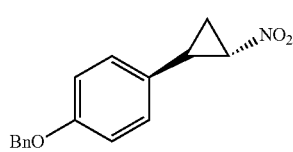

Trimethylsulfoxonium iodide (0.62 g, 2.82 mmol) was added in portions to a solution of t-BuOK (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with Et$_2$O (3×10 mL); the organic layers were washed with brine (2×15 mL), dried over anhydrous Na$_2$SO$_4$ and filtered. After removal of the solvent, the residual orange oil was purified by column chromatography on silica gel (5% EtOAc/hexanes) affording 0.16 g of 1-(benzyloxy)-4-[(1R,2S)-2-nitrocyclopropyl]benzene [Rf=0.5 (20% EtOAc/hexanes), white solid, 26% yield].

Intermediate B:
(Trans)-2-[4-(benzyloxy)phenyl]cyclopropanamine

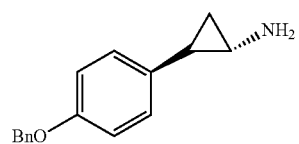

Zn dust (1.97 g, 30 mol) was added in small portions, over a period of 30 min, to a vigorously stirred solution of 1-(benzyloxy)-4-[(1R,2S)-2-nitrocyclopropyl]benzene (Intermediate A, 0.81 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with CH$_2$Cl$_2$ (3×15 mL). The organic layers were dried over anhydrous Na$_2$SO$_4$ and filtered. After removal of the solvent, the crude product was purified by column chromatography on silica gel (10% MeOH/CH$_2$Cl$_2$) affording 0.50 g of (trans)-2-[4-(benzyloxy) phenyl]cyclopropanamine [Rf=0.2 (10% MeOH/CH$_2$Cl$_2$), white solid, 70% yield].

$^1$H NMR δ (ppm): MeOH 400 MHz: 7.45-7.27 (m, 5H, ArH); 6.96 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate C: Terbutyl(trans)-2-[4-(benzyloxy) phenyl]cyclopropylcarbamate

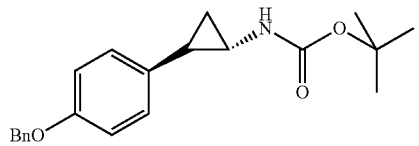

Boc$_2$O (1.65 equiv) was added to a solution of (Trans)-2-[4-(benzyloxy)phenyl]cyclopropanamine (Intermediate B; 1 equiv.) and Et$_3$N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na$_2$SO$_4$ and filtered; after removal of the solvent, the residue was purified by column chromatography on silica gel (10-20% EtOAc/Hexanes), affording the target compound (Yield 78%).

¹H NMR δ (ppm): MeOH 400 MHz: 7.45-7.27 (m, 5H, ArH); 6.93 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 10H, CH; tBu); 0.98-0.85 (m, 2H, CH2).

Intermediate D:
1-bromo-4-[(trans)-2-nitrocyclopropyl]benzene

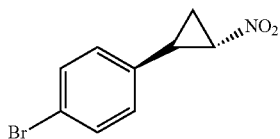

This compound was synthesized using the same methodology described in Intermediate A, using the commercially available 1-bromo-4-[(trans)-2-nitrovinyl]benzene as starting material. 27% yield Intermediate E:
(trans)-2-(4-bromophenyl)cyclopropanamine

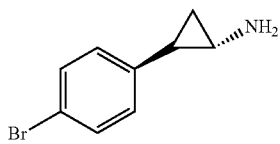

This compound was synthesized using the same methodology described in Intermediate B, using as starting material 1-bromo-4-[(trans)-2-nitrocyclopropyl]benzene. 10% yield. 1HNMR (CD3OD): 1.45 (m, 2H), 2.61 (m, 1H), 2.86 (m, 1H), 6.98 (d, 2H), 7.11 (d, 2H). MS (M+H): 211.9

Intermediate F: Tert-butyl(trans)-2-(4-bromophenyl)cyclopropylcarbamate

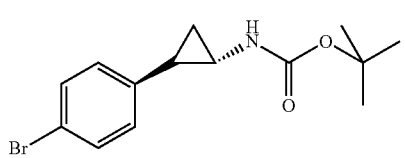

This compound was synthesized using the same methodology described in Intermediate C, using as starting material (trans)-2-(4-bromophenyl)cyclopropanamine (Yield 85%) 1HNMR (CDCl3): 1.13 (m, 2H), 1.45 (s, 9H), 2.02 (m, 1H), 2.72 (m, 1H), 7.01 (d, 2H), 7.36 (d, 2H). MS (M+H): 312.2.

Example 1

N-cyclopropyl-2-{[(trans)-2-phenylcyclopropyl]amino}acetamide

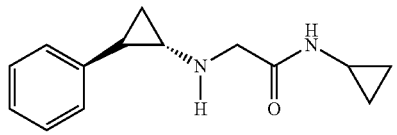

Bromoacetylchloride (450 mg, 3 mmol) was dissolved in acetonitrile (15 mL) and the solution was cooled to 0° C. To this solution cycloproylamine (170 mg, 3 mmol) was added and the mixture stirred at room temperature for 2 h. To this solution trans-phenylcyclopropyl amine hydrochloride (0.50 g, 2.95 mmol) and diisoproylethylamine (1.25 mL, 7.37 mmol) were successively added and the mixture stirred at room temperature for 16 h. The mixture was then concentrated in vacuo and the residue was purified by flash column chromatography (DCM:MeOH, 25:1) to afford the titled compound as a white solid (0.21 g, 59%). 1H NMR δ (ppm): 0.41 (m, 2H), 0.77 (m, 2H), 1.03 (m, 2H), 1.98 (m, 3H), 2.40 (m, 1H), 2.78 (m, 1H), 3.38 (s, 2H), 6.99 (m, 3H), 7.22 (m, 3H). MS (M+H): 230.7.

The following compounds can be synthesized following the method described for example 1 using the corresponding starting materials.

Example 2

2-{[(trans)-2-phenylcyclopropyl]amino}acetamide

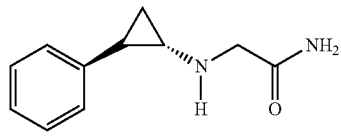

1HNMR δ (ppm): 1.05 (m, 2H), 1.92 (m, 2H), 2.45 (m, 1H), 3.41 (s, 2H), 5.58 (bd, 1H), 6.78 (bs, 1H), 7.05 (m, 2H), 7.22 (m, 3H). MS (M+H): 191.4.

Example 3

N-cyclopropyl-2-{[(trans)-2-phenylcyclopropyl]amino}propanamide

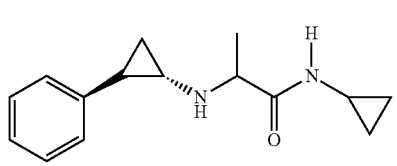

1HNMR (CDCl3) δ (ppm): 0.49 (d, 2H), 0.78 (t, 2H), 1.04 (m, 2H), 1.31 (d, 3H), 1.84 (s, 1H), 1.89 (m, 2H), 2.36 (m, 1H), 2.71 (m, 1H), 3.31 (q, 1H), 6.89 (b, 1H), 7.00 (d, 2H), 7.18 (q, 1H), 7.27 (t, 2H). MS (M+H): 244.9.

Example 4

2-{[(trans)-2-phenylcyclopropyl]amino}-N-prop-2-ynylacetamide

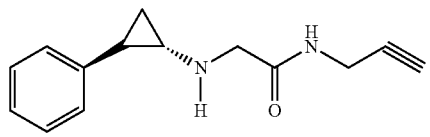

1HNMR δ (ppm): 1.05 (m, 2H), 1.96 (m, 2H), 2.24 (m, 1H), 2.41 (m, 1H), 3.42 (s, 2H), 4.08 (m, 2H), 7.01 (m, 2H), 7.22 (m, 3H). MS (M+H): 228.9.

Example 5

N-isopropyl-2-{[(trans)-2-phenylcyclopropyl]amino}acetamide

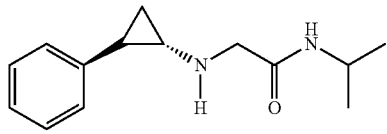

1HNMR δ (ppm): 1.15 (m, 8H), 1.95 (m, 2H), 2.05 (bs, 1H), 2.40 (m, 1H), 3.38 (s, 2H), 4.10 (m, 1H), 6.78 (bs, 1H), 7.05 (m, 2H), 7.22 (m, 3H). MS (M+H): 233.5.

Example 6

N-(tert-butyl)-2-{[(trans)-2-phenylcyclopropyl]amino}acetamide

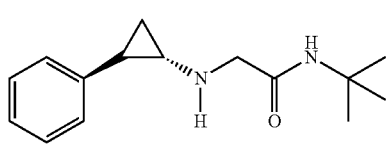

1HNMR δ (ppm): 1.17 (m, 2H), 1.36 (s, 3H), 1.95 (m, 1H), 2.45 (m, 1H), 3.30 (s, 2H), 6.78 (bs, 1H), 7.05 (m, 2H), 7.22 (m, 3H). MS (M+H): 246.8.

Example 7

N-(2-morpholin-4-yl-2-oxoethyl)-N-[(trans)-2-phenylcyclopropyl]amine

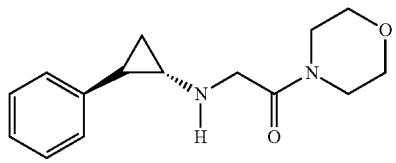

1HNMR δ (ppm): 0.96 (m, 1H), 1.92 (m, 1H), 2.45 (m, 1H), 3.41 (m, 2H), 3.45 (s, 2H), 3.65 (m, 6H), 7.05 (m, 2H), 7.22 (m, 3H). MS (M+H): 261.3.

Example 8

N-(4-fluorophenyl)-2-{[(trans)-2-phenylcyclopropyl]amino}acetamide

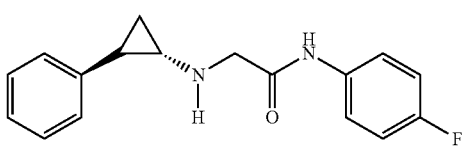

1HNMR δ (ppm): 1.17 (m, 2H), 2.05 (m, 1H), 2.45 (m, 1H), 3.48 (s, 2H), 7.05 (m, 4H), 7.22 (m, 4H), 7.56 (m, 2H), 8.89 (bs, 1H). MS (M+H): 285.1.

Example 9

2-{[(trans)-2-phenylcyclopropyl]amino}propanamide

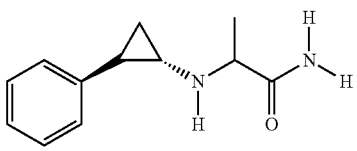

1HNMR δ (ppm): 1.05 (m, 2H), 1.38 (d, 2H), 1.92 (m, 2H), 2.45 (m, 1H), 3.41 (s, 2H), 5.58 (bd, 1H), 6.78 (bs, 1H), 7.05 (m, 2H), 7.22 (m, 3H). MS (M+H): 205.3.

Example 10

Methyl 2-{[(trans)-2-phenylcyclopropyl]amino}propanoate

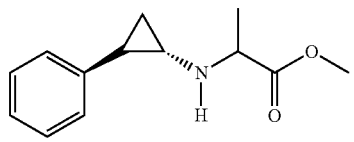

1HNMR δ (ppm): 1.05 (m, 2H), 1.28 (m, 3H), 1.90 (m, 3H), 2.35 (m, 1H), 3.55 (m, 1H), 3.78 (d, 3H), 7.02 (m, 2H), 7.22 (m, 3H). MS (M+H): 219.8.

Example 11

2-((trans)-2-phenylcyclopropylamino)-N-(piperidin-4-ylmethyl)acetamide dihydrochloride

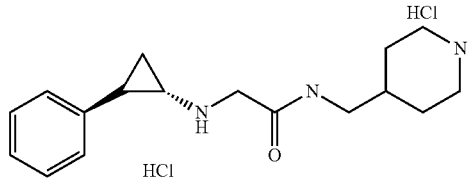

1HNMR (CDCl3) δ (ppm): 1.01 (m, 7H), 3.02 (m, 10H), 4.88 (bs, 1H), 6.98 (d, 2H), 7.18 (m, 5H), 9.00 (m, 2H), 9.68 (bs, 1H). MS (M+H): 288.1

Example 12

N-(1-(dimethylamino)propan-2-yl)-2-((trans)-2-phenylcyclopropylamino)acetamide dihydrochloride

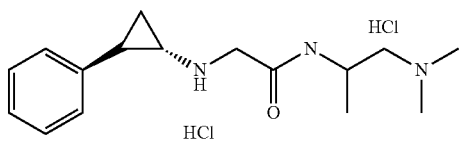

1HNMR (CDCl3) δ (ppm): 1.03 (d, 3H), 1.4 (m, 1H), 2.84 (m, 6H), 4.20 (m, 5H), 7.20 (m, 5H), 8.90 (bs, 1H), 9.88 (bs, 1H). MS (M+H): 276.1

Example 13

N-(2-(dimethylamino)ethyl)-2-((trans)-2-phenylcyclopropylamino)acetamide

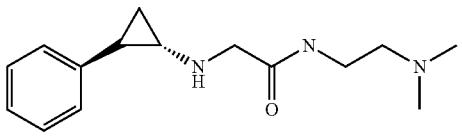

1HNMR (CDCl3) δ (ppm): 1.4 (m, 2H), 2.84 (m, 6H), 4.20 (m, 5H), 7.20 (m, 5H), 8.90 (bs, 1H), 9.88 (bs, 1H). MS (M+H): 262.3

Example 14

1-((S)-3-(dimethylamino)pyrrolidin-1-yl)-2-((trans)-2-phenylcyclopropylamino)ethanone dihydrochloride

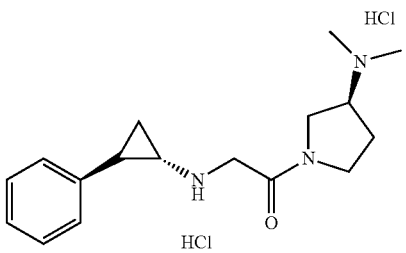

1HNMR (CDCl3) δ (ppm): 0.98 (m, 1H), 1.01 (m, 1H), 1.98 (m, 1H), 2.20 (m, 1H), 2.42 (m, 1H), 3.02 (m, 2H), 3.21 (m, 6H), 3.60 (s, 6H), 4.23 (bs, 2H), 7.05 (m, 2H), 7.18 (m, 3H). MS (M+H): 288.11

Example 15

1-((R)-3-(dimethylamino)pyrrolidin-1-yl)-2-((trans)-2-phenylcyclopropylamino)ethanone dihydrochloride

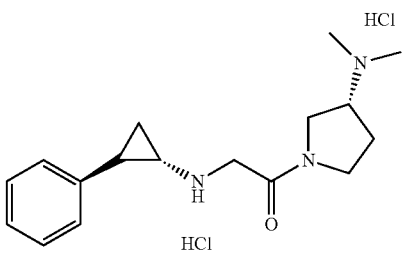

1HNMR (CDCl3) δ (ppm): 0.99 (m, 1H), 1.01 (m, 1H), 1.98 (m, 1H), 2.20 (m, 1H), 2.42 (m, 1H), 3.02 (m, 2H), 3.21 (m, 6H), 3.60 (s, 6H), 4.23 (bs, 2H), 7.05 (m, 2H), 7.18 (m, 3H). MS (M+H): 288.11

Example 16

1-((S)-3-aminopyrrolidin-1-yl)-2-((trans)-2-phenyl-cyclopropylamino)ethanone dihydrochloride

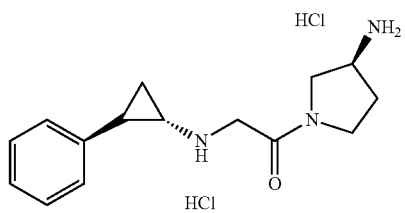

1HNMR (CDCl3) δ (ppm): 0.93 (m, 1H), 1.01 (m, 1H), 1.98 (m, 1H), 2.20 (m, 1H), 2.42 (m, 1H), 3.02 (m, 2H), 3.60 (s, 6H), 4.23 (bs, 4H), 7.05 (m, 2H), 7.18 (m, 3H). MS (M+H): 260.02

Example 17

2-((trans)-2-phenylcyclopropylamino)-N—((R)-pyrrolidin-3-yl)acetamide

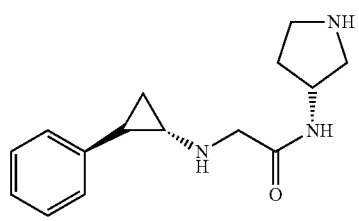

1HNMR (CDCl3) δ (ppm): 1.02 (m, 2H), 1.98 (m, 1H), 2.20 (m, 1H), 2.42 (m, 1H), 3.02 (m, 2H), 3.21 (m, 6H), 3.60 (s, 6H), 4.23 (bs, 2H), 7.05 (m, 2H), 7.18 (m, 3H). MS (M+H): 259.96

Example 18

2-((trans)-2-phenylcyclopropylamino)-N—((R)-pyrrolidin-3-yl)acetamide dihydrochloride

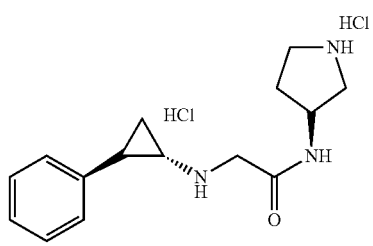

1HNMR (CDCl3) δ (ppm): 1.02 (m, 2H), 1.98 (m, 1H), 2.20 (m, 1H), 2.42 (m, 1H), 3.02 (m, 2H), 3.21 (m, 6H), 3.60 (s, 6H), 4.23 (bs, 2H), 7.05 (m, 2H), 7.18 (m, 3H). MS (M+H): 259.96

Example 19

N-cyclopropyl-2-{methyl[(trans)-2-phenylcyclopropyl]amino}acetamide

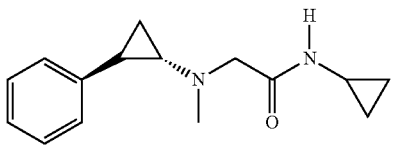

To a solution of N-cyclopropyl-N-methyl-trans-2-(phenylcyclopropyl amino)acetamide (example 1, 240 mg, 1 mmol) in acetonitrile (10 mL), methyl iodide (140 mg, 1 mmol) was added and the solution was refluxed for 1 h. The mixture was then concentrated in vacuo and the residue was purified by flash column chromatography (DCM:MeOH, 10:1) to afford the title compound as a white solid (200 mg, 57%). 1HNMR (CDCl3) δ (ppm): 0.44 (s, 2H), 0.73 (dd, 2H), 0.93 (m, 1H), 1.02 (m, 1H), 1.89 (m, 1H), 2.04 (m, 1H), 2.29 (s, 3H), 2.67 (m, 1H), 3.13 (m, 2H), 6.84 (br, 1H), 6.98 (d, 2H), 7.11 (q, 1H), 7.14 (m, 2H), 7.18 (d, 2H). MS (M+H): 244.7.

The following compounds can be synthesized following the method described for example 11 using the corresponding example and alkylating agent as starting materials.

Example 20

2-{methyl[(trans)-2-phenylcyclopropyl]amino}acetamide

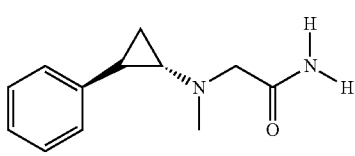

1HNMR δ (ppm): 1.05 (m, 2H), 2.02 (m, 1H), 2.14 (m, 1H), 2.42 (s, 3H), 3.21 (s, 2H), 5.78 (bd, 1H), 6.88 (bs, 1H), 7.01 (m, 2H), 7.22 (m, 3H). MS (M+H): 204.8.

Example 21

2-(benzyl((trans)-2-phenylcyclopropyl)amino)-N-tert-butylacetamide

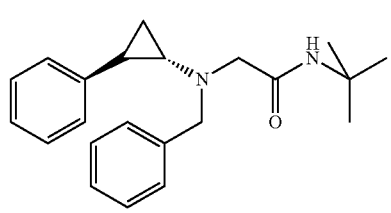

1HNMR (CDCl3) δ (ppm): 1.02 (m, 1H), 1.09 (m, 1H), 1.29 (s, 9H), 1.92 (m, 1H), 2.22 (m, 1H), 3.22 (d, 2H), 3.76 (d, 2H), 6.80 (br, 1H), 6.89 (d, 2H), 7.26 (m, 8H). MS (M+H): 337.4.

Example 22

1-(4-methylpiperazin-1-yl)-2-((trans)-2-phenylcyclopropylamino)ethanone

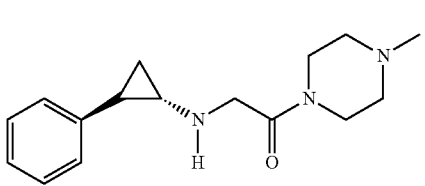

1HNMR (CDCl3) δ (ppm): 0.93 (q, 1H), 1.13 (quin, 1H), 1.93 (m, 1H), 2.04 (br, 2H), 2.31 (s, 2H), 2.40 (m, 3H), 2.44 (m, 1H), 3.40 (t, 2H), 3.53 (s, 2H), 3.66 (t, 2H), 7.04 (d, 2H), 7.18 (d, 1H), 7.24 (d, 2H). MS (M+H): 274.0.

Example 23

1-(4-ethylpiperazin-1-yl)-2-((trans)-2-phenylcyclopropylamino)ethanone

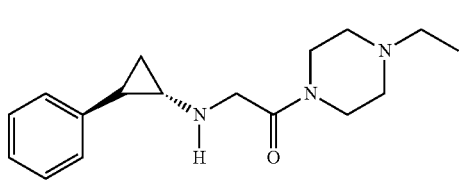

1HNMR (D2O) δ (ppm): 1.29 (t, 3H), 1.40 (q, 1H), 1.53 (m, 1H), 2.58 (m, 1H), 3.07 (m, 3H), 3.18 (m, 1H), 3.22 (q, 2H), 3.51 (d, 1H), 3.62 (d, 2H), 3.96 (d, 1H), 4.36 (d, 2H), 4.53 (d, 1H), 7.18 (d, 2H), 7.33 (m, 3H). MS (M+H): 288.3.

Example 24

1-(4-benzylpiperazin-1-yl)-2-((trans)-2-phenylcyclopropylamino)ethanone

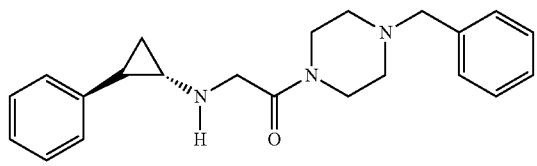

1HNMR (D2O) δ (ppm): 1.40 (q, 1H), 1.53 (m, 1H), 2.58 (m, 1H), 3.01 (m, 1H), 3.11 (m, 3H), 3.56 (d, 3H), 3.96 (d, 1H), 4.33 (d, 1H), 4.36 (s, 2H), 4.44 (d, 1H), 4.53 (d, 1H), 7.18 (d, 2H), 7.31 (m, 3H), 7.49 (s, 5H). MS (M+H): 350.2

Example 25

2-((trans)-2-phenylcyclopropylamino)-1-(4-phenylpiperazin-1-yl)ethanone

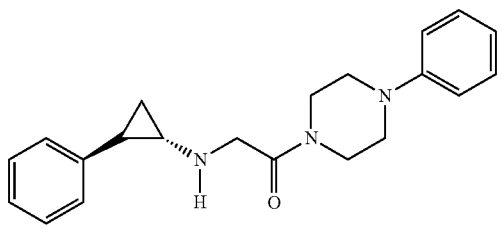

¹HNMR (D2O) δ (ppm): 1.39 (q, 1H), 1.52 (m, 1H), 2.56 (m, 1H), 3.02 (m, 1H), 3.15 (m, 3H), 3.96 (d, 1H), 4.43 (d, 1H), 4.46 (s, 2H), 4.56 (d, 1H), 4.63 (d, 1H), 7.18 (d, 2H), 7.32 (m, 3H), 7.51 (m, 5H). MS (M+H): 336.2.

Example 26

2-((trans)-2-(4-(benzyloxy)phenyl)cyclopropylamino)-1-(4-methylpiperazin-1-yl)ethanone

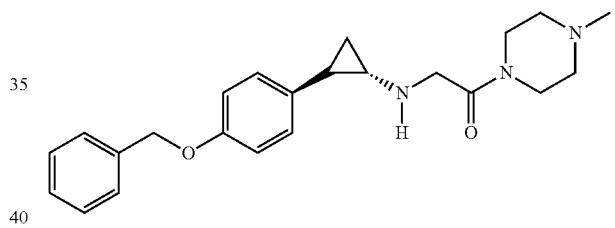

To a suspension of 1.5 equiv of NaH in dry DMF (10 vols) at 0° C. was added a solution of ter-butyl(trans)-2-[4-(benzyloxy)phenyl]cyclopropylcarbamate (Intermediate C, 1 equiv) in dry DMF (2 vols) and stirr for 30 mins. Then, added was a solution of 1-(chloroacetyl)-4-methylpiperazine (1.5 equiv) in dry DMF (10 mL) at 0° C., stirred for 1 h at 0° C. to RT. The progress of the reaction was monitored by TLC. After completion, reaction mixture was poured into ice water and extracted with EtOAC. The combined extracts were washed with water, brine, dried over anhydrous Na2SO4, filtered and evaporated. The crude residue was purifying by preparative HPLC to get tert-butyl(trans)-2-[4(benzyloxy)phenyl]cyclopropyl(2-(4-methylpiperazin-1-yl)-2-oxoethyl)carbamate derivative.

A solution of the latter compound (1 equiv) in Et2O at 0° C. was added Et2O.HCl slowly drop wise, stirred for 1 h at 0° C. to RT. The progress of the reaction was monitored by TLC. After completion reaction mixture was filtered under inert atmosphere and washed with hexane and EtOAC, and dried under reduced pressure to get 2-((trans)-2-(1,1'-biphenyl-4-yl)cyclopropylamino)-1-(4-methylpiperazin-1-yl)ethanone derivative (Overall yield 21%)

¹HNMR (D2O) δ (ppm): 1.33 (m, 1H), 1.50 (m, 1H), 2.52 (m, 1H), 2.91 (s, 4H), 3.11 (m, 3H), 3.57 (d, 3H), 3.95 (d, 1H), 4.32 (d, 2H), 4.55 (d, 1H), 5.11 (s, 2H), 6.98 (d, 2H), 7.09 (d, 2H), 7.41 (m, 5H). MS (M+H): 380.3.

The following examples were synthesized using the procedures described for example 18 employing the corresponding starting materials.

Example 27

2-((trans)-2-(4-(benzyloxy)phenyl)cyclopropylamino)-N-cyclopropylacetamide

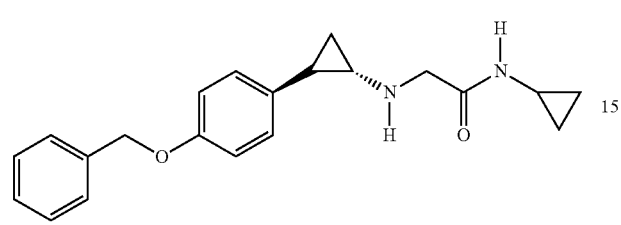

¹HNMR (D₂O) δ (ppm): 0.44 (br, 2H), 0.67 (br, 2H), 0.89 (m, 1H), 1.02 (m, 1H), 1.18 (m, 1H), 1.31 (m, 1H), 2.09 (m, 1H), 2.69 (m, 1H), 5.12 (s, 2H), 6.93 (d, 2H), 7.04 (d, 2H), 7.44 (m, 5H), 8.22 (br, 1H). MS (M+H): 337.3.

Example 28

2-((trans)-2-(4-(3-fluorobenzyloxy)phenyl)cyclopropylamino)-1-(4-methylpiperazin-1-yl)ethanone

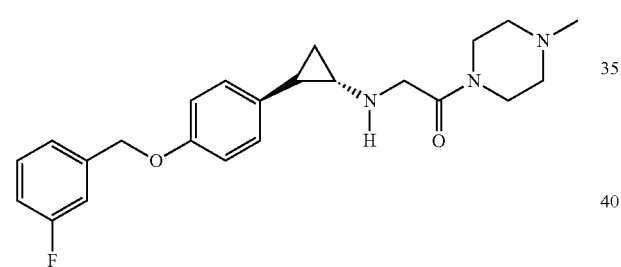

¹HNMR (D₂O) δ (ppm): 1.34 (q, 1H), 1.50 (m, 1H), 2.52 (m, 1H), 2.93 (s, 3H), 2.95 (m, 1H), 3.14 (m, 3H), 3.59 (d, 3H), 3.95 (d, 1H), 4.32 (dd, 2H), 4.55 (d, 1H), 5.11 (s, 2H), 7.05 (dd, 4H), 7.14 (m, 2H), 7.23 (d, 1H), 7.36 (q, 1H). MS (M+H): 398.3.

Example 29

2-((trans)-2-(4-(4-fluorobenzyloxy)phenyl)cyclopropylamino)-1-(4-methylpiperazin-1-yl)ethanone

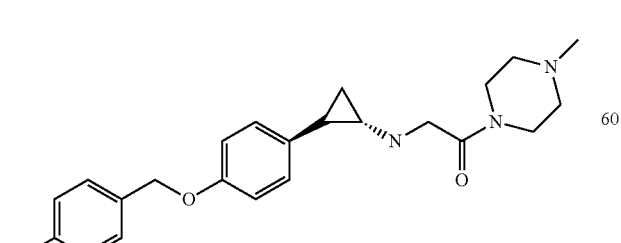

¹HNMR (D₂O) δ (ppm): 1.34 (q, 1H), 1.50 (m, 1H), 2.52 (m, 1H), 2.93 (s, 3H), 2.95 (m, 1H), 3.14 (m, 3H), 3.59 (d, 3H), 3.95 (d, 1H), 4.32 (dd, 2H), 4.55 (d, 1H), 5.09 (s, 2H), 7.07 (dd, 4H), 7.14 (m, 2H), 7.45 (m, 2H). MS (M+H): 290.2.

Example 30

2-((trans)-2-(4-(3-chlorobenzyloxy)phenyl)cyclopropylamino)-1-(4-methylpiperazin-1-yl)ethanone

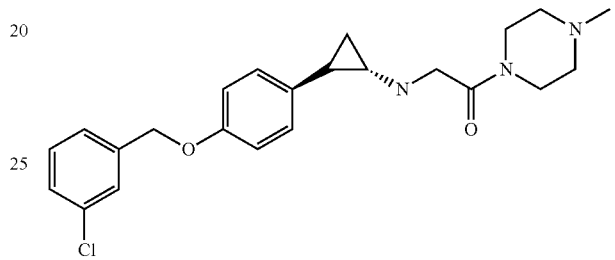

¹HNMR (D₂O) δ (ppm): 1.34 (q, 1H), 1.50 (m, 1H), 2.52 (m, 1H), 2.93 (s, 3H), 2.95 (m, 1H), 3.11 (m, 3H), 3.59 (d, 3H), 3.95 (d, 1H), 4.32 (dd, 2H), 4.55 (d, 1H), 5.09 (s, 2H), 7.02 (dd, 4H), 7.36 (s, 3H), 7.45 (s, 1H). MS (M+H): 414.2.

Example 31

2-((trans)-2-(4-(4-chlorobenzyloxy)phenyl)cyclopropylamino)-1-(4-methylpiperazin-1-yl)ethanone dihydrochloride

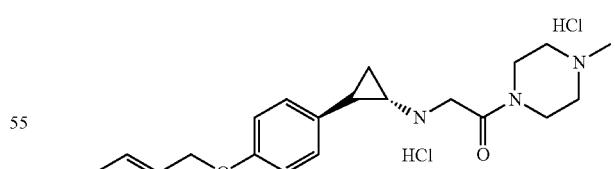

¹H-NMR (D₂O) δ (ppm): 1.33 (q, 1H), 1.49 (m, 1H), 2.53 (m, 1H), 2.93 (s, 4H), 3.13 (m, 3H), 3.60 (m, 3H), 3.93 (m, 1H), 4.36 (d, 2H), 4.53 (m, 1H), 5.09 (s, 2H), 6.96 (d, 2H), 7.13 (d, 2H), 7.40 (s, 4H). MS (M+H): 414.2

Example 32

2-((trans)-2-(4-(3-bromobenzyloxy)phenyl)cyclopropylamino)-1-(4-methylpiperazin-1-yl)ethanone dihydrochloride

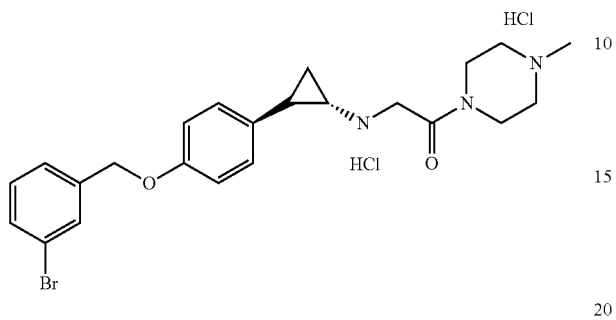

¹H-NMR (DMSO-d6) δ (ppm): 1.21 (q, 1H), 1.53 (m, 1H), 1.76 (br, 2H), 2.78 (s, 3H), 2.93 (br, 1H), 3.07 (br, 1H), 3.22 (br, 1H), 3.41 (br, 1H), 3.60 (s, 2H), 3.91 (br, 1H), 4.28 (d, 2H), 4.41 (br, 1H), 5.11 (s, 2H), 6.94 (d, 2H), 7.11 (d, 2H), 7.35 (t, 1H), 7.43 (d, 1H), 7.52 (d, 1H), 7.63 (s, 1H), 9.65 (br, 1H), 11.62 (br, 1H). MS (M+H): 458.0

Example 33

4-((4-((trans)-2-(2-(4-methylpiperazin-1-yl)-2-oxoethylamino)cyclopropyl)phenoxy)methyl)benzonitrile dihydrochloride

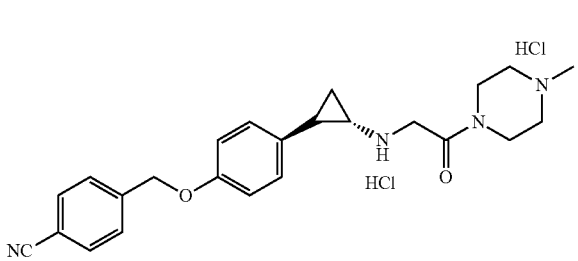

¹H-NMR (D₂O) δ (ppm): 1.36 (q, 1H), 1.51 (m, 1H), 2.53 (m, 1H), 2.93 (s, 4H), 3.13 (m, 3H), 3.58 (m, 3H), 3.93 (d, 1H), 4.36 (d, 2H), 4.53 (m, 1H), 5.22 (s, 2H), 6.98 (d, 2H), 7.13 (d, 2H), 7.58 (d, 2H), 7.73 (d, 2H). MS (M+H): 405.6

Example 34

1-(4-methylpiperazin-1-yl)-2-((trans)-2-(4-phenethoxyphenyl)cyclopropylamino)ethanone

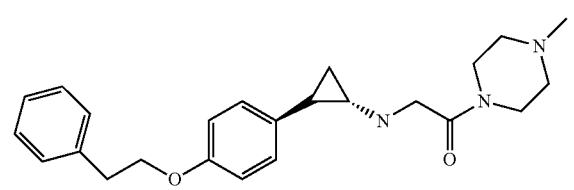

1HNMR 400 MHz (DMSO-d6) δ (ppm): 1.22 (m, 1H), 1.48 (m, 1H), 2.80 (s, 3H), 3.02 (t, 2H), 3.15 (m, 1H), 3.43 (br, 3H), 3.91 (d, 1H), 4.17 (t, 2H), 4.26 (d, 1H), 4.41 (d, 1H), 6.87 (d, 2H), 7.09 (d, 2H), 7.24 (m, 2H), 7.33 (d, 3H), 9.45 (br, 1H), 11.09 (br, 1H). MS (M+H): 394.1.

Example 35

2-((trans)-2-(4-(biphenyl-4-ylmethoxy)phenyl)cyclopropylamino)-1-(4-methylpiperazin-1-yl)ethanone

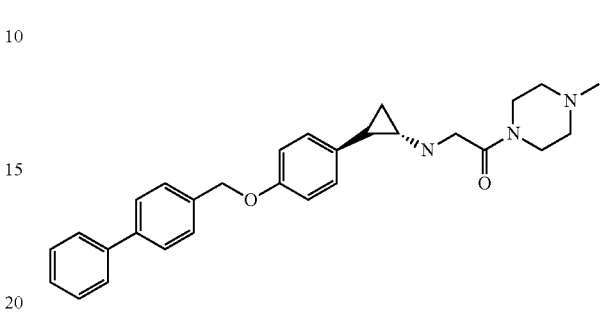

1HNMR 400 MHz (CDCl3) δ (ppm): 1.07 (t, 1H), 1.18 (m, 1H), 1.46 (m, 1H), 2.74 (s, 3H), 3.36 (m, 3H), 3.86 (br, 1H), 4.23 (s, 2H), 4.38 (br, 1H), 5.12 (s, 2H), 6.94 (d, 2H), 7.07 (d, 2H), 7.36 (t, 1H), 7.43 (t, 2H), 7.47 (d, 2H), 7.64 (t, 4H). MS (M+H): 456.2.

Example 36

2-((trans)-2-(biphenyl-4-yl)cyclopropylamino)-1-(4-methylpiperazin-1-yl)ethanone

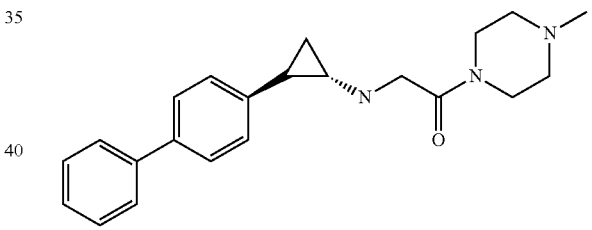

Step-1:
A solution of tert-butyl(trans)-2-(4-bromophenyl)cyclopropylcarbamate (Intermediate F; 1 equiv), 1.2 equiv of the boronic acid, 3.0 equiv of K2CO3 in CH3CN+H2O (4:1) was degassed for 30 mins with Argon gas, added 0.01 equiv of Pd (PPh3)4, heated the reaction mixture at reflux temp for 4 h. The progress of the reaction was monitored by TLC, after completion, poured the reaction mixture into water, extracted with EtOAc. The combined extracts were washed with water, brine, dried over anhydrous Na2SO4, filtered and evaporated. The crude residue was purified by column chromatography to get tert-butyl(trans)-2-(1,1'-biphenyl-4-yl)cyclopropylcarbamate derivative Step-2:
To a suspension of 1.5 equiv of NaH in dry DMF (10 vols) at 0° C. was added a solution of tert-butyl(trans)-2-(1,1'-biphenyl-4-yl)cyclopropylcarbamate derivative (1 equiv) in dry DMF (2 vols) and stirr for 30 mins. Then, added a solution of 1-(chloroacetyl)-4-methylpiperazine (1.5 equiv) in dry DMF (10 mL) at 0° C., stirred for 1 h at 0° C. to RT. The progress of the reaction was monitored by TLC. After completion, reaction mixture was poured into ice water and extracted with EtOAC. The combined extracts were washed with water, brine, dried over anhydrous Na2SO4, filtered and evaporated. The crude residue was purifying by preparative HPLC to get tert-butyl (trans)-2-(1,1'-biphenyl-4-yl)cyclopropyl(2-(4-methylpiperazin-1-yl)-2-oxoethyl)carbamate derivative Step-3

To a solution of tert-butyl(trans)-2-(1,1'-biphenyl-4-yl)cyclopropyl(2-(4-methylpiperazin-1-yl)-2-oxoethyl)carbamate derivative (1 equiv) in Et2O at 0° C. was added Et2O.HCl slowly drop wise, stirred for 1 h at 0° C. to RT. The progress of the reaction was monitored by TLC. After completion reaction mixture was filtered under inert atmosphere and washed with hexane and EtOAC, and dried under reduced pressure to get 2-((trans)-2-(1,1'-biphenyl-4-yl)cyclopropylamino)-1-(4-methylpiperazin-1-yl)ethanone derivative (Overall yield 15%).

$^1$HNMR 400 MHz (CDCl$_3$) δ (ppm): 1.00 (q, 1H), 1.17 (quin, 1H), 1.97 (m, 1H), 2.30 (s, 3H), 2.40 (br, 4H), 2.50 (m, 1H). 3.42 (t, 2H), 3.53 (s, 2H), 3.67 (br, 2H), 7.10 (d, 2H), 7.33 (t, 1H), 7.43 (t, 2H), 7.48 (d, 2H), 7.57 (d, 2H). MS (M+H): 350.0.

The following examples have been synthesized using the procedure described for Example 25, employing the corresponding boronic acid in step 1.

Example 37

2-((trans)-2-(4-pyridin-3-ylphenyl)cyclopropylamino)-1-(4-methylpiperazin-1-yl)ethanone

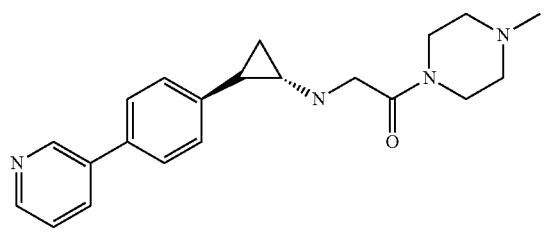

$^1$HNMR 400 MHz (DMSO-d6) δ (ppm): 1.36 (m, 1H), 1.71 (m, 1H), 2.71 (br, 1H), 2.76 (s, 3H), 2.95 (br, 2H), 3.10 (m, 1H), 3.24 (m, 1H), 3.45 (br, 2H), 3.64 (br, 1H), 3.95 (d, 1H), 4.29 (m, 1H), 4.40 (m, 2H), 7.38 (d, 2H), 7.81 (d, 2H), 8.00 (t, 1H), 8.71 (d, 1H), 8.83 (d, 1H), 9.24 (s, 1H), 9.90 (br, 2H), 11.85 (br, 1H). MS (M+H): 351.1.

Example 38

2-((trans)-2-(3'-methoxy-1,1'-biphenyl-4-yl)cyclopropylamino)-1-(4-methylpiperazin-1-yl)ethanone

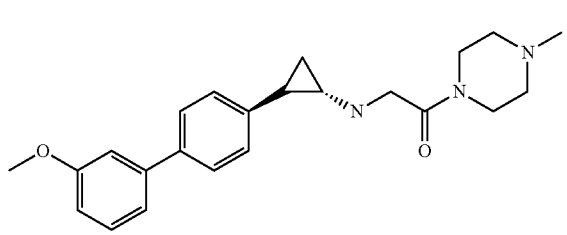

$^1$HNMR 400 MHz (DMSO-d6) δ (ppm): 1.34 (q, 1H), 1.41 (m, 1H), 2.64 (br, 1H), 2.77 (s, 3H), 2.93 (br, 2H), 3.07 (br, 1H), 3.23 (br, 1H), 3.45 (br, 2H), 3.59 (br, 1H), 3.82 (s, 3H), 3.91 (br, 1H), 4.32 (m, 2H), 4.41 (br, 1H), 6.91 (d, 1H), 7.14 (s, 1H), 7.20 (d, 1H), 7.27 (d, 2H), 7.36 (t, 1H), 7.59 (d, 2H), 9.70 (br, 2H), 11.57 (br, 1H). MS (M+H): 380.1.

Example 39

2-((trans)-2-(4'-methoxybiphenyl-4-yl)cyclopropylamino)-1-(4-methylpiperazin-1-yl)ethanone dihydrochloride

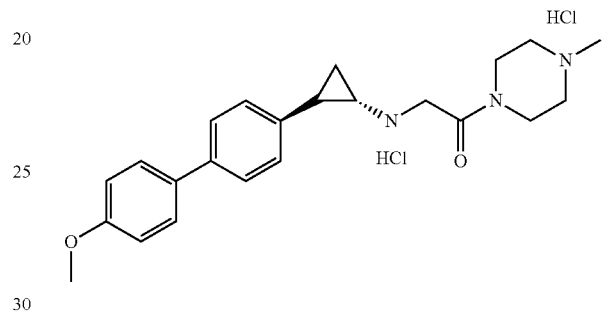

$^1$H-NMR (DMSO-d6) δ (ppm): 1.30 (q, 1H), 1.61 (m, 1H), 2.59 (m, 1H), 2.77 (s, 3H), 2.80 (s, 1H), 2.91 (br, 2H), 3.06 (br, 1H), 3.22 (br, 2H), 3.58 (br, 1H), 3.79 (s, 3H), 3.93 (br, 1H), 4.28 (d, 2H), 4.40 (br, 1H), 7.01 (d, 2H), 7.23 (d, 2H), 7.56 (t, 4H), 9.72 (br, 1H), 11.58 (br, 1H). MS (M+H): 380.1

Example 40

4'-((trans)-2-(2-(4-methylpiperazin-1-yl)-2-oxoethylamino)cyclopropyl)biphenyl-3-carbonitrile dihydrochloride

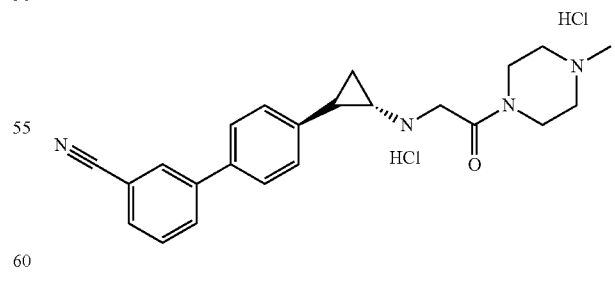

$^1$H-NMR (DMSO-d6) δ (ppm): 1.33 (q, 1H), 1.64 (m, 1H), 2.63 (m, 1H), 2.77 (s, 3H), 2.94 (br, 2H), 3.06 (br, 1H), 3.22 (br, 1H), 3.41 (br, 1H), 3.58 (br, 1H), 3.92 (br, 1H), 4.30 (d, 2H), 4.42 (br, 1H), 7.31 (d, 2H), 7.66 (t, 1H), 7.71 (d, 2H), 7.82 (d, 1H), 7.82 (d, 1H), 8.01 (d, 1H), 8.14 (s, 1H), 9.64 (br, 1H), 11.46 (br, 1H). MS (M+H): 375.1

Example 41

4'-((trans)-2-(2-(4-methylpiperazin-1-yl)-2-oxoethylamino)cyclopropyl)biphenyl-4-carbonitrile dihydrochloride

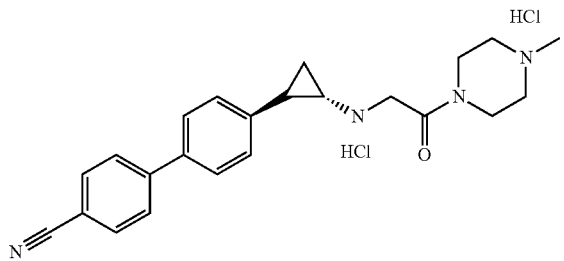

$^1$H-NMR (DMSO-d6) δ (ppm): 1.34 (q, 1H), 1.64 (m, 1H), 2.62 (m, 1H), 2.77 (s, 3H), 2.94 (br, 2H), 3.04 (br, 1H), 3.22 (br, 1H), 3.42 (br, 1H), 3.58 (br, 1H), 3.92 (br, 1H), 4.30 (d, 2H), 4.42 (br, 1H), 7.32 (d, 2H), 7.70 (d, 2H), 7.88 (q, 4H), 9.64 (br, 1H), 11.46 (br, 1H). MS (M+H): 375.0

Example 42

2-((trans)-2-(4'-fluorobiphenyl-4-yl)cyclopropylamino)-1-(4-methylpiperazin-1-yl)ethanone dihydrochloride

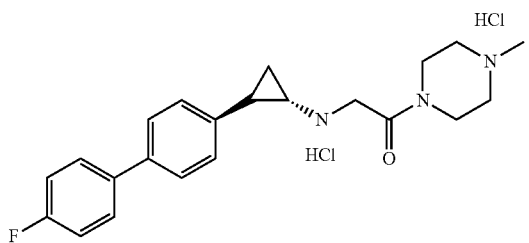

$^1$H-NMR (DMSO-d6) δ (ppm): 1.31 (q, 1H), 1.64 (m, 1H), 2.63 (m, 1H), 2.77 (s, 3H), 2.92 (br, 2H), 3.04 (br, 1H), 3.22 (br, 1H), 3.42 (br, 1H), 3.62 (br, 1H), 3.94 (br, 1H), 4.29 (br, 2H), 4.42 (br, 1H), 7.26 (d, 2H), 7.59 (d, 2H), 7.68 (t, 2H), 9.76 (br, 1H), 11.62 (br, 1H). MS (M+H): 368.1

Example 43

1-(4-methylpiperazin-1-yl)-2-((trans)-2-(3'-(trifluoromethyl)biphenyl-4-yl)cyclopropylamino)ethanone dihydrochloride

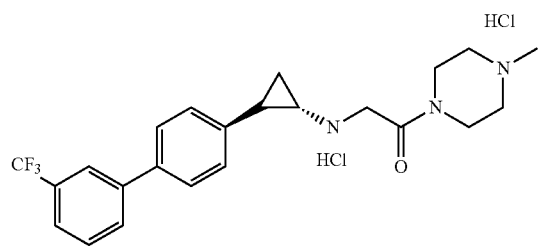

$^1$H-NMR (DMSO-d6) δ (ppm): 1.34 (q, 1H), 1.63 (m, 1H), 2.62 (m, 1H), 2.77 (s, 3H), 2.95 (br, 2H), 3.04 (br, 1H), 3.21 (br, 1H), 3.43 (br, 1H), 3.59 (br, 1H), 3.95 (br, 1H), 4.30 (d, 2H), 4.42 (br, 1H), 7.31 (d, 2H), 7.71 (d, 4H), 7.93 (s, 1H), 7.97 (d, 2H), 9.66 (br, 1H), 11.45 (br, 1H). MS (M+H): 418.1

Example 44

1-(4-methylpiperazin-1-yl)-2-((trans)-2-(4'-(methylsulfonyl)biphenyl-4-yl)cyclopropylamino)ethanone dihydrochloride

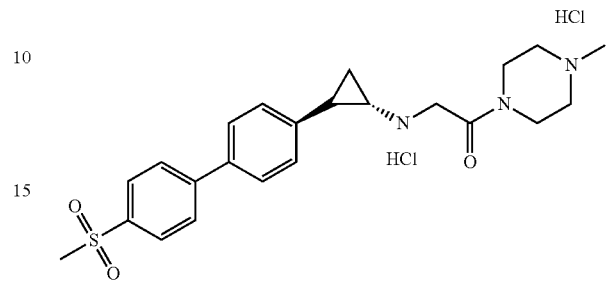

$^1$H-NMR (DMSO-d6) δ (ppm): 1.36 (q, 1H), 1.63 (m, 1H), 2.62 (m, 1H), 2.77 (s, 3H), 2.95 (br, 2H), 3.12 (br, 1H), 3.18 (br, 1H), 3.26 (s, 3H), 3.43 (br, 2H), 3.52 (br, 1H), 3.90 (br, 1H), 4.28 (d, 2H), 4.41 (br, 1H), 7.33 (d, 2H), 7.71 (d, 2H), 7.92 (d, 2H), 7.99 (d, 2H), 9.62 (br, 1H), 11.38 (br, 1H). MS (M+H): 428.5

Example 45

2-((trans)-2-(3',5'-dichlorobiphenyl-4-yl)cyclopropylamino)-1-(4-methylpiperazin-1-yl)ethanone dihydrochloride

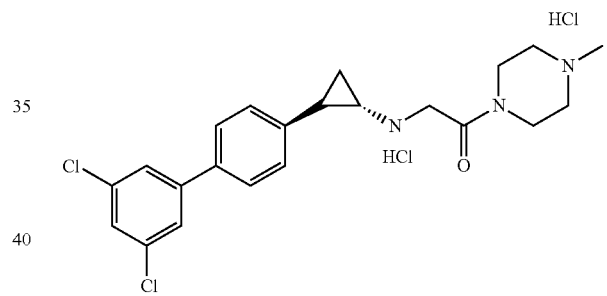

$^1$H-NMR (DMSO-d6) δ (ppm): 1.35 (q, 1H), 1.63 (m, 1H), 2.62 (m, 1H), 2.77 (s, 3H), 2.94 (br, 2H), 3.08 (br, 1H), 3.20 (br, 1H), 3.42 (br, 2H), 3.56 (br, 1H), 3.90 (br, 1H), 4.29 (d, 2H), 4.42 (br, 1H), 7.29 (d, 2H), 7.59 (s, 1H), 7.72 (m, 4H), 9.64 (br, 1H), 11.44 (br, 1H). MS (M+H): 417.8

Example 46

2-((trans)-2-(2',4'-difluorobiphenyl-4-yl)cyclopropylamino)-1-(4-methylpiperazin-1-yl)ethanone dihydrochloride

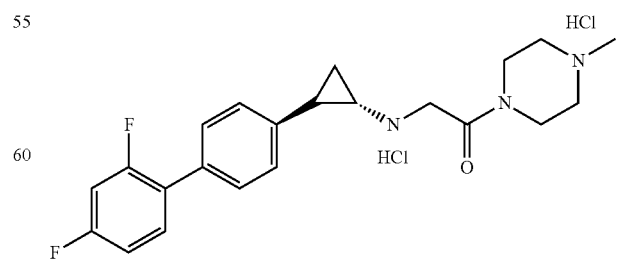

$^1$H-NMR (DMSO-d6) δ (ppm): 1.33 (q, 1H), 1.64 (m, 1H), 2.62 (m, 1H), 2.77 (s, 3H), 2.94 (br, 2H), 3.06 (br, 1H), 3.21

(br, 1H), 3.57 (br, 1H), 3.92 (br, 1H), 4.30 (d, 2H), 4.40 (br, 1H), 7.19 (t, 1H), 7.29 (d, 2H), 7.39 (t, 1H), 7.46 (d, 2H), 7.57 (q, 1H), 9.73 (br, 1H), 11.61 (br, 1H). MS (M+H): 385.9

Example 47

2-((trans)-2-(4-(6-methoxypyridin-3-yl)phenyl)cyclopropylamino)-1-(4-methylpiperazin-1-yl)ethanone

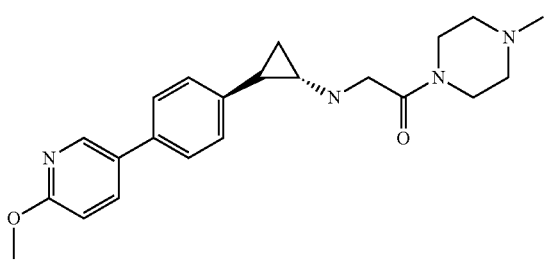

$^1$H-NMR (CDCl3) δ (ppm): 1.00 (q, 1H), 1.17 (m, 1H), 1.97 (m, 1H), 2.29 (s, 3H), 2.38 (br, 4H), 2.51 (m, 1H), 3.41 (t, 2H), 3.53 (s, 2H), 3.65 (br, 2H), 3.97 (s, 3H), 6.80 (d, 1H), 7.10 (d, 2H), 7.40 (d. 2H), 7.75 (d, 1H), 8.35 (s, 1H). MS (M+H): 381.0

Example 48

2-((trans)-2-(2'-fluorobiphenyl-4-yl)cyclopropylamino)-1-(4-methylpiperazin-1-yl)ethanone dihydrochloride

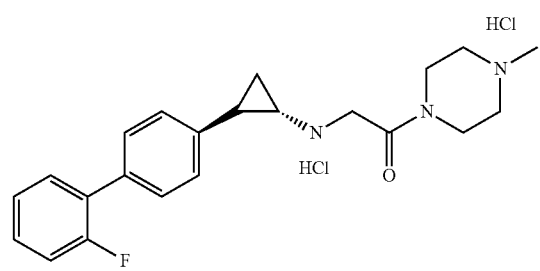

$^1$H-NMR (DMSO-d6) δ (ppm): 1.33 (q, 1H), 1.60 (m, 1H), 2.58 (m, 1H), 2.77 (s, 3H), 2.94 (br, 2H), 3.02 (br, 1H), 3.19 (br, 1H), 3.42 (br, 1H), 3.56 (br, 1H), 3.91 (br, 1H), 4.29 (br, 2H), 4.41 (br, 1H), 7.34 (d, 4H), 7.41 (m, 1H), 7.50 (d, 3H), 9.58 (br, 1H), 11.24 (br, 1H). MS (M+H): 368.2

Example 49

1-(4-methylpiperazin-1-yl)-2-((trans)-2-(4'-(trifluoromethyl)biphenyl-4-yl)cyclopropylamino)ethanone dihydrochloride

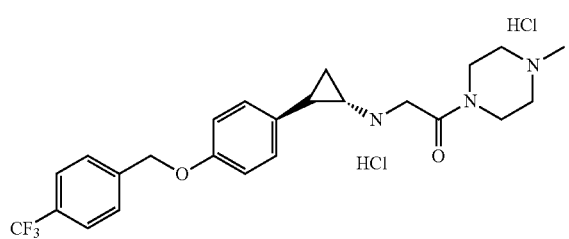

$^1$H-NMR (DMSO-d6) δ (ppm): 1.35 (q, 1H), 1.61 (m, 1H), 2.60 (m, 1H), 2.77 (s, 3H), 2.95 (br, 2H), 3.04 (br, 1H), 3.18 (br, 1H), 3.43 (br, 1H), 3.54 (br, 1H), 3.90 (br, 1H), 4.30 (d, 2H), 4.40 (br, 1H), 7.32 (d, 2H), 7.69 (d, 2H), 7.81 (d, 2H), 7.88 (d, 2H), 9.62 (br, 1H), 11.34 (br, 1H). MS (M+H): 417.9

Example 50

1-(4-methylpiperazin-1-yl)-2-((trans)-2-(2'-(trifluoromethyl)biphenyl-4-yl)cyclopropylamino)ethanone dihydrochloride

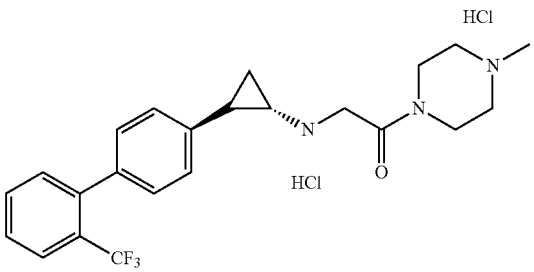

$^1$H-NMR (DMSO-d6) δ (ppm): 1.34 (q, 1H), 1.58 (m, 1H), 2.78 (br, 2H), 2.96 (br, 1H), 3.18 (br, 1H), 3.45 (br, 2H), 3.82 (br, 1H), 4.30 (br, 2H), 4.42 (br, 1H), 7.26 (s, 4H), 7.36 (d, 1H), 7.62 (t, 1H), 7.71 (t, 1H), 7.83 (d, 1H), 9.48 (br, 1H). MS (M+H): 418.2

Example 51

1-(4-methylpiperazin-1-yl)-2-((trans)-2-(4'-(trifluoromethoxy)biphenyl-4-yl)cyclopropylamino)ethanone dihydrochloride

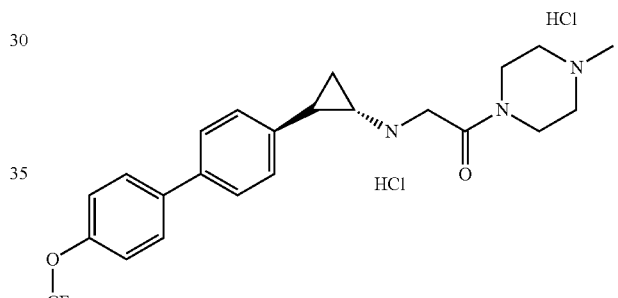

$^1$H-NMR (DMSO-d6) δ (ppm): 1.34 (q, 1H), 1.61 (m, 1H), 2.58 (m, 1H), 2.78 (s, 3H), 2.93 (br, 2H), 3.02 (br, 1H), 3.20 (br, 1H), 3.43 (br, 1H), 3.56 (br, 1H), 3.92 (br, 1H), 4.29 (d, 2H), 4.42 (br, 1H), 7.29 (d, 2H), 7.45 (d, 2H), 7.63 (d, 2H), 7.77 (d, 2H), 9.62 (br, 1H), 11.38 (br, 1H). MS (M+H): 433.9

Example 52

2-((trans)-2-(3'-fluorobiphenyl-4-yl)cyclopropylamino)-1-(4-methylpiperazin-1-yl)ethanone dihydrochloride

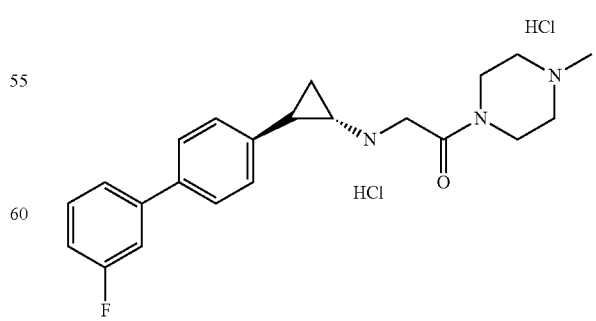

$^1$H-NMR (DMSO-d6) δ (ppm): 1.34 (q, 1H), 1.61 (m, 1H), 2.59 (m, 1H), 2.77 (s, 3H), 2.93 (br, 1H), 3.05 (br, 1H), 3.19

(br, 1H), 3.43 (br, 1H), 3.55 (br, 1H), 3.90 (br, 1H), 4.27 (br, 2H), 4.40 (br, 1H), 7.18 (br, 1H), 7.28 (d, 2H), 7.49 (s, 3H), 7.65 (d, 2H), 9.59 (br, 1H), 11.31 (br, 1H). MS (M+H): 368.2

Example 53

2-((trans)-2-(4'-fluoro-2'-methoxybiphenyl-4-yl)cyclopropylamino)-1-(4-methylpiperazin-1-yl)ethanone dihydrochloride

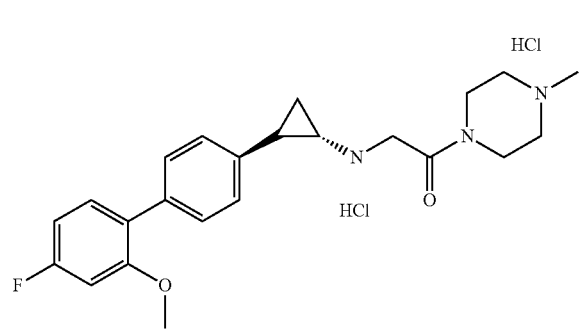

$^1$H-NMR (DMSO-d6) δ (ppm): 1.31 (q, 1H), 1.60 (m, 1H), 2.55 (m, 1H), 2.77 (s, 3H), 2.91 (br, 2H), 3.05 (br, 1H), 3.20 (br, 1H), 3.58 (br, 1H), 3.77 (s, 3H), 3.93 (br, 1H), 4.29 (d, 2H), 4.40 (br, 1H), 6.83 (t, 1H), 7.02 (d, 1H), 7.20 (d, 2H), 7.27 (t, 1H), 7.37 (d, 2H), 9.63 (br, 1H), 11.41 (br, 1H). MS (M+H): 397.9

Example 54

1-(4-methylpiperazin-1-yl)-2-((trans)-2-(4-(pyridin-4-yl)phenyl)cyclopropylamino)ethanone trihydrochloride

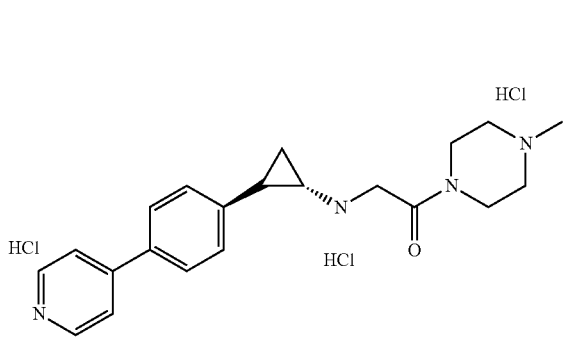

$^1$H-NMR (DMSO-d6) δ (ppm): 1.40 (q, 1H), 1.69 (m, 1H), 2.68 (m, 1H), 2.77 (s, 3H), 3.00 (m, 3H), 3.21 (br, 1H), 3.42 (br, 2H), 3.58 (br, 1H), 3.92 (br, 1H), 4.25 (d, 2H), 4.41 (br, 1H), 7.41 (d, 2H), 7.96 (d, 2H), 8.25 (s, 2H), 8.88 (s, 2H), 9.77 (br, 2H), 11.46 (br, 1H). MS (M+H): 351.2

Example 55

2-((trans)-2-(3'-chlorobiphenyl-4-yl)cyclopropylamino)-1-(4-methylpiperazin-1-yl)ethanone dihydrochloride

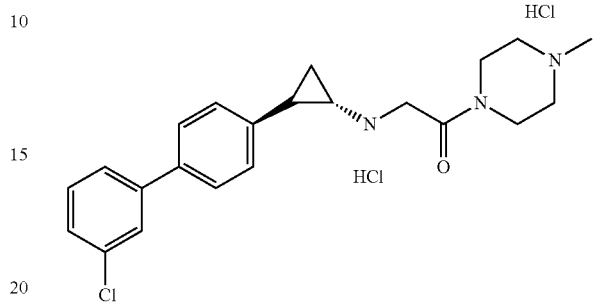

$^1$H-NMR (DMSO-d6) δ (ppm): 1.34 (q, 1H), 1.58 (m, 1H), 2.67 (m, 1H), 2.77 (s, 3H), 2.93 (br, 2H), 3.04 (br, 1H), 3.16 (br, 1H), 3.45 (br, 1H), 3.58 (br, 1H), 3.89 (br, 1H), 4.29 (br, 2H), 4.40 (br, 1H), 7.28 (d, 2H), 7.42 (d, 1H), 7.48 (t, 1H), 7.64 (t, 3H), 7.70, (s, 1H), 9.56 (br, 1H), 11.22 (br, 1H). MS (M+H): 384.1

Example 56

2-((trans)-2-(4'-chlorobiphenyl-4-yl)cyclopropylamino)-1-(4-methylpiperazin-1-yl)ethanone dihydrochloride

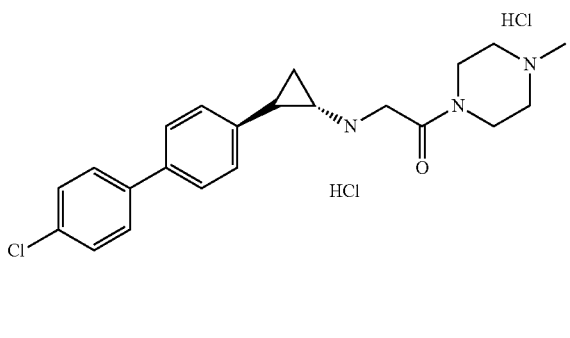

$^1$H-NMR (DMSO-d6) δ (ppm): 1.35 (q, 1H), 1.59 (m, 1H), 2.58 (m, 1H), 2.78 (s, 3H), 2.93 (br, 2H), 3.04 (br, 1H), 3.18 (br, 1H), 3.41 (br, 1H), 3.54 (br, 1H), 3.92 (br, 1H), 4.29 (br, 2H), 4.42 (br, 1H), 7.28 (d, 2H), 7.51 (d, 2H), 7.61 (d, 2H), 7.68, (d, 2H), 9.60 (br, 1H), 11.25 (br, 1H). MS (M+H): 383.9

Example 57

2-((trans)-2-(5'-fluoro-2'-(trifluoromethyl)biphenyl-4-yl)cyclopropylamino)-1-(4-methylpiperazin-1-yl)ethanone dihydrochloride

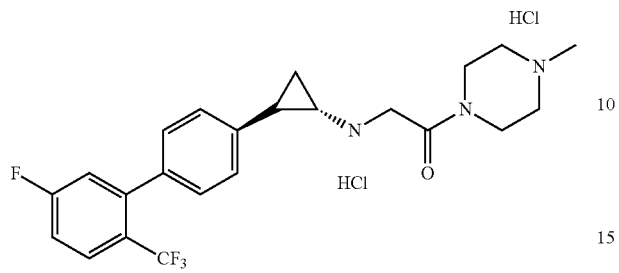

$^1$H-NMR (DMSO-d6) δ (ppm): 1.32 (q, 1H), 1.61 (m, 1H), 2.58 (m, 1H), 2.77 (s, 3H), 2.92 (br, 2H), 3.05 (br, 1H), 3.17 (br, 1H), 3.45 (br, 1H), 3.74 (s, 3H), 3.94 (br, 1H), 4.27 (d, 2H), 4.40 (br, 1H), 7.14 (m, 3H), 7.21 (d, 2H), 7.43 (d, 2H), 9.63 (br, 1H), 11.42 (br, 1H). MS (M+H): 398.2

Example 58

2-((trans)-2-(4-(2-methoxypyridin-3-yl)phenyl)cyclopropylamino)-1-(4-methylpiperazin-1-yl)ethanone

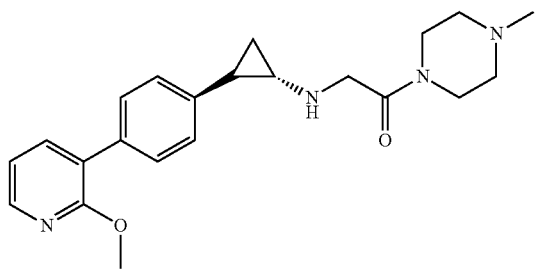

$^1$H-NMR (CDCl$_3$) δ (ppm): 1.00 (q, 1H), 1.17 (quin, 1H), 1.97 (m, 1H), 2.31 (s, 3H), 2.40 (br, 4H), 2.51 (m, 1H), 3.41 (br, 2H), 3.53 (s, 2H), 3.66 (br, 2H), 3.96 (s, 3H), 6.95 (t, 1H), 7.08 (d, 2H), 7.44 (d, 2H), 7.57 (d, 1H), 8.14 (d, 1H). MS (M+H): 381.2

Example 59

1-(4-methylpiperazin-1-yl)-2-((trans)-2-(4-phenethylphenyl)cyclopropylamino) ethanone dihydrochloride

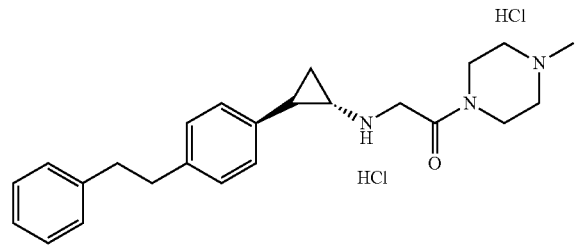

$^1$H-NMR (DMSO-d6) δ (ppm): 1.23 (q, 1H), 1.52 (m, 1H), 2.77 (s, 3H), 2.84 (s, 4H), 2.92 (br, 1H), 3.03 (br, 1H), 3.18 (br, 1H), 3.37 (br, 2H), 3.54 (br, 1H), 3.92 (br, 1H), 4.27 (d, 2H), 4.42 (br, 1H), 7.07 (d, 2H), 7.17 (d, 2H), 7.25 (m, 5H), 9.53 (br, 1H), 11.31 (br, 1H). MS (M+H): 378.2

Example 60

2-((trans)-2-(4-cyclopropylphenyl)cyclopropylamino)-1-(4-methylpiperazin-1-yl)ethanone dihydrochloride

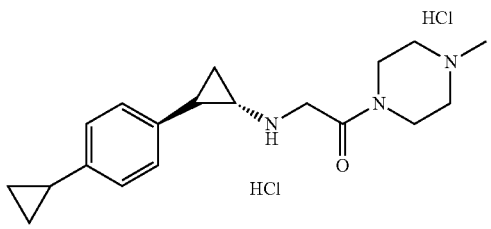

$^1$H-NMR (DMSO-d6) δ (ppm): 0.61 (d, 2H), 0.91 (d, 2H), 1.22 (q, 1H), 1.52 (m, 1H), 1.86 (m, 1H), 2.78 (s, 3H), 2.81 (br, 1H), 2.93 (br, 1H), 3.03 (br, 1H), 3.20 (br, 1H), 3.56 (br, 1H), 3.89 (br, 1H), 4.26 (d, 2H), 4.41 (br, 1H), 7.03 (q, 4H), 9.56 (br, 1H), 11.38 (br, 1H). MS (M+H): 314.2

Example 61

Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (from 0 to 75 μM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 μM of di-methylated H3-K4 peptide was add to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and leaved to incubate for 30 extra minutes at room temperature in the dark. A 1 μM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki of each inhibitor was estimated at half of the maximum activity.

In preliminary assays, a number of the compounds of the invention were tested for their ability to inhibit LSD1 and where found to have Ki values lower than 100 μM, including the compounds in examples 3, 6, 7 and 11. Compound of examples 1, 2, 4, 5, 9, 10, and 12 were found to have Ki values for LSD1 of around or less than 10 μM. Schmidt et al. noted that the IC50 values for irreversible inhibitors of LSD1 like parnate can greatly depend on assay conditions (See Schmidt et al. (2007) *Biochemistry* 46(14)4408-4416). The inventors have had a similar experience have noticed some variations in Ki values (IC50) for the compounds described herein in these assays due to slight variations in assay conditions, enzyme preparations, inhibitor stability etc. Compounds of Example 8 and 21 did not inhibit LSD1 in these assays which indicates that large substitutions on the phenylcyclopropyl amine (R6), like the arylalkyl group (phenyl-CH$_2$—) of Example 21 reduce inhibitory activity towards LSD1. Furthermore, when aryl groups are present in the molecule covalently bonded to the amide nitrogen of the phenylcyclopropylamine acetamide core (e.g, the 4-fluorophenyl group of Example 8), such compounds appear to be inactive. Without wishing to be bound by theory, one explanation for the lack of activity of compounds like that of Example 8 is that they may have reduced stability. Thus, preferred embodiments and aspects of the compounds, compositions of the invention and their uses do not have these types of groups at these respective positions. For example, preferred embodiments and aspects of the invention are those where $R_x$ and $R_y$ are not phenyl groups or optionally substituted phenyl groups. Preferably $R_x$ and $R_y$ are groups like cycloalkyl, alkyl, and alkynyl where one of $R_x$ and $R_y$ is a hydrogen atom. Additionally it is preferred that R6 is not a large group like benzyl. It is preferred that R6 is a hydrogen atom.

Thus, the inventors have discovered a class of phenylcyclopropylamine acetamide derivatives with surprising inhibitory activity against LSD1. Later studies with direct comparisons to parnate show that many of the compounds of Formula I have improved inhibitory activity to LSD1 (see results below). Surprisingly, in view of references such as Zirle et al. ((1962) *J. Med. Chem.* 1265-1284), who report that larger substitutions on the nitrogen of tranylcypromine seem to decrease amine oxidase inhibitory ability; the inventors have found that such substitutions increase inhibitory activity towards LSD1. Furthermore, in view of references such as Gooden et al. ((2008) *Bioorg. Med. Chem. Let.* 18:3047-3051), the inventors have surprisingly discovered modifications to the phenylcyclopropylamine scaffold that result in LSD1 selective inhibitors that have Ki (IC50) values for LSD1 inhibition that are lower than that their respective Ki (IC50) values for MAO-A and/or MAO-B.

The results presented in Table 1 below shows results obtained with compounds of the Examples (e.g., of Formula I). Parnate (2-trans phenylcyclopropylamine) was found to have a Ki of from about 15 to 35 micromolar in the same assay depending on the enzyme preparation which is consistent with published literature results. Furthermore, when Parnate (e.g., tranylcypromine) was tested in the MAO-A activity assay it was found to have an Ki (IC50) value of about 2 micromolar, when Parnate was tested in the MAO-B activity assay it was found to have an Ki (IC50) value of about 0.6 micromolar, both consistent with literature reported values.

Numerous compounds of Examples were found to have Ki values for LSD1 of less than 1 micromolar. Compounds having Ki values for LSD1 of less than 35 micromolar are preferred compounds of the invention. Even more preferred compounds of the invention are those that have Ki values for LSD1 of less than 15 micromolar. Another group of more preferred compounds of the invention are those that have a Ki value for LSD1 of less than 1 micromolar.

Example 62

Biological Assays—Monoamine Oxidase Assays

Human recombinant monoamine oxidase proteins MAO-A and MAO-B were purchased from Sigma Aldrich. MOAs catalyze the oxidative deamination of 1°, 2° and 3° amines. In order to monitor MAO enzymatic activities and/or their inhibition rate by inhibitor(s) of interest, a fluorescent-based (inhibitor)-screening assay was set up. 3-(2-Aminophenyl)-3-oxopropamamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 μL. The assay buffer was 100 mM HEPES, pH 7.5. Each experiment was performed in triplicate within the same experiment.

Briefly, a fixed amount of MAO (0.25 μg for MAO-A and 0.5 μg for MAO-B) was incubated on ice for 15 minutes in the reaction buffer, in the absence and/or in the presence of various concentrations of inhibitor (from 0 to 50 μM, depending on the inhibitor strength). Tranylcypromine (Biomol International) was used as a control for inhibition.

After leaving the enzyme(s) interacting with the inhibitor, 60 to 90 μM of kynuramine was added to each reaction for MAO-B and MAO-A assay respectively, and the reaction was left for 1 hour at 37° C. in the dark. The oxidative deamination of the substrate was stopped by adding 50 μL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki of each inhibitor was measure at Vmax/2.

TABLE 1

| # Example | MAO A (Ki) | MAO B (Ki) | LSD1 (Ki) |
|---|---|---|---|
| 1 | >50 μM | 76 μM | 6.0 μM |
| 2 | >50 μM | >>75 μM | 3 μM |
| 3 | >100 μM | >100 μM | 4.07 |
| 4 | >50 μM | >75 μM | 6 μM |
| 5 | >50 μM | >75 μM | 19 μM |
| 6 | >50 μM | >50 μM | 23 μM |
| 7 | >50 μM | 42 μM | 9 μM |
| 8 | >50 μM | >50 μM | >50 μM |
| 9 | >100 μM | >100 μM | 6.39 μM |
| 10 | 200 μM | >100 μM | 4.70 μM |
| 11 | >>40 μM | >>40 μM | 0.240 μM |
| 12 | >>40 μM | >40 μM | 0.040 μM |
| 13 | >>40 μM | >>40 μM | 4.4% @ 0.25 μM |
| 14 | 42 μM | 19.2 μM | 0.221 μM |
| 15 | 31.8 μM | 8.8 μM | 0.118 μM |
| 16 | 25.5 μM | >>40 μM | 0.009 μM |
| 17 | >>40 μM | >40 μM | 0.197 μM |

TABLE 1-continued

| # Example | MAO A (Ki) | MAO B (Ki) | LSD1 (Ki) |
|---|---|---|---|
| 18 | >>40 μM | >>40 μM | 0.072 μM |
| 19 | 74 μM | >100 μM | 34% at 20 μM |
| 20 | >100 μM | >100 μM | 40% at 20 μM |
| 21 | n.d. | n.d. | >100 μM |
| 22 | >>50 μM | 31 μM | 0.35 μM |
| 23 | >>50 μM | >>50 μM | 0.26 μM |
| 24 | 11 μM | 7 μM | 1.04 μM |
| 25 | 2.32 μM | 1.9 μM | 1.2 μM |
| 26 | 11 μM | 9 μM | 0.03 μM |
| 27 | 4.47 | 1.25 μM | 0.52 μM |
| 28 | 22.1 μM | 2.0 μM | 0.018 μM |
| 29 | >>40 μM | 4.0 μM | 0.022 μM |
| 30 | 23.3 μM | 2.4 μM | 0.047 μM |
| 31 | >>40 μM | 6.4 μM | 0.015 μM |
| 32 | 24.0 μM | 3.9 μM | 0.025 μM |
| 33 | 14.2 μM | 4.6 μM | 0.017 μM |
| 34 | 39 μM | 24.7 μM | 0.161 μM |
| 35 | 21.4 μM | 3.2 μM | 0.390 μM |
| 36 | 31.4 μM | 36.7 μM | 0.100 μM |
| 37 | >>40 μM | >>40 μM | 0.043 μM |
| 38 | 29.8 μM | 31.6 μM | 0.025 μM |
| 39 | 27.5 μM | 29.3 μM | 0.030 μM |
| 40 | 31.4 μM | 18.2 μM | 0.026 μM |
| 41 | >40 μM | 7.4 μM | 0.027 μM |
| 42 | >>40 μM | 40.4 μM | 0.042 μM |
| 43 | 7.9 μM | 26.1 μM | 0.140 μM |
| 44 | 41.7 μM | 12.1 μM | 0.024 μM |
| 45 | 8.6 μM | 18.3 μM | 0.026 μM |
| 46 | 38.4 μM | 24.6 μM | 0.024 μM |
| 47 | 8.1 μM | >40 μM | 0.135 μM |
| 48 | 31.9 μM | 25.9 μM | 0.029 μM |
| 49 | >40 μM | 3.0 μM | 0.124 μM |
| 50 | 25 μM | >40 μM | 0.160 μM |
| 51 | >40 μM | 4.2 μM | 0.098 μM |
| 52 | 37.9 μM | 25.4 μM | 0.040 μM |
| 53 | 25.9 μM | >40 μM | 0.134 μM |
| 54 | >40 μM | >40 μM | 0.063 μM |
| 55 | 27.7 μM | 32.8 μM | 0.021 μM |
| 56 | 42.6 μM | 24.5 μM | 0.059 μM |
| 57 | 14.8 μM | >>40 μM | 0.009 μM |
| 58 | 6.4 μM | 39.7 μM | 0.047 μM |
| 59 | 18.9 μM | 18.2 μM | 0.025 μM |
| 60 | >40 μM | 42.1 μM | 0.018 μM |

Previous reports of LSD1 have found that it is involved in cell proliferation and growth. Some studies have implicated LSD1 as a therapeutic target for cancer. Huang et al. (2007) *PNAS* 104:8023-8028 found that polyamines inhibitors of LSD1 modestly cause the reexpression of genes aberrantly silenced in cancer cells. Scoumanne et al. ((2007) *J. Biol. Chem.* May 25; 282(21):15471-5) found that deficiency in LSD1 leads to a partial cell cycle arrest in G2/M and sensitizes cells to growth suppression induced by DNA damage. Kahl et al. ((2006) *Cancer Res.* 66(23):11341-7.) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol.* 13:563-567) reported that tranylcypromie derepresses Egr-1 gene expression in some cancer lines. A body of evidence is accumlating that Egr-1 is a tumor suppressor gene in many contexts (see e.g., Calogero et al. (2004) Cancer Cell International 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogneic effects and inhibits tumor growth in some models; Ferraro et al. ((2005) *J. Clin. Oncol.* March 20; 23(9):1921-6) reported that Egr-1 is downregulated in lung cancer patients with a higher risk of recurrence and may be more resistant to therapy. Other studies have implicated LSD1 and/or histone methylation in various cancers including kidney, lung, and breast cancer. Thus, increasing Egr-1 expression via inhibition of LSD1 is a therapeutic approach for some cancers.

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat such diseases.

The results disclosed herein show that modifications to the phenylpropylamine core with substituted acetamides can result in potent LSD1 inhibitors. The examples show compounds which selectively inhibit LSD1 compared to MAO-A and MAO-B. Thus, the inventors have discovered unexpectedly a new class of phenylcyclopropylamine containing amine oxidase inhibitors with activity against biologically relevant targets in CNS conditions and oncology.

The invention therefore provides inhibitors selective for LSD1 which inhibit LSD1 to a greater extent than MAO-A and/or MAO-B in the above described assays. Preferred LSD1 selective inhibitors have IC50 values for LSD1 which are about at least 2-fold lower than the IC50 value for MAO-A and/or MAO-B. One example of an LSD1 selective inhibitor is shown in Table 1 is Example 3 which has an 1050 for LSD1 which is about at least 10-fold lower than for MAO-A and MAO-B. Another example of an LSD1 selective inhibitor is in Example 4 which has an 1050 for LSD1 which is more than about 5-fold lower than the 1050 for MAO-A and MAO-B. Yet another example of a selective LSD1 inhibitor is given in Example 7 which has an 1050 which is more than 3-fold lower for LSD1 than MAO-A and MAO-B. Yet another example of a selective LSD1 inhibitor is given in Example 24 which has an 1050 which is more than about 5-fold lower for LSD1 than MAO-A and MAO-B. Yet another example of a selective LSD1 inhibitor is given in Example 36 which has an 1050 which is more than 10-fold lower for LSD1 than MAO-A and MAO-B. Yet another example of a selective LSD1 inhibitor is given in Example 34 which has an 1050 which is more than 10-fold lower for LSD1 than MAO-A and MAO-B. Yet another example of a selective LSD1 inhibitor is given in Example 35 which has an 1050 which is more than 5-fold lower for LSD1 than MAO-A and MAO-B.

Furthermore, in the above described assays, the compound of Example 37 was found to have an 1050 value for LSD1 of about 29-43 nanomolar and 1050 value for MAO-B and MAO-B of greater than 40 micromolar. Additionally, in the above described assays, the compound of Example 38 was found to have an 1050 value for LSD1 of 25 nanomolar, and MAO-B of 31.6 micromolar and MAO-A of 29.8.6 micromolar.

Particular amine oxidase inhibitors of the invention which are LSD1 selective include those of Example 26, Example 28, Example 30, and Example 35 which all have 1050 values below 100 nanomolar and 1050 value for MAO-A and MAO-B typically in the low micromolar range.

MAO-B inhibitors are clinically useful for treating neurodegeneration and depression. For example, MAO-B inhibitors have been used to treat Parkinson's disease, and have been shown to have neuroprotective properties in some models. Therefore, the compounds of Formula I may be used to treat such conditions, particularly where LSD1 inhibition is likely to help therapeutically. LSD1, protein complexes in which LSD1 is a member of, and/or histone lysine methylation have been shown to be linked a number of neurodegenerative diseases including, Huntington's disease, Alzheimer's disease, Dementia, Lewy Body dementia, and Frontal temporal dementia.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

What is claimed is:

1. A compound of Formula I or a pharmaceutically acceptable salt thereof:

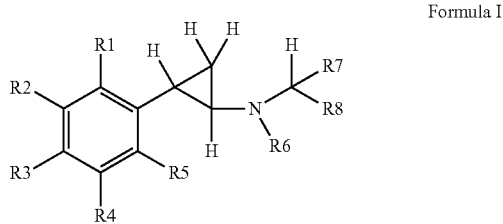

Formula I wherein each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is chosen from —C(=O)NR$_x$R$_y$, and —C(=O)R$_z$;
R$_x$ when present is chosen from —H, alkyl, alkynyl, alkenyl, -L-carbocycle, and -L-heterocyclyl, all of which are optionally substituted;
R$_y$ when present is chosen from —H, alkyl, alkynyl, alkenyl, -L-carbocycle, -L-aryl, and -L-heterocyclyl, all of which are optionally substituted;
R$_z$ when present is chosen from —H, alkoxy, -L-carbocycle, -L-heterocyclyl, and -L-aryl, wherein the aryl, heterocyclyl or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)NH (CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

2. The compound of claim 1, wherein each -L- is independently selected from the group consisting of —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3.

3. The compound of claim 1 or a pharmaceutically acceptable salt thereof
wherein R1 and R5 are independently selected from the group consisting of hydro, halo, C1-C6 alkyl, C1-C6 alkoxy, C1-C6 haloalkyl, C1-C6 haloalkoxy, and cyano; one of R2, R3, and R4 is chosen from -L-aryl and -L-heterocyclyl wherein -L- is independently selected from the group consisting of —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S (CH$_2$)$_n$—, where each n is independently chosen from 0, 1, 2, and 3; the others of R2, R3, and R4 are independently selected from the group consisting of hydro, halo, C1-C6 alkyl, C1-C6 alkoxy, C1-C6 haloalkyl, C1-C6 haloalkoxy, and cyano; R6 is chosen from hydro, C1-C6 alkyl, C1-C6 haloalkyl; R7 is chosen from hydro, C1-C6 alkyl, and cycloalkyl; R8 is —C(=O)R$_z$;
wherein R$_z$ is an optionally substituted -L-heterocyclyl group having from 1-4 optional substituents wherein the optional substituents are independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfonyl, sulfonyl, sulfonamide, thiocarbonyl, thiocyanato, trihalomethanesulfonamido, O-carbamyl, N-carbamyl, O-thiocarbamyl, N-thiocarbamyl, and C-amido, and wherein -L- is independently chosen from —(CH$_2$)$_n$—(CH$_2$)$_n$—, —(CH$_2$)$_n$NH (CH$_2$)$_n$—, —(CH$_2$)$_n$O(CH$_2$)$_n$—, and —(CH$_2$)$_n$S (CH$_2$)$_n$—, where each n is independently chosen from 0, 1, 2, and 3.

4. A compound of Formula I or a pharmaceutically acceptable salt thereof:

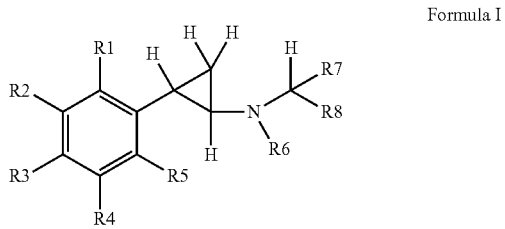

Formula I wherein R3 is an optionally substituted aryl group having from 1-4 optional substituents;
each of R1, R2, R4 and R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is chosen from —C(=O)NR$_x$R$_y$ and —C(=O)R$_z$;
R$_x$ when present is chosen from alkynyl, alkenyl, -L-carbocycle, -L-aryl, and -L-heterocyclyl, all of which are optionally substituted;
R$_y$ when present is chosen from —H, alkyl, alkynyl, alkenyl, -L-carbocycle, -L-aryl, and -L-heterocyclyl, all of which are optionally substituted;
R$_z$ when present is chosen from —H, alkoxy, -L-carbocycle, -L-heterocyclyl, and -L-aryl, wherein the aryl, heterocyclyl or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)nNHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)NH(CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

5. The compound of claim 4, wherein R3 is a optionally substituted phenyl group and the 1-4 optional substituents are independently chosen from halo, alkyl, alkoxy, haloalkyl, haloalkoxy, sulphonyl, and cyano.

6. A compound of Formula I or a pharmaceutically acceptable salt thereof:

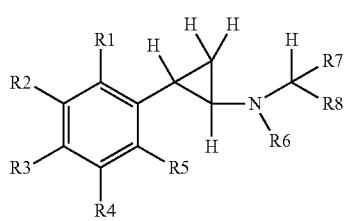

Formula I wherein R3 is an optionally substituted arylalkoxy group having from 1-4 optional substituents;
each of R1, R2, R4 and R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is chosen from —C(=O)NR$_x$R$_y$ and —C(=O)R$_z$;
R$_x$ is chosen from —H, alkyl, alkynyl, alkenyl, -L-carbocycle, -L-aryl, and -L-heterocyclyl, all of which are optionally substituted;
R$_y$ when present is chosen from —H, alkyl, alkynyl, alkenyl, -L-carbocycle, -L-aryl, and -L-heterocyclyl, all of which are optionally substituted;
R$_z$ when present is chosen from —H, alkoxy, -L-carbocycle, -L-heterocyclyl, and -L-aryl, wherein the aryl, heterocyclyl or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)nNHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$ S(CH$_2$)$_n$—, and —(CH$_2$)$_n$NHC(=S)NH(CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

7. The compound of claim 6, wherein R3 is an optionally substituted benzyloxy group and the 1-4 optional substituents are independently chosen from halo, alkyl, alkoxy, haloalkyl, haloalkoxy, sulphonyl, and cyano.

8. The compound of claim 1, wherein each of R1-R5 is independently chosen from —H, halo, C1-C4 alkyl, C1-C4 alkoxy, C1-C4 haloalkyl, —OCH$_2$(phenyl), and C1-C4 haloalkoxy.

9. The compound of claim 1, wherein each of R1-R5 is independently chosen from —H, halo, —OCH$_2$ (phenyl) and —CF$_3$.

10. The compound of claim 1, wherein each of R1-R5 is —H.

11. The compound of claim 1, wherein R6 is —H or a C1-C4 alkyl.

12. The compound of claim 1, wherein R7 is —H or a C1-C4 alkyl.

13. The compound of claim 1, wherein each L is independently chosen from a bond, —CH$_2$—, —CH$_2$CH$_2$—, —OCH$_2$—, —OCH$_2$CH$_2$—, —CH$_2$OCH$_2$—, —CH$_2$CH$_2$CH$_2$—, —OCH$_2$CH$_2$CH$_2$—, and —CH$_2$OCH$_2$CH$_2$—.

14. The compound of claim 1, wherein each L is independently chosen from a bond, —CH$_2$—, —CH$_2$CH$_2$—, and —CH$_2$CH$_2$CH$_2$—.

15. The compound of claim 1, wherein L is chosen from a bond and —CH$_2$—.

16. The compound of claim 1, wherein $R_x$ when present, is chosen from $C_1$-$C_6$ alkyl, $C_2$-$C_6$ alkenyl, $C_2$-$C_6$ alkynyl, -L-cycloalkyl, and -L-heterocyclyl, all of which are optionally substituted.

17. The compound of claim 1, wherein $R_x$ when present is chosen from —H, —CH(CH$_3$)$_2$, —C(CH$_3$)$_3$, —CH$_2$C≡CH, —CH$_2$CH=CH$_2$, cyclopropyl, cyclobutyl, cyclopentyl, and cyclohexyl, wherein the cyclopropyl, cyclobutyl, cyclopentyl, and cyclohexyl group is optionally substituted.

18. The compound of claim 1, wherein $R_y$, when present, is chosen from C1-C6 alkyl, $C_2$-$C_6$ alkenyl, $C_2$-$C_6$ alkynyl, -L-cycloalkyl, -L-aryl, and -L-heterocyclyl, wherein the cycloalkyl, aryl, and heterocyclyl can be optionally substituted.

19. A compound of Formula I or a pharmaceutically acceptable salt thereof:

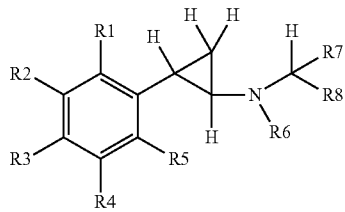

Formula I wherein
each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is chosen from —C(=O)NR$_x$R$_y$, and —C(=O)R$_z$;
$R_x$ when present is chosen from —H, alkyl, alkynyl, alkenyl, -L-carbocycle, -L-aryl, and -L-heterocyclyl, all of which are optionally substituted;
$R_y$ when present is chosen from —H, —CH(CH$_3$)$_2$, —C(CH$_3$)$_3$, —CH$_2$C≡CH, —CH$_2$CH=CH$_2$, cyclopropyl, cyclobutyl, cyclopentyl, cyclohexyl, and —CH$_2$(phenyl), wherein the cyclopropyl, cyclobutyl, cyclopentyl, cyclohexyl and phenyl group is optionally substituted;
$R_z$ when present is chosen from —H, alkoxy, -L-carbocycle, -L-heterocyclyl, and -L-aryl, wherein the aryl, heterocyclyl or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and —(CH$_2$)$_n$NHC(=S)NH(CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

20. The compound of claim 1, wherein $R_z$ when present is an optionally substituted -L-heterocyclyl.

21. The compound of claim 1, wherein $R_z$ when present is optionally substituted and chosen from N-methylpiperazinyl, morpholinyl, and piperidinyl.

22. The compound of claim 1, wherein $R_z$ is chosen from N-methylpiperazinyl, morpholinyl, and piperidinyl.

23. A pharmaceutical composition comprising a compound of claim 1 or a pharmaceutically acceptable salt thereof and a pharmaceutically acceptable carrier.

24. A method of treating cancer, the method comprising administering to an individual the compound of claim 1, wherein the cancer is selected from the group consisting of breast cancer, colorectal cancer, lung cancer, prostate cancer, testicular cancer, brain cancer, and any combination thereof.

25. A method of treating a neurodegenerative disease or disorder, the method comprising administering to an individual the compound of claim 1, wherein the neurodegenerative disease or disorder is selected from the group consisting of Parkinson's Disease, Huntington's disease, Alzheimer's disease, Lewy Body dementia, and Frontal temporal dementia, an any combination thereof.

26. The compound of claim 1, wherein the compound has the trans configuration around the cyclopropyl ring.

27. A compound selected from the group consisting of N-cyclopropyl-2-{[(trans)-2-phenylcyclopropyl]amino}acetamide; 2-{[(trans)-2-phenylcyclopropyl]amino}acetamide; N-cyclopropyl-2-{[(trans)-2-phenylcyclopropyl]amino}propanamide; 2-{[(trans)-2-phenylcyclopropyl]amino}-N-prop-2-ynylacetamide; N-isopropyl-2-{[(trans)-2-phenylcyclopropyl]amino}acetamide; N-(tert-butyl)-2-{[(trans)-2-phenylcyclopropyl]amino}acetamide; N-(2-morpholin-4-yl-2-oxoethyl)-N-[(trans)-2-phenylcyclopropyl]amine; 2-{[(trans)-2-phenylcyclopropyl]amino}propanamide; methyl 2-{[(trans)-2-phenylcyclopropyl]amino}propanoate; N-cyclopropyl-2-{methyl[(trans)-2-phenylcyclopropyl]amino}acetamide; 2-{methyl[(trans)-2-phenylcyclopropyl]amino}acetamide; N-methyl-trans-2-(Phenylcyclopropylamino)propanamide; 1-(4-methylpiperazin-1-yl)-2-((trans)-2-phenylcyclopropylamino)ethanone; 1-(4-ethylpiperazin-1-yl)-2-((trans)-2-phenylcyclopropylamino)ethanone; 1-(4-benzylpiperazin-1-yl)-2-((trans)-2-phenylcyclopropylamino)ethanone; 2-((trans)-2-phenylcyclopropylamino)-1-(4-phenylpiperazin-1-yl)ethanone; 2-((trans)-2-(4-(benzyloxy)phenyl)cyclopropylamino)-1-(4-methylpiperazin-1-yl)ethanone; 2-((trans)-2-(4-(benzyloxy)phenyl)cyclopropylamino)-N-cyclopropylacetamide; 2-((trans)-2-(4-(3-fluorobenzyloxy)phenyl)cyclopropylamino)-1-(4-methylpiperazin-1-yl)ethanone; 2-((trans)-2-(4-(3-chlorobenzyloxy)phenyl)cyclopropylamino)-1-(4-methylpiperazin-1-yl)ethanone; 2-((trans)-2-(biphenyl-4-yl)cyclopropylamino)-1-(4-methylpiperazin-1-yl)ethanone; 1-(4-methylpiperazin-1-yl)-2-((trans)-2-(4-phenethoxyphenyl)cyclopropylamino)ethanone; 2-((trans)-2-(4-(4-fluorobenzyloxy)phenyl)cyclopropylamino)-1-(4-methylpiperazin-1-yl)ethanone; and 2-((trans)-2-(4-(biphenyl-4-ylmethoxy)phenyl)cyclopropylamino)-1-(4-methylpiperazin-1-yl)ethanone; or a pharmaceutically acceptable salt thereof.

28. A compound selected from the group consisting of 2-({(trans)-2-[4-(benzyloxy)phenyl]cyclopropyl}amino)-N-cyclopropylacetamide, N-[(trans)-2-(4-benzyloxyphenyl)cyclopropyl]}-N-[2-(4-methylpiperazin-1-yl)-2-oxoethyl]amine, N-[2-oxo-2-(4-phenylpiperazin-1-yl)ethyl]-N-[(trans)-2-phenylcyclopropyl]amine, N-[2-(4-benzylpiperazin-1-yl)-2-oxoethyl]-N-[(trans)-2-phenylcyclopropyl]amine, N-[2-(4-ethylpiperazin-1-yl)-2-oxoethyl]-N-[(trans)-2-phenylcyclopropyl]amine, N-[2-(4-methylpiperazin-1-yl)-2-oxoethyl]-N-[(trans)-2-phenylcyclopropyl]amine, 2-((trans)-2-(4-pyridin-3-ylphenyl)cyclopropylamino)-1-(4-methylpiperazin-1-yl)ethanone, and 2-((trans)-2-(3'-methoxy-1,1'-biphenyl-4-yl)cyclopropylamino)-1-(4-methylpiperazin-1-yl)ethanone, or a pharmaceutically acceptable salt thereof.

29. A method for screening for an agent that inhibits LSD1 and/or LSD1 and MAO-B selectively compared to MAO-A comprising:

(a) assaying the compound of claim 1 for its ability to inhibit LSD1, MAO-B, and MAO-A, (b) wherein the compound of claim 1 is a selective inhibitor of LSD1 and/or LSD1 and MAO-B if the compound of claim 1 has an inhibitory constant for LSD1 or LSD1 and MAO-B that is at least two-fold lower than its inhibitory constant for MAO-A.

30. The compound of claim 1 wherein R8 is —C(=O)$R_z$.

31. The compound of claim 1 wherein one of R2, R3, and R4 is chosen from -L-aryl and -L-heterocyclyl wherein -L- is independently selected from the group consisting of —$(CH_2)_n$—$(CH_2)_n$—, —$(CH_2)_n$NH$(CH_2)_n$—, —$(CH_2)_n$O$(CH_2)_n$—, and —$(CH_2)_n$S$(CH_2)_n$—, where each n is independently chosen from 0, 1, 2, and 3; and the others of R2, R3, and R4 are independently selected from the group consisting of hydro, halo, C1-C6 alkyl, C1-C6 alkoxy, C1-C6 haloalkyl, C1-C6 haloalkoxy, and cyano.

* * * * *